(12) United States Patent
Kim et al.

(10) Patent No.: US 8,354,383 B2
(45) Date of Patent: *Jan. 15, 2013

(54) 6,11-BRIDGED BIARYL MACROLIDES

(75) Inventors: In Jong Kim, Lexington, MA (US); Tongzhu Liu, Auberdale, MA (US); Jiang Long, Wayland, MA (US); Guoqiang Wang, Belmont, MA (US); Yao-Ling Qiu, Andover, MA (US); Heejin Kim, Belmont, MA (US); Yanchun Wang, Newton, MA (US); Ly Tam Phan, Quincy, MA (US); Yat Sun Or, Watertown, MA (US)

(73) Assignee: Enanta Pharmaceuticals, Inc., Watertown, MA (US)

( * ) Notice: Subject to any disclaimer, the term of this patent is extended or adjusted under 35 U.S.C. 154(b) by 648 days.

This patent is subject to a terminal disclaimer.

(21) Appl. No.: 12/399,801

(22) Filed: Mar. 6, 2009

(65) Prior Publication Data

US 2009/0264380 A1    Oct. 22, 2009

Related U.S. Application Data

(63) Continuation-in-part of application No. 12/212,596, filed on Sep. 17, 2008, now abandoned.

(60) Provisional application No. 60/973,017, filed on Sep. 17, 2007, provisional application No. 60/973,201, filed on Sep. 18, 2007, provisional application No. 61/051,875, filed on May 9, 2008, provisional application No. 61/095,111, filed on Sep. 8, 2008, provisional application No. 61/051,857, filed on May 9, 2008, provisional application No. 61/076,208, filed on Jun. 27, 2008, provisional application No. 61/051,862, filed on May 9, 2008, provisional application No. 61/076,213, filed on Jun. 27, 2008, provisional application No. 61/095,100, filed on Sep. 8, 2008.

(51) Int. Cl.
*A61K 31/70* (2006.01)
*C07H 17/08* (2006.01)
(52) U.S. Cl. ......................... 514/29; 536/7.4

(58) Field of Classification Search .................. 536/7.4
See application file for complete search history.

(56) References Cited

U.S. PATENT DOCUMENTS

| | | |
|---|---|---|
| 4,921,836 A | 5/1990 | Bigham et al. |
| 4,990,602 A | 2/1991 | Morimoto et al. |
| 5,202,434 A | 4/1993 | Wilkening |
| 5,403,923 A | 4/1995 | Kashimura et al. |
| 5,441,939 A | 8/1995 | Yang |
| 5,444,051 A | 8/1995 | Agouridas et al. |
| 5,527,780 A | 6/1996 | Agouridas et al. |
| 5,556,839 A | 9/1996 | Greene et al. |
| 5,631,355 A | 5/1997 | Asaka et al. |
| 5,780,605 A | 7/1998 | Or et al. |
| 5,866,549 A | 2/1999 | Or et al. |
| 5,922,683 A | 7/1999 | Or et al. |
| 5,969,161 A | 10/1999 | Bonnet et al. |
| 6,046,171 A | 4/2000 | Or et al. |
| 6,054,435 A | 4/2000 | Or et al. |
| 6,075,133 A | 6/2000 | Or et al. |
| 6,124,269 A | 9/2000 | Phan et al. |
| 6,274,715 B1 | 8/2001 | Or et al. |
| 6,355,620 B1 | 3/2002 | Ma et al. |
| 6,399,582 B1 | 6/2002 | Hlasta et al. |
| 6,764,998 B1 | 7/2004 | Wang et al. |
| 6,878,691 B2 | 4/2005 | Or et al. |
| 7,022,679 B2 | 4/2006 | Kim et al. |
| 7,049,417 B2 | 5/2006 | Or et al. |
| 7,064,110 B2 | 6/2006 | Or et al. |
| 7,129,221 B2 | 10/2006 | Or et al. |
| 7,135,573 B2 | 11/2006 | Kim et al. |
| 7,189,704 B2 | 3/2007 | Niu et al. |
| 7,229,972 B2 | 6/2007 | Or et al. |
| 7,265,094 B2 | 9/2007 | Qiu et al. |
| 7,273,853 B2 | 9/2007 | Or et al. |
| 7,384,921 B2 | 6/2008 | Tang et al. |
| 7,384,922 B2 | 6/2008 | Wang et al. |
| 7,414,030 B2 | 8/2008 | Vo et al. |
| 2005/0009761 A1 | 1/2005 | Or |
| 2006/0252712 A1 | 11/2006 | Wang et al. |
| 2007/0082853 A1 | 4/2007 | Or et al. |
| 2007/0244160 A1 | 10/2007 | Or et al. |
| 2009/0075915 A1 | 3/2009 | Kim et al. |
| 2009/0118506 A1 | 5/2009 | Kim et al. |

FOREIGN PATENT DOCUMENTS
WO    2005061525 A1    7/2005

OTHER PUBLICATIONS

U.S. Appl. No. 12/388,333, In Jong Kim, et al.
International Search Report from PCT/US08/76731, dated Jun. 19, 2009.
Qui, et al., "In Vitro and In Vivo Evaluation of EP-014598: A New Bicyclolide Active against Resistant Pathogens with Exceptional Pharmacokinetic Profiles", Poster Presentation, Sep. 19, 2007, ICAAC Annual Meeting, Sep. 17-20, 2007.

*Primary Examiner* — Elli Peselev
(74) *Attorney, Agent, or Firm* — Elmore Patent Law Group, P.C.; Edgar W. Harlan; Carolyn S. Elmore, Esq.

(57) ABSTRACT

The present invention discloses compounds of formula I, II or X, or pharmaceutically acceptable salts, esters, or prodrugs thereof:

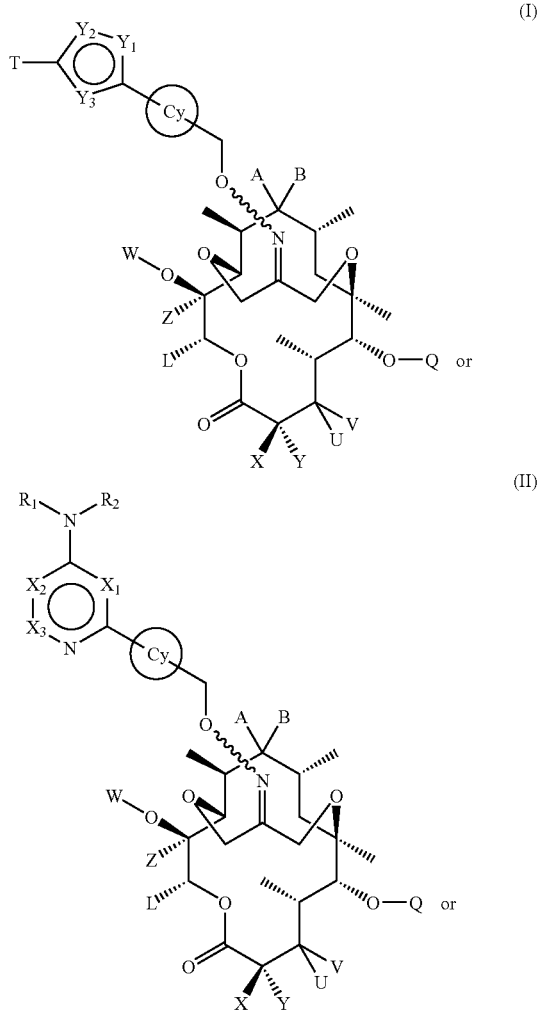

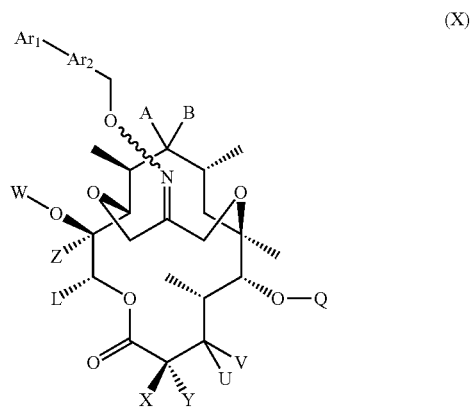

which exhibit antibacterial properties. The present invention further relates to pharmaceutical compositions comprising the aforementioned compounds for administration to a subject in need of antibiotic treatment. The invention also relates to methods of treating a bacterial infection in a subject by administering a pharmaceutical composition comprising the compounds of the present invention. The invention further includes process by which to make the compounds of the present invention.

34 Claims, No Drawings

6,11-BRIDGED BIARYL MACROLIDES

RELATED APPLICATIONS

This application is a continuation-in-part of U.S. application Ser. No. 12/212,596, filed Sep. 17, 2008, which claims the benefit of U.S. provisional application No. 60/973,017 filed on Sep. 17, 2007; U.S. provisional application No. 60/973,201 filed on Sep. 18, 2007; U.S. provisional application No. 61/051,875 filed on May 9, 2008; U.S. provisional application No. 61/095,111 filed on Sep. 8, 2008; U.S. provisional application No. 61/051,857 filed on May 9, 2008; U.S. provisional application No. 61/076,208 filed on Jun. 27, 2008; U.S. provisional application No. 61/051,862 filed on May 9, 2008; U.S. provisional application No. 61/076,213 filed on Jun. 27, 2008; and U.S. provisional application No. 61/095,100 filed on Sep. 8, 2008. The contents of the above applications are incorporated herein by reference.

TECHNICAL FIELD

The present invention relates to novel semi-synthetic macrolides having antibacterial activity and useful in the treatment and prevention of bacterial infections. More particularly, the invention relates to macrolide derivatives containing a biaryl moiety on a 6,11-bridged macrolide system, compositions comprising such compounds, methods for using the same, and processes by which to make such compounds.

BACKGROUND OF THE INVENTION

The spectrum of activity of macrolides, including erythromycin, covers most relevant bacterial species responsible for upper and lower respiratory tract infections. 14-membered ring macrolides are well known for their overall efficacy, safety and lack of serious side effects. Erythromycin however is quickly degraded into inactive products in the acidic medium of the stomach resulting in low bioavailability and gastrointestinal side effects. Improvement of erythromycin pharmacokinetics has been achieved through the synthesis of more acid-stable derivatives, for example, roxithromycin, clarithromycin, and the 15-membered ring macrolide azithromycin. However, all of these drugs, including 16-membered ring macrolides, present several drawbacks. They are inactive against $MLS_B$-resistant streptococci ($MLS_B$=Macrolides-Lincosamides-type B Streptogramines) and with the exception of azithromycin, weakly active against *Haemophilus influenzae*. Furthermore, the resistance of *Streptococcus pneumoniae* to erythromycin has increased significantly in recent years (5% to above 40%). There is a high percentage of cross-resistance to penicillin among these isolates, with a worldwide epidemic spread of 10-40% in some areas.

There is, therefore, a clear need for new macrolides that overcome the problem of pneumococcal resistance, have good pharmacokinetic properties and acid stability while continuing to be active against *H. influenzae*.

Currently there is a new medical needs due to an increasing prevalence of community acquired Methicillin-Resistant *Staphylococcus aureus* (CA-MRSA) in skin and soft tissue infections as well as nosocomial acquired MRSA. MRSA is a particular type of the bacteria that has developed resistance to many antibiotics, including methicillin, making it difficult to treat. Previously, MRSA infection was a problem mainly for patients treated in hospitals. Now, we are seeing MRSA in the general community, creating a tremendous need for new antibiotics with an improved safety profile and more convenient administration for use in hospitals as well as in community settings. The growing problem of bacterial resistance to many existing drugs also necessitates the development of new antibiotics to fight the battle.

Current macrolide antibiotics, including erythromycin A, clarithromycin, and azithromycin have been successfully used in the treatment of respiratory tract and skin and soft tissue infections. Macrolides are generally safe and well tolerated. However, extensive clinical use of macrolides has resulted in the rapid emergence of macrolide resistance in staphylococci, streptococci, and enterococci. Current macrolide antibiotics are not active against the majority of MRSA isolates.

Improving activity of macrolides against MRSA isolates are the focus of this invention in addition to improving *Haemophilus influenzae* activities.

These new macrolides will be ideal candidates for drug development for skin and soft tissue infections and in upper respiratory tract infections ("URTI") and lower respiratory tract infections ("LRTI").

SUMMARY OF THE INVENTION

The present invention provides 14-membered ring bridged macrolide compounds or pharmaceutically-acceptable salts, esters, or prodrugs thereof containing biaryl moieties that shows improved MIC and/or pharmacokinetic properties. The present invention further relates to pharmaceutical compositions, comprising the compounds of the present invention, for administration to a subject in need of antibiotic treatment. The invention also relates to methods of treating a bacterial infection in a subject by administering a pharmaceutical composition comprising the compounds of the present invention. The invention further includes process by which to make the compounds of the present invention.

In one embodiment of the present invention, there are disclosed compounds of formula I or II:

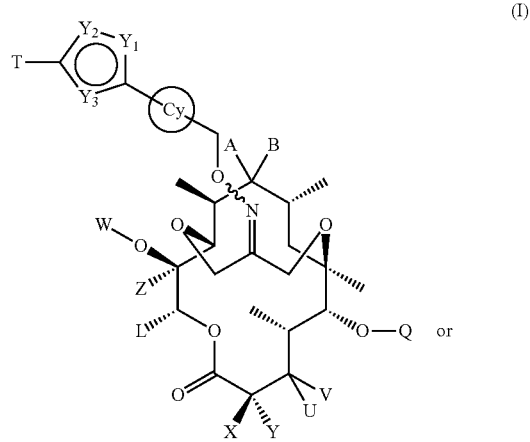

or

-continued (II)

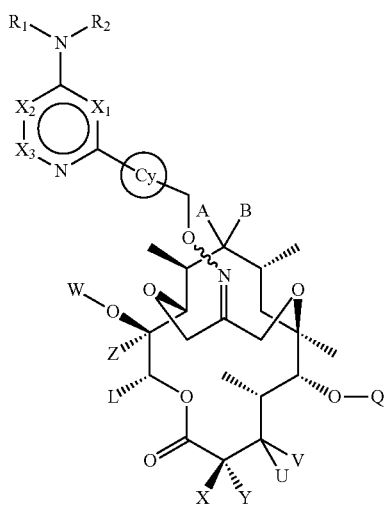

as well as the pharmaceutically acceptable salts, esters and prodrugs thereof, wherein: T is hydrogen, $OR_3$, halogen or $NR_1R_2$, where $R_1$ and $R_2$ are each independently selected from:
(a) hydrogen;
(b) —$R_3$, where $R_3$ is substituted or unsubstituted —$C_1$-$C_6$ alkyl, —$C_2$-$C_6$ alkenyl, or —$C_2$-$C_6$ alkynyl each containing 0, 1, 2, or 3 heteroatoms selected from O, S or N;
(c) —$C(O)R_4$; where $R_4$ is independently selected from the group consisting of:
(i) hydrogen;
(ii) aryl; substituted aryl; heteroaryl; substituted heteroaryl;
(iii) —$R_3$; and
(iv) —$R_5$, where $R_5$ is substituted and unsubstituted —$C_3$-$C_{12}$ cycloalkyl each containing 0, 1, 2, or 3 heteroatoms selected from O, S or N;
(d) —$C(O)NHR_4$;
(e) —$C(O)OR_4$; and
(f) —$S(O)_2R_4$;
alternatively, $R_1$ and $R_2$ can be taken together with the nitrogen they are attached with to form a fused or non-fused, substituted or unsubstituted heterocyclic ring;
$Y_1$ is S or O;
$Y_2$ and $Y_3$ are each independently selected from S, N, O or $CR_{10}$; where $R_{10}$ is independently selected from hydrogen, hydroxy, amino, halogen, substituted or unsubstituted alkoxy, substituted or unsubstituted alkylamino, substituted or unsubstituted dialkylamino, $CF_3$, CN, $NO_2$, $N_3$, sulfonyl, acyl, aliphatic, and substituted aliphatic;
provided that when either $Y_1$ or $Y_3$ is S and $Y_2$ is CH or N, T is not hydrogen;
$X_1$, $X_2$ and $X_3$ are each independently selected from N or $CR_{10}$;
Cy is substituted or unsubstituted heterocyclic, or substituted or unsubstituted heteroaryl;
A and B are each independently selected from:
(a) hydrogen;
(b) —$R_3$;
(c) —$OR_4$;
(d) —$OC(O)R_4$;
(e) —$OC(O)NHR_4$;
(f) —$OC(O)OR_4$;
(g) —$NR_8R_9$; where $R_8$ and $R_9$ are each independently selected from $R_3$; alternatively, $R_8$ and $R_9$ taken together with the nitrogen atom to which they are connected form a 3- to 10-membered ring which may optionally contain one or more heterofunctions selected from the group consisting of: —O—, —NH—, —N($C_1$-$C_6$-alkyl)-, —N($R_{10}$)—, —S(O)$_n$—, wherein n=0, 1 or 2, and $R_{10}$ is selected from aryl; substituted aryl; heteroaryl; and substituted heteroaryl;
(h) —$NHC(O)R_4$;
(i) —$NHS(O)_2R_4$;
(j) —$NHC(O)OR_4$; and
(k) —$NHC(O)NHR_4$;
alternatively, A and B taken together with the carbon atom to which they are attached are selected from:
(a) C=O;
(b) C=N-J-$R_{11}$, where J is absent, O, C(O), $SO_2$, NH, NHC(O), NHC(O)NH or $NHSO_2$; and wherein $R_{11}$ is independently selected from halogen and $R_4$;
(c) C=CH-J-$R_{11}$; and
(d) substituted or unsubstituted, and saturated or unsaturated 5- to 10-membered heterocyclic;
L is independently selected from $R_3$;
W is selected from:
(a) hydrogen;
(b) hydroxy prodrug group;
(c) —$R_3$;
(d) —$C(O)R_4$;
(e) —$C(O)O—R_4$; and
(f) —$C(O)N(R_8R_9)$;
Q is:
(a) —$R_4$;
(b) —$C(O)R_4$;
(c) —$C(O)NHR_4$;
(d) —$C(O)OR_4$;
(e) —$S(O)_2R_4$;
(f) monosaccharide;
(g) disaccharide; or
(h) trisaccharide;
Z is:
(a) hydrogen;
(b) —$N_3$;
(c) —CN;
(d) —$NO_2$;
(e) —$C(O)NH_2$;
(f) —C(O)OH;
(g) —CHO;
(h) —$R_3$;
(i) —$C(O)OR_3$;
(j) —$C(O)R_3$; or
(k) —$C(O)NR_8R_9$;
when U is hydrogen, V is selected from the group consisting of:
(a) hydrogen;
(b) —$OR_4$;
(c) —$OC(O)R_4$;
(d) —$OC(O)NHR_4$;
(e) —$OS(O)_2R_4$;
(f) —O-monosaccharide; and
(g) —O-disaccharide;

alternatively, U and V taken together with the carbon atom they are attached is C=O; each of X and Y is independently:

(a) hydrogen;
(b) hydroxy;
(c) $NR_8R_9$;
(d) halogen; or
(e) —$R_3$.

In another embodiment of the present invention there are disclosed pharmaceutical compositions comprising a therapeutically effective amount of a compound of the invention in combination with a pharmaceutically acceptable carrier or excipient. In yet another embodiment of the invention are methods of treating antibacterial infections in a subject in need of such treatment with said pharmaceutical compositions. Suitable carriers and formulations of the compounds of the present invention are disclosed.

DETAILED DESCRIPTION OF THE INVENTION

A first embodiment of the present invention is a compound of formula I or II as illustrated above, or a pharmaceutically acceptable salt, ester or prodrug thereof.

Preferred subgenera of the present invention are:

a compound of formula (III):

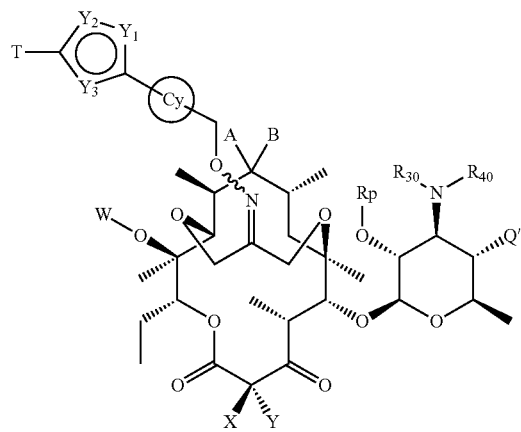

(III)

wherein $R_p$ is hydrogen, hydroxy protected group or hydroxy prodrug group;

Q' is:
(a) hydrogen;
(b) $OR_p$; or
(c) —$OR_5$, where $R_5$ is selected from the group consisting of:
  (i) —$R_3$; and
  (ii) substituted and unsubstituted —$C_3$-$C_{12}$ cycloalkyl containing 0, 1, 2, or 3 heteroatoms selected from O, S or N;

$R_{30}$ and $R_{40}$ is independently selected from the group consisting of hydrogen, acyl, a substituted or unsubstituted, saturated or unsaturated aliphatic group, a substituted or unsubstituted, saturated or unsaturated alicyclic group, a substituted or unsubstituted aromatic group, a substituted or unsubstituted heteroaromatic group, saturated or unsaturated heterocyclic group; or can be taken together with the nitrogen atom to which they are attached to form a substituted or unsubstituted heterocyclic or heteroaromatic ring; and T, Cy, $Y_1$-$Y_3$, W, X, Y, A and B are as previously defined. A compound of formula (IV):

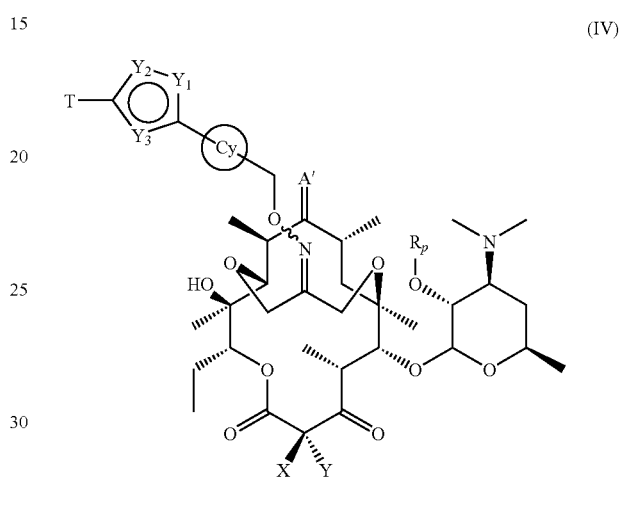

(IV)

wherein A' is O or $NC(O)R_{11}$; $R_p$ is hydrogen, hydroxy protected group or hydroxy prodrug group; and T, Cy, $Y_1$-$Y_3$, X, and Y are as previously defined. A compound of formula V:

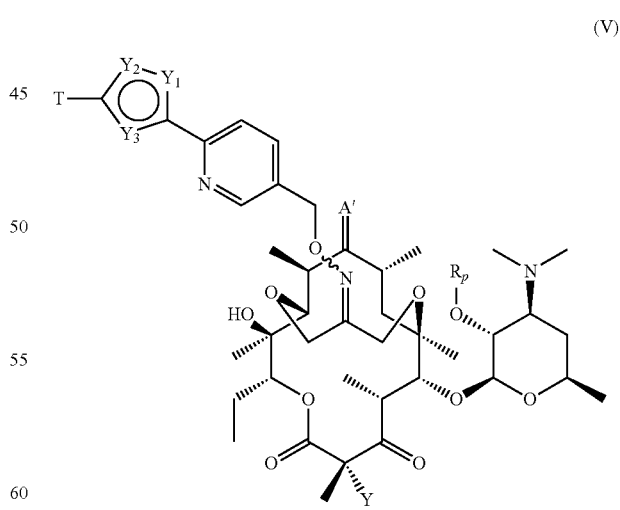

(V)

wherein A' is O or $NC(O)R_{11}$; $R_p$ is hydrogen, hydroxy protected group or hydroxy prodrug group; and T, $Y_1$-$Y_3$, $R_{11}$ and Y are as previously defined.

A compound of formula VI:

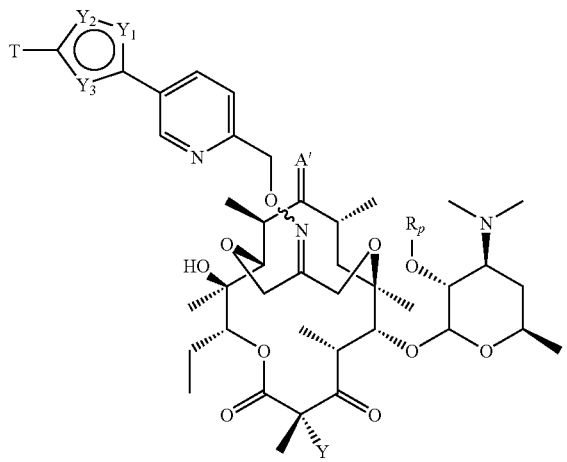
(VI)

wherein A' is O or NC(O)R$_{11}$; R$_p$ is hydrogen, hydroxy protected group or hydroxy prodrug group; and T, Y$_1$-Y$_3$, R$_1$ and Y are as previously defined.

A compound of formula VII:

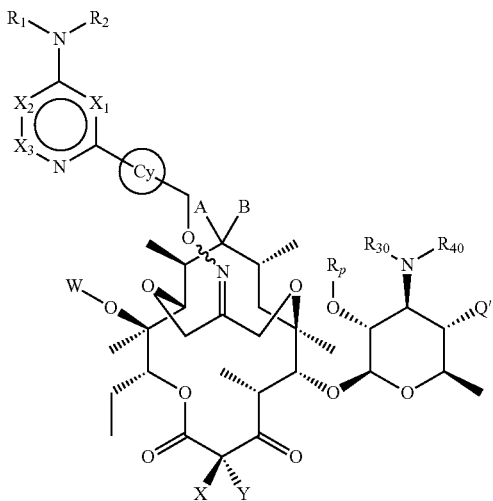
(VII)

wherein R$_p$ is hydrogen, hydroxy protected group or hydroxy prodrug group;

Q' is:
(a) hydrogen;
(b) OR$_p$; or
(c) —OR$_5$, where R$_5$ is selected from the group consisting of:
  (i) —R$_3$; and
  (ii) substituted and unsubstituted —C$_3$-C$_{12}$ cycloalkyl containing 0, 1, 2, or 3 heteroatoms selected from O, S or N;

R$_{30}$ and R$_{40}$ is independently selected from the group consisting of hydrogen, acyl, a substituted or unsubstituted, saturated or unsaturated aliphatic group, a substituted or unsubstituted, saturated or unsaturated alicyclic group, a substituted or unsubstituted aromatic group, a substituted or unsubstituted heteroaromatic group, saturated or unsaturated heterocyclic group; or can be taken together with the nitrogen atom to which they are attached to form a substituted or unsubstituted heterocyclic or heteroaromatic ring; and R$_1$, R$_2$, Cy, X$_1$-X$_3$, W, X, Y, A and B are as previously defined.

A compound of formula VIII:

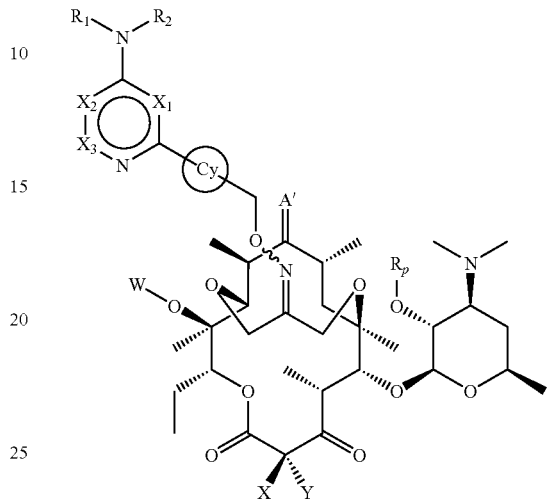
(VIII)

wherein A' is O or NC(O)R$_{11}$; R$_p$ is hydrogen, hydroxy protected group or hydroxy prodrug group; and T, Y$_1$-Y$_3$, R$_{11}$ and Y are as previously defined.

In another embodiment, the compounds of the invention include compounds of Formula Ia,

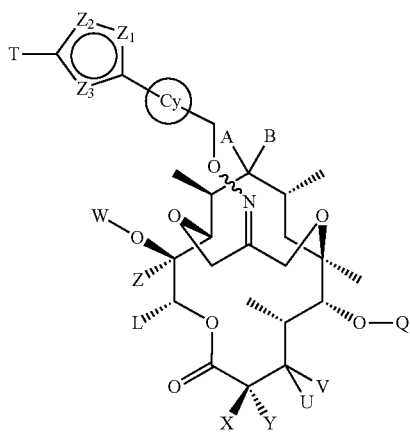
(Ia)

as well as the pharmaceutically acceptable salts, esters and prodrugs thereof, wherein:

T is hydrogen, OR$_3$, halogen or NR$_1$R$_2$, where R$_1$ and R$_2$ are each independently selected from:
(a) hydrogen;
(b) —R$_3$, where R$_3$ is substituted or unsubstituted —C$_1$-C$_6$ alkyl, —C$_2$-C$_6$ alkenyl, or —C$_2$-C$_6$ alkynyl each containing 0, 1, 2, or 3 heteroatoms selected from O, S or N;
(c) —C(O)R$_4$; where R$_4$ is independently selected from the group consisting of:
  (i) hydrogen;
  (ii) aryl; substituted aryl; heteroaryl; substituted heteroaryl;
  (iii) —R$_3$; and (iv) —$R_5$, where $R_5$ is substituted and unsubstituted —$C_3$-$C_{12}$ cycloalkyl each containing 0, 1, 2, or 3 heteroatoms selected from O, S or N;
(d) —C(O)NH$R_4$;
(e) —C(O)O$R_4$;
(f) an amino acid residue; and
(g) —S(O)$_2R_4$;

alternatively, $R_1$ and $R_2$ can be taken together with the nitrogen they are attached with to form a fused or non-fused, substituted or unsubstituted heterocyclic ring. $Z_1$ is N or $CR_{10}$, and $Z_2$ and $Z_3$ are each independently N, O, S or $CR_{10}$, where $R_{10}$ is independently selected from hydrogen, hydroxy, amino, halogen, substituted or unsubstituted alkoxy, substituted or unsubstituted alkylamino, substituted or unsubstituted dialkylamino, $CF_3$, CN, $NO_2$, $N_3$, sulfonyl, acyl, aliphatic, and substituted aliphatic; provided that at least two of $Z_1$, $Z_2$ and $Z_3$ are not $CR_{10}$. Cy is substituted or unsubstituted heterocyclic, or substituted or unsubstituted heteroaryl. A and B are each independently selected from:
(a) hydrogen;
(b) —$R_3$;
(c) —O$R_4$;
(d) —OC(O)$R_4$;
(e) —OC(O)NH$R_4$;
(f) —OC(O)O$R_4$;
(g) —N$R_8R_9$; where $R_8$ and $R_9$ are each independently selected from $R_3$; alternatively, $R_8$ and $R_9$ taken together with the nitrogen atom to which they are connected form a 3- to 10-membered ring which may optionally contain one or more heterofunctions selected from the group consisting of: —O—, —NH—, —N($C_1$-$C_6$-alkyl)-, —N($R_{10}$)—, —S(O)$_n$—, wherein n=0, 1 or 2, and $R_{10}$ is selected from aryl; substituted aryl; heteroaryl; and substituted heteroaryl;
(h) —NHC(O)$R_4$;
(i) —NHS(O$_2$)$R_4$;
(j) —NHC(O)O$R_4$; and
(k) —NHC(O)NH$R_4$;

Alternatively, A and B taken together with the carbon atom to which they are attached are selected from:
(a) C=O;
(b) C=N-J-$R_{11}$, where J is absent, O, C(O), SO$_2$, NH, NHC(O), NHC(O)NH or NHSO$_2$; and wherein $R_{11}$ is independently selected from halogen and $R_4$;
(c) C=CH-J-$R_{11}$;
(d) substituted or unsubstituted, and saturated or unsaturated 5- to 10-membered heterocyclic;

L is independently selected from $R_3$;
W is selected from:
(a) hydrogen;
(b) hydroxy prodrug group;
(c) —$R_3$;
(d) —C(O)$R_4$;
(e) —C(O)O—$R_4$; and
(f) —C(O)N($R_8R_9$);

Q is:
(a) —$R_4$;
(b) —C(O)$R_4$;
(c) —C(O)NH$R_4$;
(d) —C(O)O$R_4$;
(e) —S(O)$_2R_4$;
(f) monosaccharide;
(g) disaccharide; or
(h) trisaccharide;

Z is:
(a) hydrogen;
(b) —$N_3$;
(c) —CN;
(d) —$NO_2$;
(e) —C(O)NH$_2$;
(f) —C(O)OH;
(g) —CHO;
(h) —$R_3$;
(i) —C(O)O$R_3$;
(j) —C(O)$R_3$; or
(k) —C(O)N$R_8R_9$;

when U is hydrogen, V is selected from the group consisting of:
(a) hydrogen;
(b) —O$R_4$;
(c) —OC(O)$R_4$;
(d) —OC(O)NH$R_4$;
(e) —OS(O)$_2R_4$;
(f) —O-monosaccharide; and
(g) —O-disaccharide;

alternatively, U and V taken together with the carbon atom they are attached is C=O;

each of X and Y is independently:
(a) hydrogen;
(b) hydroxy;
(c) N$R_8R_9$;
(d) halogen; or
(e) —$R_3$.

Compounds of the invention further include compounds of Formula IX,

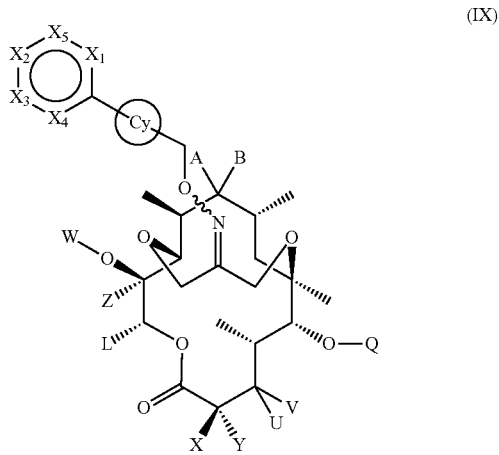

(IX)

as well as the pharmaceutically acceptable salts, esters and prodrugs thereof, wherein:
$X_1$, $X_2$, $X_3$, $X_4$, and $X_5$ are each independently selected from N or $CR_{10}$, where $R_{10}$ is independently selected from hydrogen, hydroxy, halogen, substituted or unsubstituted alkoxy, substituted or unsubstituted alkylamino, substituted or unsubstituted dialkylamino, $CF_3$, CN, $NO_2$, $N_3$, sulfonyl, acyl, aliphatic, substituted aliphatic or C—NH$R_1$, where $R_1$ is:
(a) hydrogen;
(b) —$R_3$, where $R_3$ is substituted or unsubstituted —$C_1$-$C_6$ alkyl, —$C_2$-$C_6$ alkenyl, or —$C_2$-$C_6$ alkynyl each containing 0, 1, 2, or 3 heteroatoms selected from O, S or N;
(c) —C(O)$R_4$; where $R_4$ is independently selected from the group consisting of:
(i) hydrogen;
(ii) aryl; substituted aryl; heteroaryl; substituted heteroaryl;
(iii) —$R_3$; and
(iv) —$R_5$, where $R_5$ is substituted and unsubstituted —$C_3$-$C_{12}$ cycloalkyl each containing 0, 1, 2, or 3 heteroatoms selected from O, S or N;

(d) —C(O)NHR$_4$;
(e) —C(O)OR$_4$;
(f) an amino acid residue; and
(g) —S(O)$_2$R$_4$;

provided that at least one of X$_1$ to X$_5$ is N and at least one of X$_1$-X$_5$ is C—R$_{10}$, wherein R$_{10}$ is NHR$_1$. Cy is selected from the group consisting of substituted or unsubstituted thiadiazole, oxadiazole, imidazole, thiazole, pyrazole, oxazole, amino pyridine, 2-pyridine where the six-membered ring is connected at 5-position, pyrimidine and pyrazine. Preferably Cy is oxazole or thiazole. A and B are each independently selected from:
(a) hydrogen;
(b) —R$_3$;
(c) —OR$_4$;
(d) —OC(O)R$_4$;
(e) —OC(O)NHR$_4$;
(f) —OC(O)OR$_4$;
(g) —NR$_8$R$_9$; where R$_8$ and R$_9$ are each independently selected from R$_3$; alternatively, R$_8$ and R$_9$ taken together with the nitrogen atom to which they are connected form a 3- to 10-membered ring which may optionally contain one or more heterofunctions selected from the group consisting of: —O—, —NH—, —N(C$_1$-C$_6$-alkyl)-, —N(R$_{10}$)—, —S(O)$_n$—, wherein n=0, 1 or 2, and R$_{10}$ is selected from aryl; substituted aryl; heteroaryl; and substituted heteroaryl;
(h) —NHC(O)R$_4$;
(i) —NHS(O)$_2$R$_4$;
(j) —NHC(O)OR$_4$; and
(k) —NHC(O)NHR$_4$;

Alternatively, A and B taken together with the carbon atom to which they are attached are selected from:
(a) C═O;
(b) C═N-J-R$_{11}$, where J is absent, O, CO, SO$_2$, NH, NH(CO), NH(CO)NH or NHSO$_2$; and wherein R$_{11}$ is independently selected from halogen and R$_4$;
(c) C═CH-J-R$_{11}$;
(d) substituted or unsubstituted, and saturated or unsaturated 5- to 10-membered heterocyclic;

L is independently selected from R$_3$;
W is selected from:
(a) hydrogen;
(b) hydroxy prodrug group;
(c) —R$_3$;
(d) —C(O)R$_4$;
(e) —C(O)O—R$_4$; and
(f) —C(O)N(R$_8$R$_9$);

Q is:
(a) —R$_4$;
(b) —C(O)R$_4$;
(c) —C(O)NHR$_4$;
(d) —C(O)OR$_4$;
(e) —S(O)$_2$R$_4$;
(f) monosaccharide;
(g) disaccharide; or
(h) trisaccharide;

Z is:
(a) hydrogen;
(b) —N$_3$;
(c) —CN;
(d) —NO$_2$;
(e) —C(O)NH$_2$;
(f) —C(O)OH;
(g) —CHO;
(h) —R$_3$;
(i) —C(O)OR$_3$;
(j) —C(O)R$_3$; or
(k) —C(O)NR$_8$R$_9$;

when U is hydrogen, V is selected from the group consisting of:
(a) hydrogen;
(b) —OR$_4$;
(c) —OC(O)R$_4$;
(d) —OC(O)NHR$_4$;
(e) —OS(O)$_2$R$_4$;
(f) —O-monosaccharide; and
(g) —O-disaccharide;

alternatively, U and V taken together with the carbon atom they are attached is C═O;
each of X and Y is independently:
(a) hydrogen;
(b) hydroxy;
(c) NR$_8$R$_9$;
(d) halogen; or
(e) —R$_3$.

In a preferred subset of the compounds of Formula IX, X$_4$ is N, X$_3$ is C—NH$_2$ and X$_1$, X$_2$ and X$_5$ are CH; or X$_4$ is C—NH$_2$, X$_3$ is N and X$_1$, X$_2$ and X$_5$ are CH; or X$_4$ and X$_2$ are N, X$_3$ and X$_5$ are C—NH$_2$ and X$_1$ is CH; or X$_4$ and X$_5$ are N, X$_3$ is C—NH$_2$ and X$_1$ and X$_2$ are C—H; or X$_4$ and X$_1$ are N, X$_3$ is C—NH$_2$ and X$_2$ and X$_5$ are CH; or X$_4$ is C—NH$_2$, X$_3$ and X$_1$ are N and X$_2$ and X$_5$ are CH.

The invention further provides compounds of the formula X:

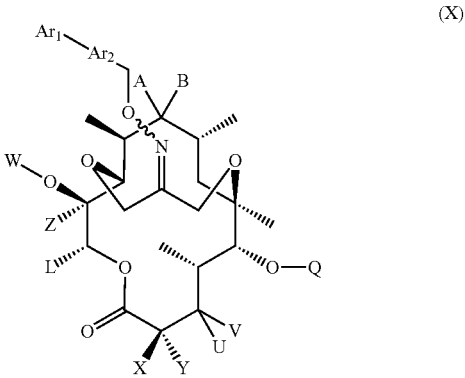

(X)

as well as the pharmaceutically acceptable salts, esters and prodrugs thereof, wherein:

Ar$_1$ is selected from substituted or unsubstituted amino thiazole, amino pyrazole, isoxazole, amino isoxazole, oxadiazole, amino oxadiazole, amino oxazole, 5-amino-1,2,4-thiadiazole, amino triazole, or amino tetrazole; and Ar$_2$ is selected from substituted or unsubstituted thiadiazole, oxadiazole, imidazole, thiazole, pyrazole, oxazole, phenyl, pyridine, amino pyridine, pyrimidine or pyrazine; or Ar$_1$ is selected from substituted or unsubstituted amino pyridine, amino pyrimidine or amino pyrazine; and Ar$_2$ is selected from substituted or unsubstituted thiadiazole, oxadiazole, imidazole, thiazole, pyrazole, oxazole, amino pyridine, 2-pyridine where Ar$_1$ is connected at 5-position, pyrimidine or pyrazine.

A and B are each independently selected from:
(a) hydrogen;
(b) —R$_3$ where R$_3$ is substituted or unsubstituted —C$_1$-C$_6$ alkyl, —C$_2$-C$_6$ alkenyl, or —C$_2$-C$_6$ alkynyl each containing 0, 1, 2, or 3 heteroatoms selected from O, S or N;
(c) —OR$_4$ where R$_4$ is independently selected from the group consisting of:

(i) hydrogen;
(ii) aryl; substituted aryl; heteroaryl; substituted heteroaryl;
(iii) —$R_3$; and
(iv) —$R_5$, where $R_5$ is substituted and unsubstituted —$C_3$-$C_{12}$ cycloalkyl each containing 0, 1, 2, or 3 heteroatoms selected from O, S or N;
(d) —OC(O)$R_4$;
(e) —OC(O)NH$R_4$;
(f) —OC(O)O$R_4$;
(g) —N$R_8R_9$; where $R_8$ and $R_9$ are each independently selected from $R_3$; alternatively, $R_8$ and $R_9$ taken together with the nitrogen atom to which they are connected form a 3- to 10-membered ring which may optionally contain one or more heterofunctions selected from the group consisting of: —O—, —NH—, —N($R_4$)—, —S(O)$_n$—, wherein n=0, 1 or 2;
(h) —NHC(O)$R_4$;
(i) —NHSO$_2R_4$;
(j) —NHC(O)O$R_4$; and
(k) —NHC(O)NH$R_4$;

Alternatively, A and B taken together with the carbon atom to which they are attached are selected from:
(a) C=O;
(b) C=N-J-$R_{11}$, where J is absent, O, C(O), SO$_2$, NH, NH(CO), NHC(O)NH or NHSO$_2$; and wherein $R_{11}$ is independently selected from halogen, NO$_2$ and $R_4$;
(c) C=CH-J-$R_{11}$;
(d) substituted or unsubstituted, and saturated or unsaturated 5- to 10-membered heterocyclic;

L is independently selected from $R_3$;
W is selected from:
(a) hydrogen;
(b) hydroxy prodrug group;
(c) —$R_3$;
(d) —C(O)$R_4$;
(e) —C(O)O—$R_4$; and
(f) —C(O)N($R_8R_9$);

Q is:
(a) —$R_4$;
(b) —C(O)$R_4$;
(c) —C(O)NH$R_4$;
(d) —C(O)O$R_4$;
(e) —S(O)$_2R_4$;
(f) monosaccharide;
(g) disaccharide; or
(h) trisaccharide;

Z is:
(a) hydrogen;
(b) —$N_3$;
(c) —CN;
(d) —NO$_2$;
(e) —C(O)NH$_2$;
(f) —C(O)OH;
(g) —CHO;
(h) —$R_3$;
(i) —C(O)O$R_3$;
(j) —C(O)$R_3$; or
(k) —C(O)N$R_8R_9$;

U is hydrogen, V is selected from the group consisting of:
(a) hydrogen;
(b) —O$R_4$;
(c) —OC(O)$R_4$;
(d) —OC(O)NH$R_4$;
(e) —OS(O)$_2R_4$;
(f) —O-monosaccharide; and
(g) —O-disaccharide;

Or alternatively, U and V taken together with the carbon atom they are attached is C=O;
each of X and Y is independently selected from:
(a) hydrogen;
(b) hydroxy;
(c) N$R_8R_9$;
(d) halogen; or
(e) —$R_3$,
provided that the compound is not

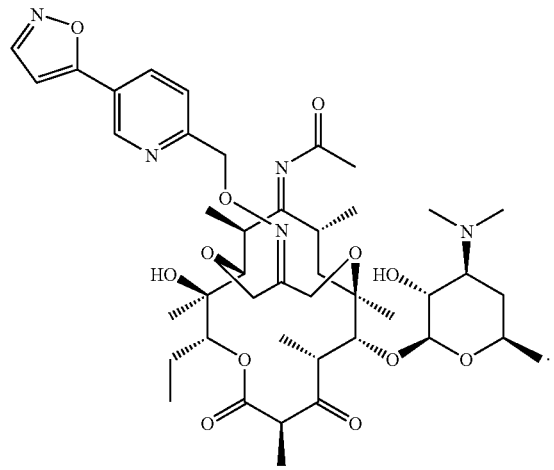 [SMILES: CC[C@H]1OC(=O)[C@H](C)C(=O)[C@H](C)[C@@H](O[C@@H]2O[C@H](C)C[C@H](N(C)C)[C@H]2O)[C@@]2(C)C[C@@H](C)/C(=N\C(C)=O)[C@H](C)[C@@H](OC/C(=N\OCc3ccc(-c4ccno4)cn3)CO2)[C@]1(C)O]

One preferred subset of compounds of Formula X are represented by formula (XI):

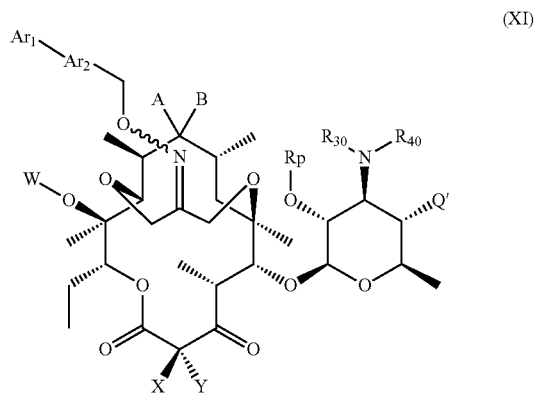

(XI)

as well as the pharmaceutically acceptable salts, esters and prodrugs thereof, wherein $R_p$ is hydrogen, hydroxy protected group or hydroxy prodrug group;

Q' is:
(a) hydrogen;
(b) O$R_p$; or
(c) —O$R_5$, where $R_5$ is selected from the group consisting of:
(i) —$R_3$; and
(ii) substituted and unsubstituted —$C_3$-$C_{12}$ cycloalkyl containing 0, 1, 2, or 3 heteroatoms selected from O, S or N;

$R_{30}$ and $R_{40}$ is independently selected from the group consisting of hydrogen, acyl, a substituted or unsubstituted, saturated or unsaturated aliphatic group, a substituted or unsubstituted, saturated or unsaturated alicyclic group, a substituted or unsubstituted aromatic group, a substituted or unsubstituted heteroaromatic group, saturated or unsaturated heterocyclic group; or can be taken together with the nitrogen atom to which they are attached to form a substituted or unsubstituted heterocyclic or heteroaromatic ring; and $Ar_1$, $Ar_2$, W, X, Y, A and B are as previously defined for Formula X. In one embodiment of the compounds of Formula XI, $Ar_1$ is aminopyrazole.

In one embodiment the compounds of the invention are represented by formula XII:

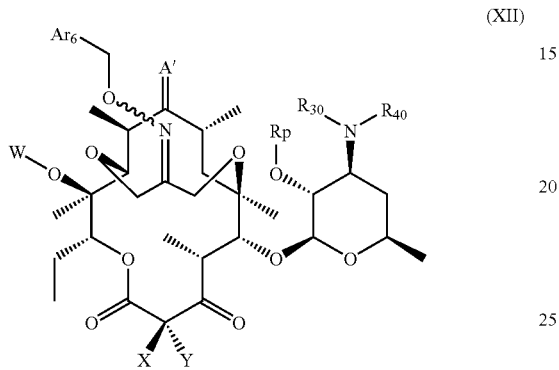

(XII)

as well as the pharmaceutically acceptable salts, esters and prodrugs thereof, wherein $R_p$, $R_{30}$, $R_{40}$, W, X and Y are as previously defined for Formulas X and $X_1$; A', together with the carbon atom to which it is attached, is selected from:

(a) C=O;
(b) C=N-J-$R_{11}$, where J is absent, O, C(O), $SO_2$, NH, NH(CO), NH(CO)NH or $NHSO_2$; and wherein $R_{11}$ is independently selected from halogen and $R_4$;
(c) C=CH-J-$R_{11}$;
(d) substituted or unsubstituted, and saturated or unsaturated 5- to 10-membered heterocyclic;

In one set of compounds of Formula XII, $Ar_6$ is selected from the groups set forth below and can be further substituted.

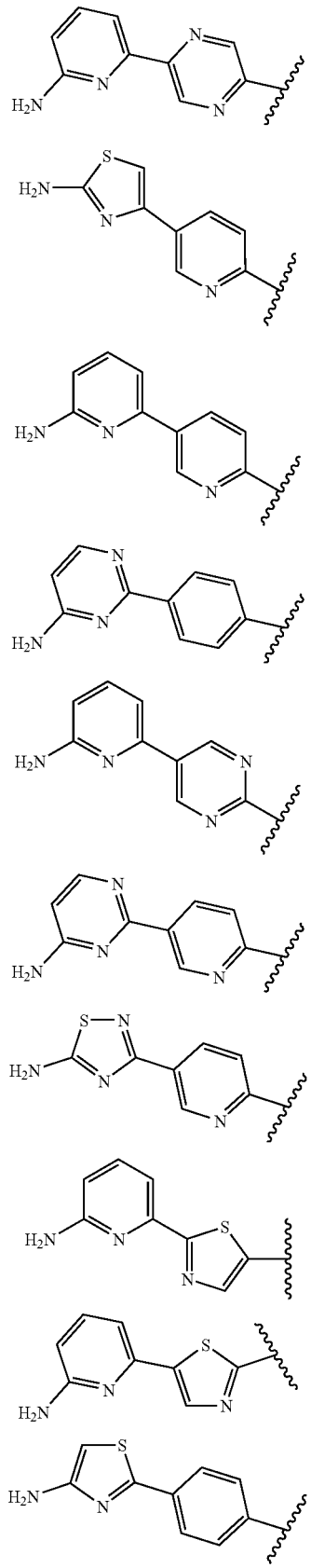

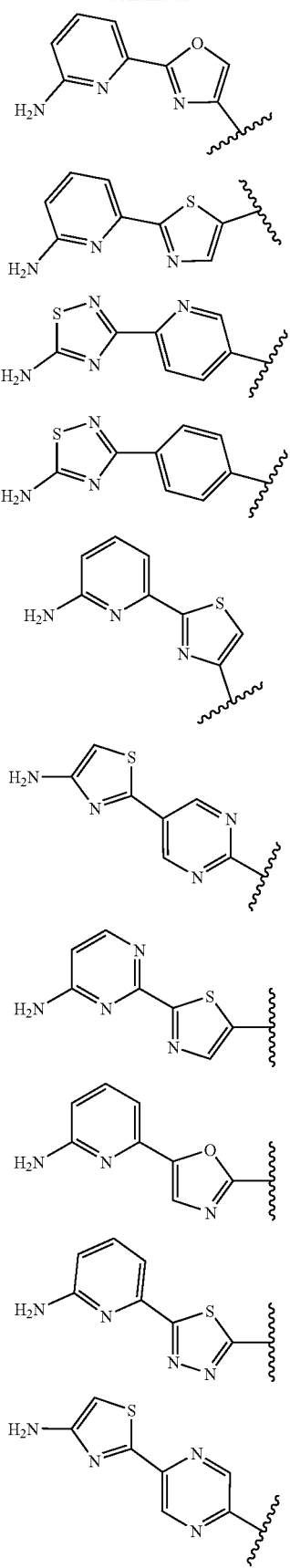
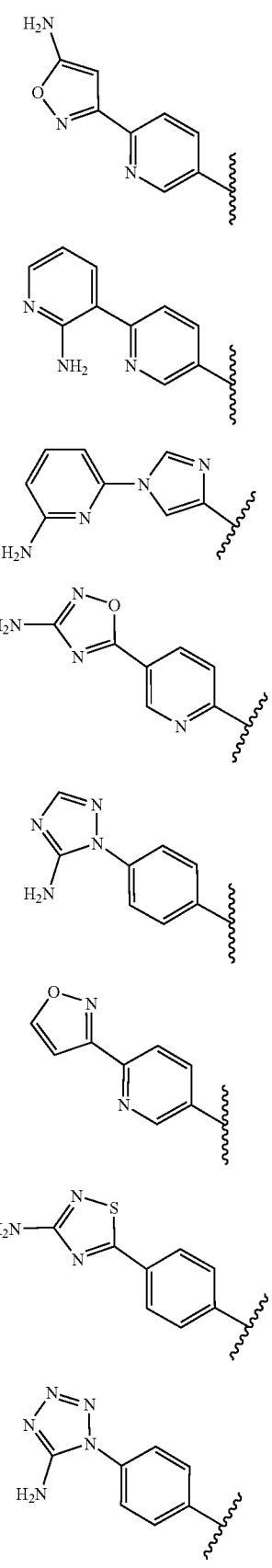

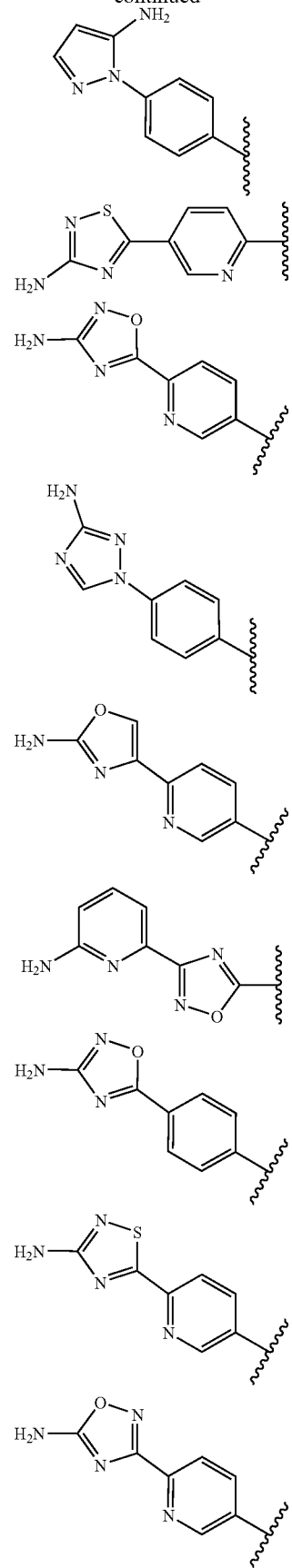
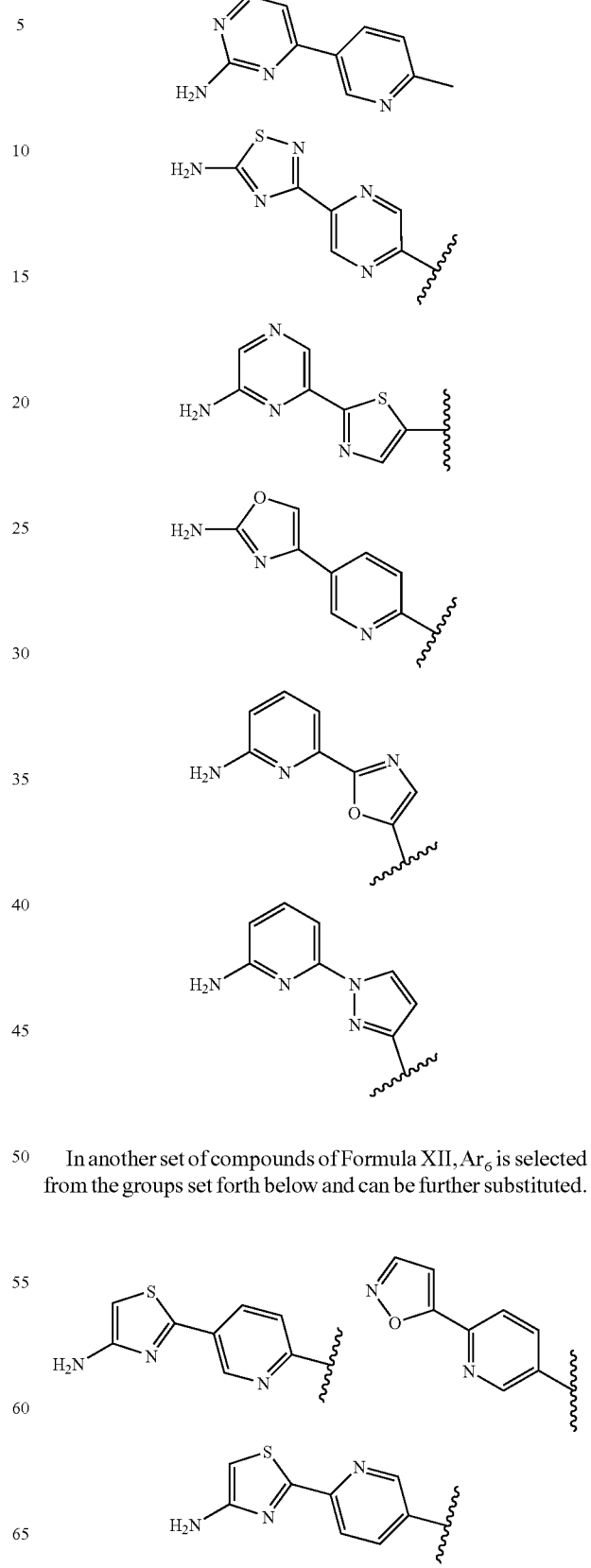
In another set of compounds of Formula XII, $Ar_6$ is selected from the groups set forth below and can be further substituted.

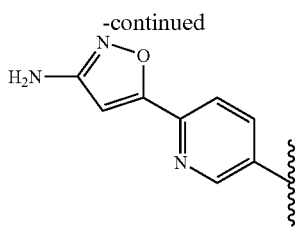

One subset of compounds of Formula X are represented by formula XIII:

(XIII)

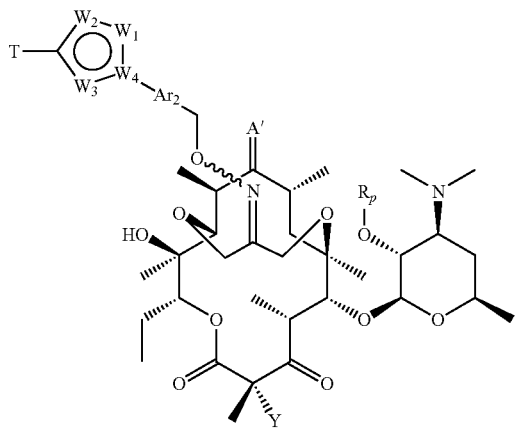

as well as the pharmaceutically acceptable salts, esters and prodrugs thereof, wherein A' is O or N(CO)$R_{11}$;
$R_p$ is hydrogen, hydroxy protected group or hydroxy prodrug group;
T is $NR_1R_2$, where $R_1$ and $R_2$ are each independently selected from:
  (a) hydrogen;
  (b) —$R_3$, where $R_3$ is substituted or unsubstituted —$C_1$-$C_6$ alkyl, —$C_2$-$C_6$ alkenyl, or —$C_2$-$C_6$ alkynyl each containing 0, 1, 2, or 3 heteroatoms selected from O, S or N;
  (c) —C(O)$R_4$; where $R_4$ is independently selected from the group consisting of:
    (i) hydrogen;
    (ii) aryl; substituted aryl; heteroaryl; substituted heteroaryl;
    (iii) —$R_3$; and
    (iv) —$R_5$, where $R_5$ is substituted and unsubstituted —$C_3$-$C_{12}$ cycloalkyl each containing 0, 1, 2, or 3 heteroatoms selected from O, S or N;
  (d) —C(O)NH$R_4$;
  (e) —C(O)O$R_4$;
  (f) an amino acid residue;
  (g) ($R_3$O)($R_4$O)P(O)—; and
  (h) —S(O)$_2R_4$;
alternatively, $R_1$ and $R_2$ can be taken together with the nitrogen they are attached with to form a fused or non-fused, substituted or unsubstituted heterocyclic ring;
$W_1$, $W_2$ and $W_3$ are each independently selected from S, N, O or C$R_{10}$ wherein $R_{10}$ is independently selected from hydrogen, hydroxy, amino, halogen, substituted or unsubstituted alkoxy, substituted or unsubstituted alkylamino, substituted or unsubstituted dialkylamino, $CF_3$, CN, $NO_2$, $N_3$, sulfonyl, acyl, aliphatic, and substituted aliphatic,
$W_4$ is N or C;
provided that $W_1$, $W_2$, $W_3$ and $W_4$ are selected such that the five-membered ring to which they belong is thiazole, pyrazole, isoxazole, oxadiazole, oxazole, 1,2,4-thiadiazole, triazole, or tetrazole; and
$Ar_2$, $R_{11}$ and Y are as previously defined for Formula X.

Another subset of compounds of Formula X are represented by formula (XIV):

(XIV)

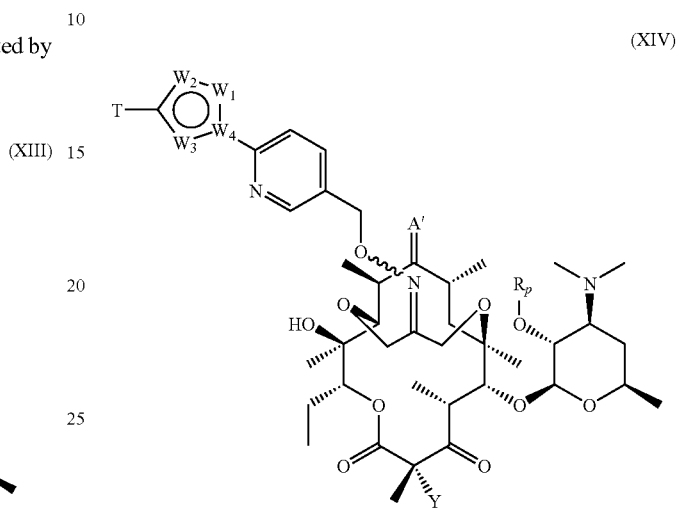

as well as the pharmaceutically acceptable salts, esters and prodrugs thereof, wherein A' is O or N(CO)$R_{11}$; $R_p$ is hydrogen, hydroxy protected group or hydroxy prodrug group; and T, $W_1$-$W_4$, $R_{11}$ and Y are as previously defined for Formula XIII.

Yet another subset of compounds of Formula X are represented by formula XV:

(XV)

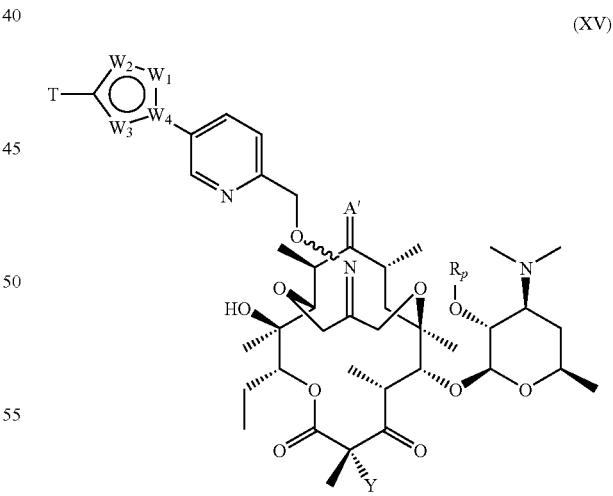

as well as the pharmaceutically acceptable salts, esters and prodrugs thereof, wherein A' is O or N(CO)$R_{11}$; $R_p$ is hydrogen, hydroxy protected group or hydroxy prodrug group; and T, $W_1$-$W_4$, $R_{11}$ and Y are as previously defined for Formula XIII.

In another embodiment of the present invention, there are disclosed compounds of formula XVI:

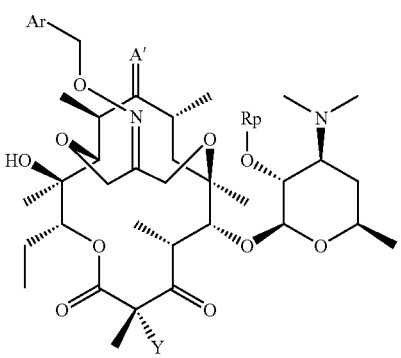

(XVI)

where Ar is selected from the group consisting of

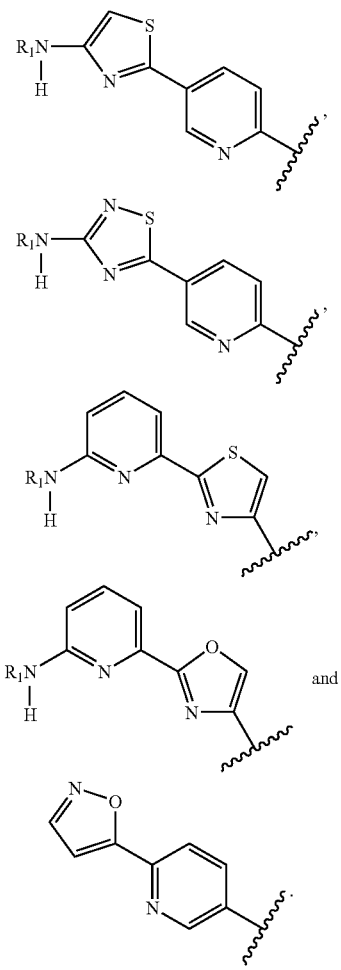

wherein A' is oxo or NC(O)R$_2$;

R$_1$ is hydrogen, —C(O)R$_2$ (preferably an amino acid residue) or (R$_3$O)(R$_4$O)P(O)—;

each R$_2$ is independently selected from hydrogen, substituted or unsubstituted alkyl, substituted or unsubstituted alkenyl, substituted or unsubstituted cycloalkyl or substituted or unsubstituted heterocycloalkyl;

each R$_3$ and R$_4$ is independently selected from hydrogen, substituted or unsubstituted alkyl or substituted or unsubstituted alkenyl;

Y is H or F; and R$_p$ is H or hydroxy protecting group.

The invention also contemplates pharmaceutically acceptable salts, esters and prodrugs of the compounds of formula X.

In a first preferred subset of compounds of Formula XVI, R$_1$ is hydrogen or an amino acid residue. In a second preferred subset of compounds of formula I, A' is oxo or NC(O)R$_2$, where R$_2$ is C$_1$-C$_6$-alkyl, preferably methyl, ethyl, propyl or isopropyl.

In one embodiment, R$_1$ is an amino acid residue of the formula:

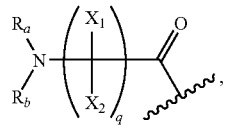

where q is an integer from 1 to 5; each X$_1$ and X$_2$ is, independently, hydrogen, alkyl, substituted alkyl, cycloalkyl, substituted cycloalkyl, heterocyloalkyl, substituted heteorcycloalkyl, heterocyloalkylalkyl, substituted heteocycloalkylalkyl, arylalkyl, substituted arylalkyl, heteroarylalkyl, substituted heteroarylalkyl, substituted cycloalkylalkyl or cycloalkylalkyl. R$_a$ and R$_b$ are each, independently, hydrogen, acyl (e.g., —C(O)R$_2$), alkyl, substituted alkyl, cycloalkyl, substituted cycloalkyl, hetroalkyl, substituted heteroalkyl, heterocyloalkyl, substituted heteorcycloalkyl, heterocyloalkylalkyl, substituted heteorcycloalkylalkyl, substituted cycloalkylalkyl, cycloalkylalkyl, arylalkyl, substituted arylalkyl, heteroarylalkyl or substituted heteroarylalkyl. Alternatively, when X$_2$ is hydrogen and q is 1, X$_1$ and R$_a$ can together form a C$_2$-C$_5$-alkylene group, or a C$_2$-C$_5$-alkenylene group.

In a preferred embodiment, R$_1$ is an α-amino acid residue, i.e., q is 1. More preferably, q is 1 and X$_1$ is hydrogen. Even more preferably, R$_1$ is selected from the group consisting of residues of glycine, D- and L-alanine, D- and L-phenylalanine, D- and L-tyrosine, D- and L-leucine, D- and L-isoleucine, D- and L-valine, D- and L-cysteine, D- and L-threonine, D- and L-serine, D- and L-arginine, D- and L-aspartic acid, D- and L-glutamic acid, D- and L-lysine, D- and L-histidine, D- and L-asparagine, D- and L-proline, D- and L-tryptophan, D- and L-glutamine, D- and L-methionine, D- and L-homoproline, D- and L-β-alanine, D- and L-norvaline, D- and L-norleucine, D- and L-cyclohexylalanine, D- and L-t-butylglycine, D- and L-4-hydroxyproline, D- and L-hydroxylysine, D- and L-demosine, D- and L-isodemosine, D- and L-3-methylhistidine, γ-aminobutyric acid, D- and L-citrulline, D- and L-homocysteine, D- and L-homoserine, D- and L-ornithine and D- and L-methionine sulfone. For chiral amino acid residues, the L-enantiomer is preferred.

In one preferred embodiment, R$_1$ is a residue of a naturally-occurring L-amino acid residue. Suitable residues of naturally occurring L-amino acid residues include, but are not limited to, those set forth below:

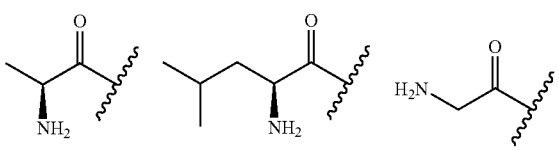

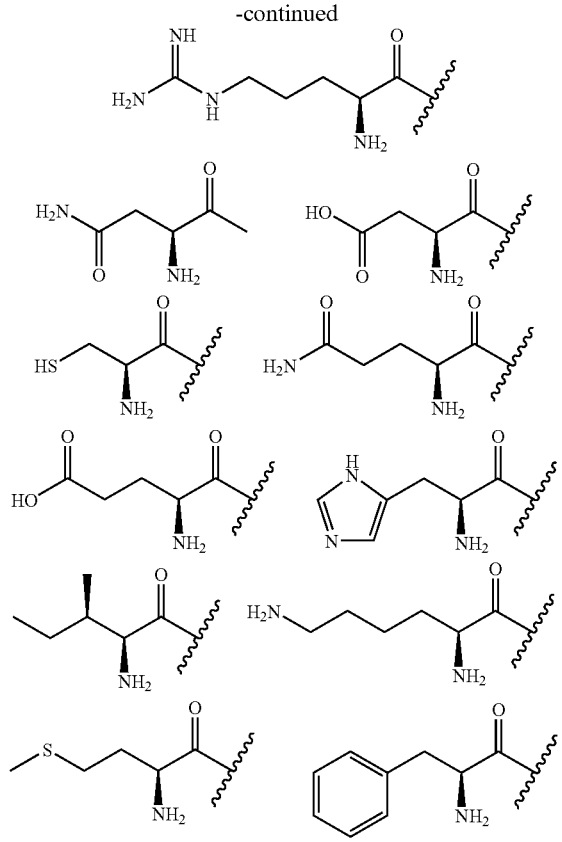
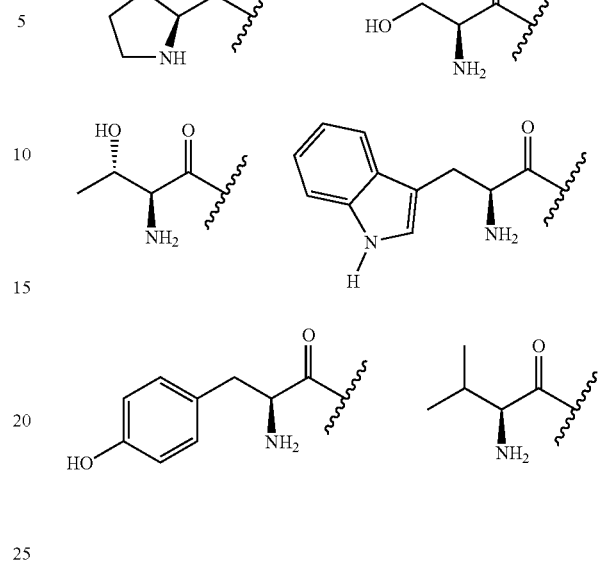

In a particularly preferred embodiment, $R_1$ is a residue of L-leucine of L-alanine.

Specific compounds of the invention include compounds 1-30 represented by formula XVI as set forth in Table 1 below, as well as pharmaceutically acceptable salts, esters and prodrugs of these compounds.

TABLE 1

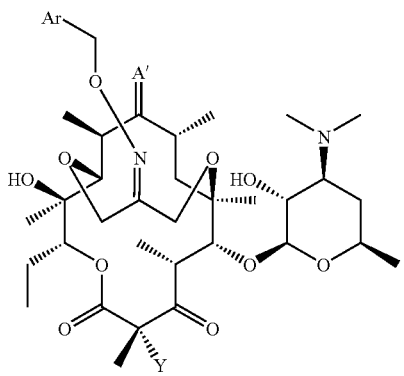

(XVI)

| Compound | Ar | Y | A' |
|---|---|---|---|
| 1 | (4-amino-thiazol-2-yl)-pyridin-2-yl | F | NC(O)Et |
| 2 | (3-amino-1,2,4-thiadiazol-5-yl)-pyridin-2-yl | F | O |

TABLE 1-continued
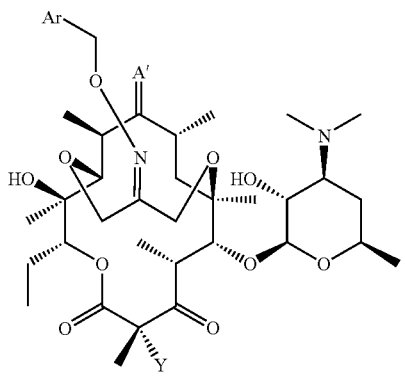
(XVI)
| Compound | Ar | Y | A' |
|---|---|---|---|
| 3 | 2-amino-pyridyl-thiazole | F | NC(O)Et |
| 4 | isoxazole-pyridyl | H | NC(O)Me |
| 5 | Ala-NH-thiazole-pyridyl | F | NC(O)Et |
| 6 | Leu-NH-thiazole-pyridyl | F | NC(O)Et |
| 7 | Ala-NH-pyridyl-thiazole | F | NC(O)Et |
| 8 | Leu-NH-pyridyl-thiazole | F | NC(O)Et |
| 9 | BnO(HO)P(O)NH-thiazole-pyridyl | F | NC(O)Et |

TABLE 1-continued
(XVI)
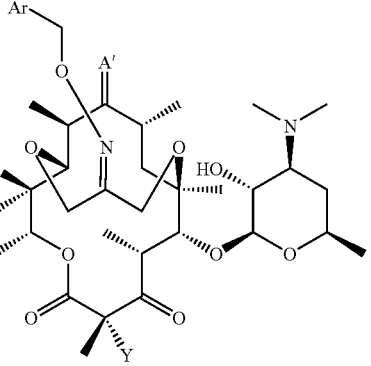
| Compound | Ar | Y | A' |
|---|---|---|---|
| 10 | 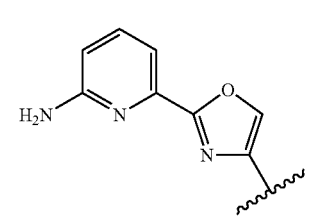 [SMILES: *c1coc(-c2cccc(N)n2)n1] | F | NC(O)Et |
| 11 | 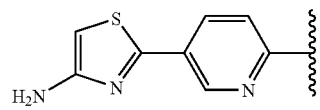 | F | NC(O)Et |
| 12 | 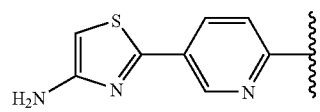 | F | NC(O)Et |
| 13 | 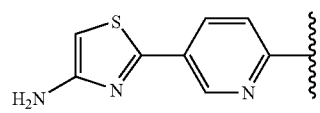 | F | NC(O)Me |
| 14 | 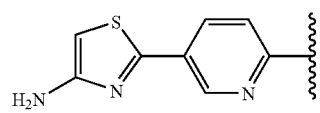 | H | NC(O)Me |
| 15 | 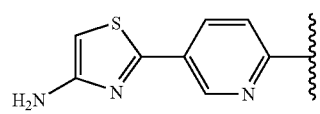 | F | NC(O)-isopropyl |
| 16 | 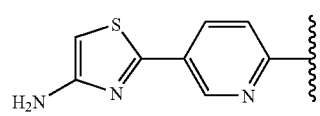 | H | O |
| 17 | 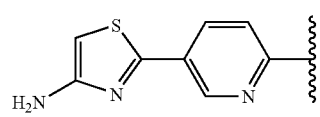 | F | O |
| 18 | 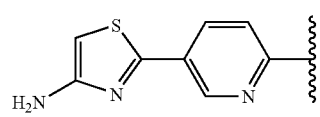 | F | NC(O)Et-$d_5$ |

TABLE 1-continued
(XVI)
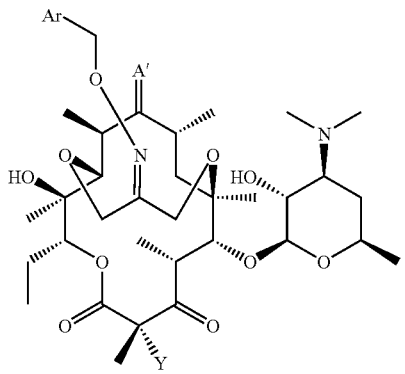
| Compound | Ar | Y | A' |
|---|---|---|---|
| 19 | 3-amino-1,2,4-thiadiazol-5-yl-pyridin-5-yl | F | NC(O)Et |
| 20 | 3-amino-1,2,4-thiadiazol-5-yl-pyridin-5-yl | H | NC(O)Me |
| 21 | 6-amino-pyridin-2-yl-thiazol-4-yl | H | O |
| 22 | 6-amino-pyridin-2-yl-thiazol-4-yl | F | NC(O)Me |
| 23 | 6-amino-pyridin-2-yl-thiazol-4-yl | F | NC(O)-isopropyl |
| 24 | 6-amino-pyridin-2-yl-thiazol-4-yl | F | O |
| 25 | isoxazol-5-yl-pyridin-5-yl | H | O |
| 26 | 6-amino-pyridazin-3-yl-oxazol-4-yl | F | NC(O)-isopropyl |

TABLE 1-continued

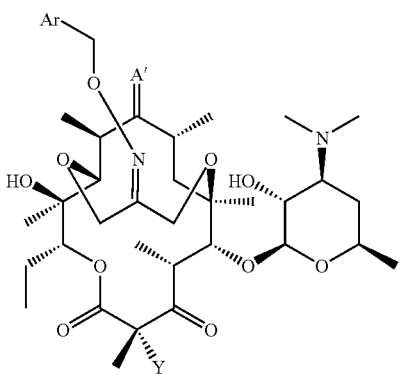

(XVI)

| Compound | Ar | Y | A' |
|---|---|---|---|
| 27 | 2-amino-6-(oxazol-2-yl)pyridine | F | NC(O)Me |
| 28 | 2-amino-6-(oxazol-2-yl)pyridine | H | NC(O)Me |
| 29 | 2-amino-6-(oxazol-2-yl)pyridine | H | O |
| 30 | 2-amino-6-(oxazol-2-yl)pyridine | H | C(O)H |

Additional representative compounds according to the invention are compounds of Formula XVI as set forth in Tables 2 to 6.

TABLE 2

| Ar | Y | A' |
|---|---|---|
| isoxazol-5-yl-pyridine | H | NC(O)Me |
| 3-amino-isoxazol-5-yl-pyridine | H | O |
| 3-amino-1,2,4-thiadiazol-5-yl-pyridine | H | O |
| 4-amino-thiazol-2-yl-pyridine | F | NC(O)Et |
| 4-amino-pyrimidin-2-yl-thiazole | H | O |

TABLE 2-continued

| Ar | Y | A' |
|---|---|---|
| [3-amino-1,2,4-thiadiazol-5-yl-pyridin-2-yl] | H | O |
| [4-amino-thiazol-2-yl-pyridin-2-yl] | F | NC(O)Et |

TABLE 3

| Ar | Y | A' |
|---|---|---|
| [6-amino-pyridin-2-yl-1,3,4-thiadiazol-2-yl] | F | NC(O)Me |
| [6-amino-pyridin-2-yl-imidazol-1-yl] | H | NC(O)Me |
| [3-amino-pyrazin-2-yl-thiazol-2-yl] | H | O |
| [isoxazol-5-yl-pyridin-2-yl] | H | O |
| [isoxazol-3-yl-pyridin-2-yl] | H | O |
| [3-amino-pyrazol-1-yl-pyridin-2-yl] | H | O |

TABLE 3-continued

| Ar | Y | A' |
|---|---|---|
| [5-amino-1,3,4-thiadiazol-2-yl-pyridin-3-yl] | H | O |
| [5-amino-isoxazol-3-yl-pyridin-2-yl] | H | NC(O)Me |
| [2-amino-pyridin-3-yl-pyridin-2-yl] | H | NC(O)Me |
| [5-amino-isoxazol-3-yl-pyridin-2-yl] | H | O |
| [2-amino-pyridin-3-yl-pyridin-2-yl] | H | O |
| [6-amino-pyridin-2-yl-pyridin-3-yl] | F | NH |
| [3-amino-pyrazol-1-yl-3-fluoro-phenyl] | F | O |

TABLE 3-continued

| Ar | Y | A' |
|---|---|---|
| 5-amino-1-phenyl-pyrazole (4-linked) | F | NC(O)Me |
| 3-amino-1-phenyl-pyrazole (4-linked) | F | O |
| 3-amino-5-(pyridin-2-yl)isoxazole | F | O |
| 5-amino-1-phenyl-1,2,4-triazole (4-linked) | F | NC(O)Me |
| 3-amino-1-phenyl-1,2,4-triazole (4-linked) | F | NC(O)Me |
| 6-amino-pyridin-3-yl-pyrimidine | F | NC(O)Me |
| 2,4-diamino-pyrimidine-6-(6-methylpyridin-3-yl) | F | NC(O)Me |
| 4-amino-2-(pyridin-5-yl)thiazole | H | O |
| 4-amino-2-(pyridin-5-yl)thiazole | F | O |
| 6-amino-2-(thiazol-5-yl)pyridine | H | O |
| 5-amino-3-(pyridin-5-yl)-1,2,4-thiadiazole | H | O |
| 6-amino-2-(thiazol-2-yl)pyridine | H | O |
| 6-amino-2-(thiazol-5-yl)pyridine | H | NC(O)Me |
| 3-amino-5-phenyl-1,2,4-oxadiazole | F | O |
| 6-amino-2-(oxazol-4-yl)pyridine | H | O |
| 6-amino-2-(oxazol-4-yl)pyridine | H | NC(O)Me |
| 6-amino-2-(thiazol-4-yl)pyridine | F | O |

TABLE 3-continued

| Ar | Y | A' |
|---|---|---|
| (3-amino-1,2,4-oxadiazol-5-yl)phenyl | H | O |
| (3-amino-1,2,4-oxadiazol-5-yl)pyridinyl | F | O |
| (3-amino-1,2,4-thiadiazol-5-yl)phenyl | H | O |
| (3-amino-1,2,4-oxadiazol-5-yl)pyridinyl | H | O |
| (5-amino-tetrazol-1-yl)phenyl | H | O |
| (5-amino-tetrazol-1-yl)phenyl (NH2 on tetrazole) | H | NC(O)Me |
| (5-amino-1,2,4-thiadiazol-3-yl)phenyl | H | NC(O)Me |
| (2-aminothiazol-4-yl)pyridinyl | H | O |

TABLE 3-continued

| Ar | Y | A' |
|---|---|---|
| (3-aminopyrazol-1-yl)pyridinyl | F | O |
| (6-aminopyridin-2-yl)pyrimidinyl | H | O |
| (3-amino-1,2,4-oxadiazol-5-yl)pyridinyl | H | O |
| (6-aminopyridin-2-yl)-1,2,4-oxadiazolyl | F | O |
| (6-aminopyridin-2-yl)-1,2,4-oxadiazolyl | H | O |
| (2-aminooxazol-4-yl)pyridinyl | H | O |
| (3-amino-1,2,4-thiadiazol-5-yl)phenyl | F | O |
| (6-aminopyridin-2-yl)pyrazolyl | F | NC(O)Et |

TABLE 3-continued
| Ar | Y | A' |
|---|---|---|
| 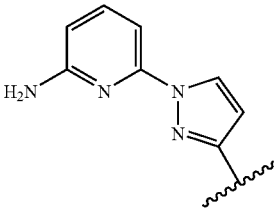 [SMILES: *c1ccn(-c2cccc(N)n2)n1] | H | O |
| 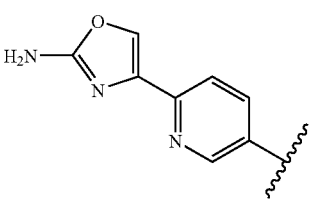 [SMILES: *c1ccc(-c2coc(N)n2)nc1] | H | O |
| 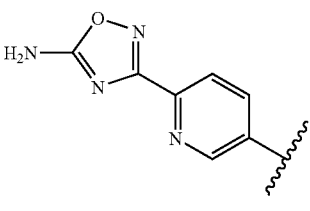 [SMILES: *c1ccc(-c2noc(N)n2)nc1] | H | O |
| 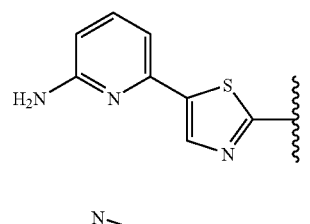 | H | O |
| 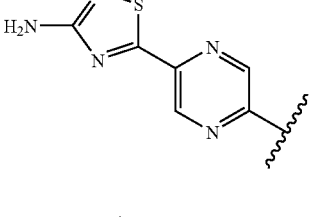 | F | O |
| 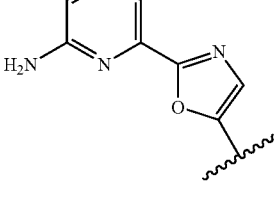 | F | NC(O)Et |
| 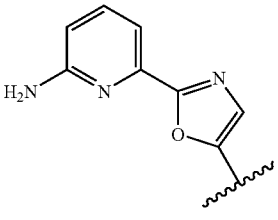 [SMILES: *c1cnc(-c2cccc(N)n2)o1] | H | O |
| 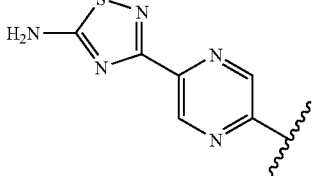 | F | NC(O)Et |
| 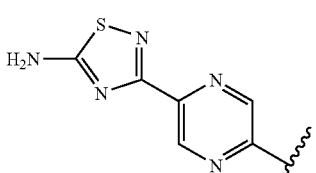 | H | O |
| 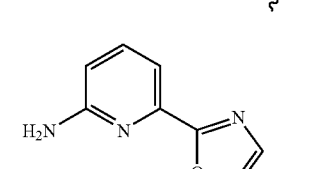 | H | NC(O)Me |
| 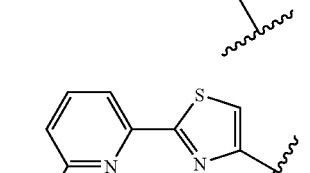 | H | O |
TABLE 4
| Ar | Y | A' |
|---|---|---|
| 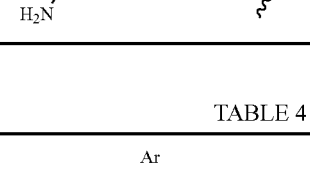 | F | NC(O)Et |
| 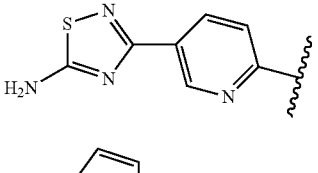 | F | NC(O)Me |
| 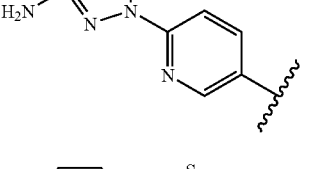 | F | NC(O)-isopropyl |
| 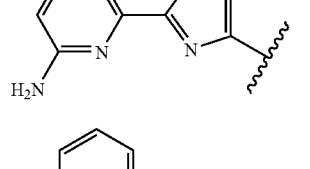 | F | NC(O)Me |

TABLE 4-continued
| Ar | Y | A' |
|---|---|---|
| 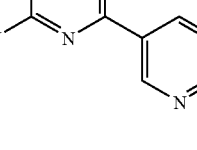 | F | NC(O)Et |
| 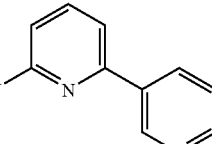 | F | NC(O)-propyl |
| 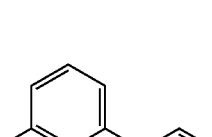 | F | NC(O)-cyclopropyl |
| 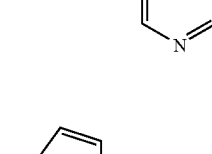 | F | NC(O)Et |
| 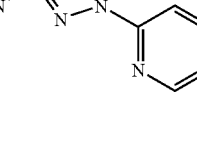 | F | NC(O)-isopropyl |
| 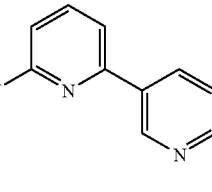 | F | NC(O)Me |
| 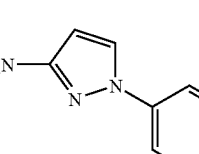 | F | NC(O)Me |
| 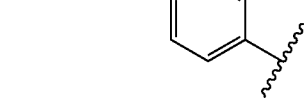 | H | NC(O)Et |
| 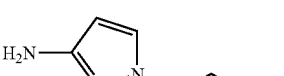 | H | NC(O)Me |
|  | F | NC(O)Me |
|  | F | NC(O)-isopropyl |
| 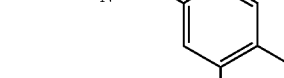 | F | NC(O)-isopropyl |
| 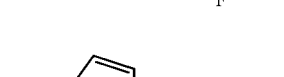 | H | NC(O)Me |
| 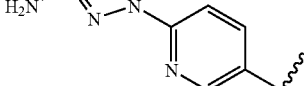 | F | NC(O)Me |

TABLE 4-continued
| Ar | Y | A' |
|---|---|---|
| 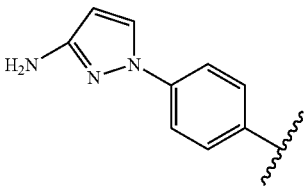 [SMILES: *c1ccc(-n2ccc(N)n2)cc1] | H | NC(O)-isopropyl |
| 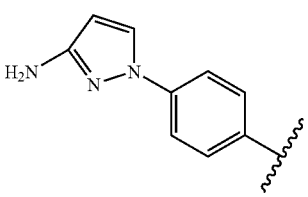 [SMILES: *c1ccc(-n2ccc(N)n2)cc1] | F | NC(O)-isopropyl |
| 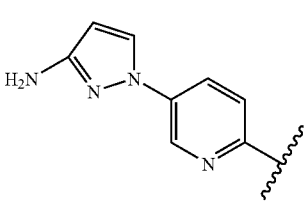 [SMILES: *c1ccc(-n2ccc(N)n2)cn1] | F | NC(O)Et |
| 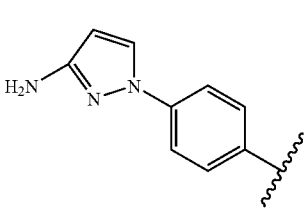 [SMILES: *c1ccc(-n2ccc(N)n2)cc1] | F | NC(O)-cyclopropyl |
| 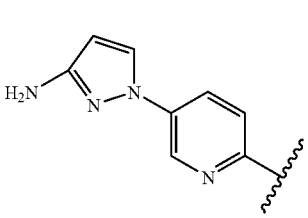 [SMILES: *c1ccc(-n2ccc(N)n2)cn1] | F | NC(O)-cyclopropyl |
| 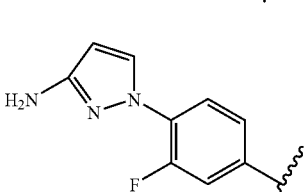 | F | NC(O)Me |
| 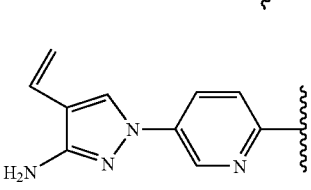 | F | NC(O)Me |
| 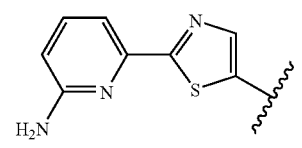 | F | NC(O)Me |
TABLE 4-continued
| Ar | Y | A' |
|---|---|---|
| 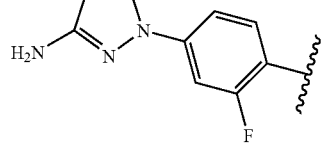 | H | NC(O)-isopropyl |
| 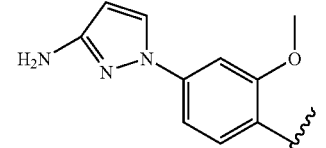 | F | NC(O)Me |
| 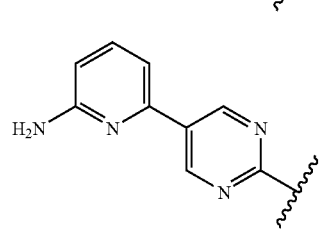 | F | NC(O)-isopropyl |
| 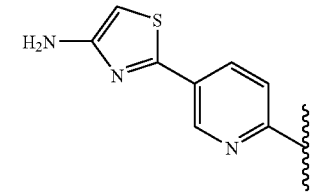 [SMILES: *c1ccc(-c2nc(N)cs2)cn1] | F | NC(O)Me |
| 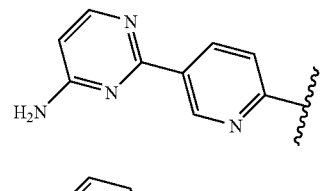 | F | NC(O)Me |
| 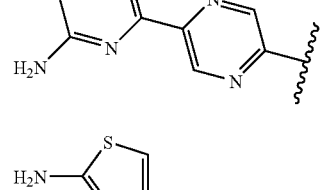 | F | NC(O)Me |
| 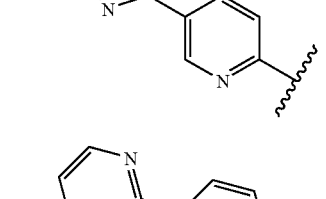 | F | NC(O)Me |
| 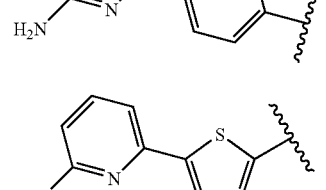 | F | NC(O)Me |

TABLE 4-continued
| Ar | Y | A' |
|---|---|---|
|  | F | NC(O)Me |
| 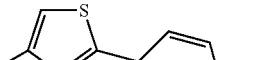 | H | NC(O)Me |
| 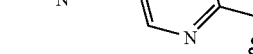 | F | NC(O)-isopropyl |
|  | F | NC(O)Et |
| 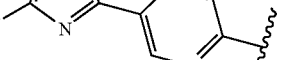 | F | NC(O)-isopropyl |
|  | F | NC(O)-cyclopropyl |
| 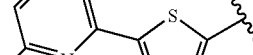 | F | NC(O)Et |
| 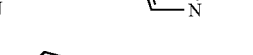 | F | NC(O)-isopropyl |
| 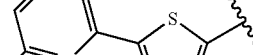 | F | NC(O)Et |
| 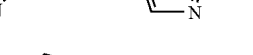 | F | NC(O)Et |
TABLE 4-continued
| Ar | Y | A' |
|---|---|---|
| 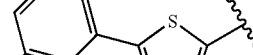 | F | NC(O)-isopropyl |
|  | F | NC(O)Et |
| 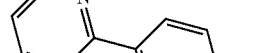 | F | NC(O)-isopropyl |
| 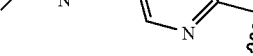 | H | NC(O)Et |
|  | F | NC(O)Et |
| 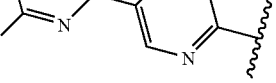 | H | NC(O)Et |
|  | F | NC(O)Et |
| 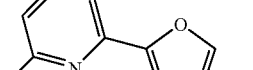 | F | NC(O)OMe |
|  | F | NC(O)Et |
|  | F | NC(O)Me |

TABLE 4-continued

| Ar | Y | A' |
|---|---|---|
| 5-amino-1,2,4-thiadiazol-3-yl-phenyl | F | NC(O)Et |
| 6-aminopyridin-2-yl-thiazol-5-yl | F | NC(O)Me |
| 5-amino-1,2,4-thiadiazol-3-yl-pyridin-5-yl | F | NC(O)Et |
| 5-amino-1,2,4-thiadiazol-3-yl-pyridin-5-yl | F | NC(O)-isopropyl |
| 4-aminopyrimidin-2-yl-thiazol-5-yl | F | NC(O)Et |
| 4-aminothiazol-2-yl-pyrimidin-2-yl | F | NC(O)Et |
| 4-aminothiazol-2-yl-pyrazin-5-yl | F | NC(O)Et |
| 6-aminopyridin-2-yl-oxazol-2-yl | F | NC(O)Et |
| 6-aminopyridin-2-yl-thiazol-4-yl | F | NC(O)Et |

TABLE 4-continued

| Ar | Y | A' |
|---|---|---|
| 4-aminothiazol-2-yl-pyridin-5-yl | F | NC(O)Et-d$_5$ |
| 6-aminopyrazin-2-yl-thiazol-4-yl | F | NC(O)Et |

TABLE 5

| Ar | Y | A' |
|---|---|---|
| 3-aminopyrazol-1-yl-pyridin-5-yl | H | O |
| 3-aminoisoxazol-5-yl-pyridin-5-yl | F | O |
| 5-amino-1,2,4-thiadiazol-3-yl-pyridin-5-yl | H | O |
| 6-aminopyridin-2-yl-oxazol-4-yl | H | O |
| 6-aminopyridin-2-yl-thiazol-4-yl | F | NC(O)Me |
| 6-aminopyridin-2-yl-pyrimidin-2-yl | H | O |

TABLE 5-continued

| Ar | Y | A' |
|---|---|---|
| (H2N-oxadiazole-pyridine structure) | H | O |
| (H2N-oxazole-pyridine structure) | H | O |
| (H2N-thiadiazole-pyridine structure) | F | NC(O)Et |

TABLE 6

| Ar | Y | A' |
|---|---|---|
| (lysine-amide-pyridine-thiazole structure) | F | NC(O)Et |
| (lysine-amide-pyridine-oxazole structure) | F | NC(O)Et |

A further embodiment of the present invention includes pharmaceutical compositions comprising any single compound delineated herein, or a pharmaceutically acceptable salt, ester, or prodrug thereof, with a pharmaceutically acceptable carrier or excipient.

Yet another embodiment of the present invention is a pharmaceutical composition comprising a combination of two or more compounds delineated herein, or a pharmaceutically acceptable salt, ester, or prodrug thereof, with a pharmaceutically acceptable carrier or excipient.

Yet a further embodiment of the present invention is a pharmaceutical composition comprising any single compound delineated herein in combination with one or more antibiotics known in the art (such as penicillin, amoxicillin, azithromycin, erythromycin, ciprofloxacin, telithromycin, cethromycin, and the like), or a pharmaceutically acceptable salt, ester, or prodrug thereof, with a pharmaceutically acceptable carrier or excipient.

In addition, the present invention contemplates processes of making any compound delineated herein via any synthetic method delineated herein.

DEFINITIONS

Listed below are definitions of various terms used to describe this invention. These definitions apply to the terms as they are used throughout this specification and claims, unless otherwise limited in specific instances, either individually or as part of a larger group.

The term "aryl," as used herein, refers to a mono- or polycyclic carbocyclic ring system including, but not limited to, phenyl, naphthyl, tetrahydronaphthyl, indanyl, idenyl.

The term "heteroaryl," as used herein, refers to a mono- or polycyclic aromatic radical having one or more ring atom selected from S, O and N; and the remaining ring atoms are carbon, wherein any N or S contained within the ring may be optionally oxidized. Heteroaryl includes, but is not limited to, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl.

In accordance with the invention, any of the aryls, substituted aryls, heteroaryls and substituted heteroaryls described herein, can be any aromatic group. Aromatic groups can be substituted or unsubstituted.

The terms "$C_1$-$C_8$ alkyl," or "$C_1$-$C_{12}$ alkyl," as used herein, refer to saturated, straight- or branched-chain hydrocarbon radicals containing between one and eight, or one and twelve carbon atoms, respectively. Examples of $C_1$-$C_8$ alkyl radicals include, but are not limited to, methyl, ethyl, propyl, isopropyl, n-butyl, tert-butyl, neopentyl, n-hexyl, heptyl and octyl radicals; and examples of $C_1$-$C_{12}$ alkyl radicals include, but are not limited to, ethyl, propyl, isopropyl, n-hexyl, octyl, decyl, dodecyl radicals. The term "alkylene" refers to an alkyl group from which an additional hydrogen atom has been removed to form a diradical group. Examples of $C_1$-$C_8$ alkylene radicals include, but are not limited to, methylene, ethylene, propylene, isopropylene, n-butylene, tert-butylene, neopentylene, n-hexylene, heptylene and octylene radicals; and examples of $C_1$-$C_{12}$ alkyl radicals include, but are not limited to, ethylene, propylene, isopropylene, n-hexylene, octylene, decylene, dodecylene radicals.

The term "$C_2$-$C_8$ alkenyl," as used herein, refer to straight- or branched-chain hydrocarbon radicals containing from two to eight carbon atoms having at least one carbon-carbon double bond by the removal of a single hydrogen atom. Alkenyl groups include, but are not limited to, for example, ethenyl, propenyl, butenyl, 1-methyl-2-buten-1-yl, heptenyl, octenyl, and the like. The term "alkenylene" refers to an alkenyl group from which an additional hydrogen atom has been removed to form a diradical group. Alkenylene groups include, but are not limited to, for example, ethenylene, propenylene, butenylene, 1-methyl-2-buten-1-ylene, heptenylene, octenylene, and the like.

The term "$C_2$-$C_8$ alkynyl," as used herein, refer to straight- or branched-chain hydrocarbon radicals containing from two to eight carbon atoms having at least one carbon-carbon triple bond by the removal of a single hydrogen atom. Representative alkynyl groups include, but are not limited to, for example, ethynyl, 1-propynyl, 1-butynyl, heptynyl, octynyl, and the like. The term "alkynylene" refers to an alkynyl group from which an additional hydrogen atom has been removed to form a diradical group. Alkynylene groups include, but are not limited to, for example, ethynylene, propynylene, butynylene, 1-methyl-2-butyn-1-ylene, heptynylene, octynylene, and the like.

The term "$C_3$-$C_8$-cycloalkyl", or "$C_3$-$C_{12}$-cycloalkyl," as used herein, refers to a monocyclic or polycyclic saturated carbocyclic ring compound. Examples of $C_3$-$C_8$-cycloalkyl include, but are not limited to, cyclopropyl, cyclobutyl, cyclopentyl, cyclohexyl, cycloheptyl and cyclooctyl; and examples of $C_3$-$C_{12}$-cycloalkyl include, but not limited to, cyclopropyl, cyclobutyl, cyclopentyl, cyclohexyl, bicyclo[2.2.1]heptyl, and bicyclo [2.2.2]octyl.

The term "$C_3$-$C_8$ cycloalkenyl", or "$C_3$-$C_{12}$ cycloalkenyl" as used herein, refers to monocyclic or polycyclic carbocyclic ring compound having at least one carbon-carbon double bond. Examples of $C_3$-$C_8$ cycloalkenyl include, but not limited to, cyclopropenyl, cyclobutenyl, cyclopentenyl, cyclohexenyl, cycloheptenyl, cyclooctenyl, and the like; and examples of $C_3$-$C_{12}$ cycloalkenyl include, but not limited to, cyclopropenyl, cyclobutenyl, cyclopentenyl, cyclohexenyl, cycloheptenyl, cyclooctenyl, and the like.

It is understood that any alkyl, alkenyl, alkynyl and cycloalkyl moiety described herein can also be an aliphatic group, an alicyclic group or a heterocyclic group. An "aliphatic" group is a non-aromatic moiety that may contain any combination of carbon atoms, hydrogen atoms, halogen atoms, oxygen, nitrogen or other atoms, and optionally contain one or more units of unsaturation, e.g., double and/or triple bonds. An aliphatic group may be straight chained, branched or cyclic and preferably contains between about 1 and about 24 carbon atoms, more typically between about 1 and about 12 carbon atoms. In addition to aliphatic hydrocarbon groups, aliphatic groups include, for example, polyalkoxyalkyls, such as polyalkylene glycols, polyamines, and polyimines, for example. Such aliphatic groups may be further substituted.

The term "alicyclic," as used herein, denotes a monovalent group derived from a monocyclic or bicyclic saturated carbocyclic ring compound by the removal of a single hydrogen atom. Examples include, but are not limited to, cyclopropyl, cyclobutyl, cyclopentyl, cyclohexyl, bicyclo[2.2.1]heptyl, and bicyclo[2.2.2]octyl. Such alicyclic groups may be further substituted.

The terms "heterocyclic" or "heterocycloalkyl" can be used interchangeably and referred to a non-aromatic ring or a bi- or tri-cyclic group fused system, where (i) each ring system contains at least one heteroatom independently selected from oxygen, sulfur and nitrogen, (ii) each ring system can be saturated or unsaturated (iii) the nitrogen and sulfur heteroatoms may optionally be oxidized, (iv) the nitrogen heteroatom may optionally be quaternized, (v) any of the above rings may be fused to an aromatic ring, and (yl) the remaining ring atoms are carbon atoms which may be optionally oxo-substituted. Representative heterocyclic groups include, but are not limited to, 1,3-dioxolane, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, quinoxalinyl, pyridazinonyl, and tetrahydrofuryl. Such heterocyclic groups may be further substituted.

The term "substituted" refers to substitution by independent replacement of one, two, or three or more of the hydrogen atoms thereon with substituents including, but not limited to deuterium, tritium, —F, —Cl, —Br, —I, —OH, protected hydroxy, —$NO_2$, —CN, —$NH_2$, protected amino, oxo, thioxo, —NH—$C_1$-$C_{12}$-alkyl, —NH—$C_2$-$C_8$-alkenyl, —NH—$C_2$-$C_8$-alkynyl, —NH—$C_3$-$C_{12}$-cycloalkyl, —NH-aryl, —NH-heteroaryl, —NH-heterocycloalkyl, -dialkylamino, -diarylamino, -diheteroarylamino, —O—$C_1$-$C_{12}$-alkyl, —O—$C_2$-$C_8$-alkenyl, —O—$C_2$-$C_8$-alkynyl, —O—$C_3$-$C_{12}$-cycloalkyl, —O-aryl, —O-heteroaryl, —O-heterocycloalkyl, —C(O)—$C_1$-$C_{12}$-alkyl, —C(O)—$C_2$-$C_8$-alkenyl, —C(O)—$C_2$-$C_8$-alkynyl, —C(O)—$C_3$-$C_{12}$-cycloalkyl, —C(O)-aryl, —C(O)-heteroaryl, —C(O)-heterocycloalkyl, —C(O)$NH_2$, —C(O)NH—$C_1$-$C_{12}$-alkyl, —C(O)NH—$C_2$-$C_8$-alkenyl, —C(O)NH—$C_2$-$C_8$-alkynyl, —C(O)NH—$C_3$-$C_{12}$-cycloalkyl, —C(O)NH-aryl, —C(O)NH-heteroaryl, —C(O)NH-heterocycloalkyl, —OC(O)$_2$—$C_1$-$C_{12}$-alkyl, —OC(O)$_2$—$C_2$-$C_8$-alkenyl, —OC(O)$_2$—$C_2$-$C_8$-alkynyl, —OC(O)$_2$—$C_3$-$C_{12}$-cycloalkyl, —OC(O)$_2$-aryl, —OC(O)$_2$-heteroaryl, —OC(O)$_2$-heterocycloalkyl, —OC(O)$NH_2$, —OC(O)NH—$C_1$-$C_{12}$-alkyl, —OC(O)NH—$C_2$-$C_8$-alkenyl, —OC(O)NH—$C_2$-$C_8$-alkynyl, —OC(O)NH—$C_3$-$C_{12}$-cycloalkyl, —OC(O)NH-aryl, —OC(O)NH-heteroaryl, —OC(O)NH— heterocycloalkyl, —NHC(O)—$C_1$-$C_{12}$-alkyl, —NHC(O)—$C_2$-$C_8$-alkenyl, —NHC(O)—$C_2$-$C_8$-alkynyl, —NHC(O)—$C_3$-$C_{12}$-cycloalkyl, —NHC(O)-aryl, —NHC(O)-heteroaryl, —NHC(O)-heterocycloalkyl, —NHC(O)$_2$—$C_1$-$C_{12}$-alkyl, —NHC(O)$_2$—$C_2$-$C_8$-alkenyl, —NHC(O)$_2$—$C_2$-$C_8$-alkynyl, —NHC(O)$_2$—$C_3$-$C_{12}$-cycloalkyl, —NHC(O)$_2$-aryl, —NHC(O)$_2$-heteroaryl, —NHC(O)$_2$— heterocycloalkyl, —NHC(O)$NH_2$, —NHC(O)NH—$C_1$-$C_{12}$-alkyl, —NHC(O)NH—$C_2$-$C_8$-alkenyl, —NHC(O)NH—$C_2$-$C_8$-alkynyl, —NHC(O)NH—$C_3$-$C_{12}$-cycloalkyl, —NHC(O)NH-aryl, —NHC(O)NH-heteroaryl, —NHC(O)NH-heterocycloalkyl, NHC(S)$NH_2$, —NHC(S)NH—$C_1$-$C_{12}$-alkyl, —NHC(S)NH—$C_2$-$C_8$-alkenyl, —NHC(S)NH—$C_2$-$C_8$-alkynyl, —NHC(S)NH—$C_3$-$C_{12}$-cycloalkyl, —NHC(S)NH-aryl, —NHC(S)NH-heteroaryl, —NHC(S)NH-heterocycloalkyl, —NHC(NH)$NH_2$, —NHC(NH)NH—$C_1$-$C_{12}$-alkyl, —NHC(NH)NH—$C_2$-$C_8$-alkenyl, —NHC(NH)NH—$C_2$-$C_8$-alkynyl, —NHC(NH)NH—$C_3$-$C_{12}$-cycloalkyl, —NHC(NH)NH-aryl, —NHC(NH)NH-heteroaryl, —NHC(NH)NH-heterocycloalkyl, —NHC(NH)—$C_1$-$C_{12}$-alkyl, —NHC(NH)—$C_2$-$C_8$-alkenyl, —NHC(NH)—$C_2$-$C_8$-alkynyl, —NHC(NH)—$C_3$-$C_{12}$-cycloalkyl, —NHC(NH)-aryl, —NHC(NH)-heteroaryl, —NHC(NH)-heterocycloalkyl, —C(NH)NH—$C_1$-$C_{12}$-alkyl, —C(NH)NH—$C_2$-$C_8$-alkenyl, —C(NH)NH—$C_2$-$C_8$-alkynyl, —C(NH)NH—$C_3$-$C_{12}$-cycloalkyl, —C(NH)NH-aryl, —C(NH)NH-heteroaryl, —C(NH)NH-heterocycloalkyl, —S(O)—$C_1$-$C_{12}$-alkyl, —S(O)—$C_2$-$C_8$-alkenyl, —S(O)—$C_2$-$C_8$-alkynyl, —S(O)—$C_3$-$C_{12}$-cycloalkyl, —S(O)-aryl, —S(O)-heteroaryl, —S(O)-heterocycloalkyl —$SO_2NH_2$, —$SO_2$NH—$C_1$-$C_{12}$-alkyl, —$SO_2$NH—$C_2$-$C_8$-alkenyl, —$SO_2$NH—$C_2$-$C_8$-alkynyl, —SO$_2$NH—C$_3$-C$_{12}$-cycloalkyl, —SO$_2$NH-aryl, —SO$_2$NH-heteroaryl, —SO$_2$NH-heterocycloalkyl, —NHSO$_2$—C$_1$-C$_{12}$-alkyl, —NHSO$_2$—C$_2$-C$_8$-alkenyl, —NHSO$_2$—C$_2$-C$_8$-alkynyl, —NHSO$_2$—C$_3$-C$_{12}$-cycloalkyl, —NHSO$_2$-aryl, —NHSO$_2$-heteroaryl, —NHSO$_2$-heterocycloalkyl, —CH$_2$NH$_2$, —CH$_2$SO$_2$CH$_3$, -aryl, -arylalkyl, -heteroaryl, -heteroarylalkyl, -heterocycloalkyl, —C$_3$-C$_{12}$-cycloalkyl, polyalkoxyalkyl, polyalkoxy, -methoxymethoxy, -methoxyethoxy, —SH, —S—C$_1$-C$_{12}$-alkyl, —S—C$_2$-C$_8$-alkenyl, —S—C$_2$-C$_8$-alkynyl, —S—C$_3$-C$_{12}$-cycloalkyl, —S-aryl, —S-heteroaryl, —S-heterocycloalkyl, or methylthiomethyl. It is understood that the aryls, heteroaryls, alkyls, and the like can be further substituted.

The term "monosaccharide" embraces radicals of cladinose, allose, altrose, arabinose, erythrose, erythrulose, fructose, D-fucitol, L-fucitol, fucosamine, fucose, galactosamine, D-galactosaminitol, galactose, glucosamine, glucosaminitol, glucose, glyceraldehyde, glycerol, glycerone, gulose, idose, lyxose, mannosamine, annose, psicose, quinovose, quinovosamine, rhamnitol, rhamnosamine, rhamnose, ribose, ribulose, sorbose, tagatose, tartaric acid, threose, xylose and xylulose. The monosaccharide may further be a deoxy sugar (alcoholic hydroxy group replaced by hydrogen), amino sugar (alcoholic hydroxy group replaced by amino group), a thio sugar (alcoholic hydroxy group replaced by thiol, or C=O replaced by C=S, or a ring oxygen of cyclic form replaced by sulfur), a seleno sugar, a telluro sugar, an aza sugar (ring carbon replaced by nitrogen), an imino sugar (ring oxygen replaced by nitrogen), a phosphano sugar (ring oxygen replaced with phosphorus), a phospha sugar (ring carbon replaced with phosphorus), a C-substituted monosaccharide (hydrogen at a non-terminal carbon atom replaced with carbon), an unsaturated monosaccharide, an alditol (carbonyl group replaced with CHOH group), aldonic acid (aldehydic group replaced by carboxy group), a ketoaldonic acid, a uronic acid, an aldaric acid, and so forth. Amino sugars include amino monosaccharides, preferably galactosamine, glucosamine, mannosamine, fucosamine, quinovosamine, neuraminic acid, muramic acid, lactosediamine, acosamine, bacillosamine, daunosamine, desosamine, forosamine, garosamine, kanosamine, kansosamine, mycaminose, mycosamine, perosamine, pneumosamine, purpurosamine, rhodosamine. It is understood that the monosaccharide and the like can be further substituted.

The terms "disaccharide", "trisaccharide" and "polysaccharide" embrace radicals of abequose, amicetose, amylose, apiose, arcanose, ascarylose, ascorbic acid, boivinose, cellobiose, cellotriose, chacotriose, chalcose, colitose, cymarose, 2-deoxyribose, 2-deoxyglucose, diginose, digitalose, digitoxose, evalose, evemitrose, gentianose, gentiobiose, hamamelose, inulin, isolevoglucosenone, isomaltose, isomaltotriose, isopanose, kojibiose, lactose, lactosamine, lactosediamine, laminarabiose, levoglucosan, levoglucosenone, β-maltose, manninotriose, melezitose, melibiose, muramic acid, mycarose, mycinose, neuraminic acid, nigerose, nojirimycin, noviose, oleandrose, panose, paratose, planteose, primeverose, raffinose, rhodinose, rutinose, sarmentose, sedoheptulose, sedoheptulosan, solatriose, sophorose, stachyose, streptose, sucrose, α,α-trehalose, trehalosamine, turanose, tyvelose, umbelliferose and the like. Further, it is understood that the "disaccharide", "trisaccharide" and "polysaccharide" and the like can be further substituted. Disaccharide also includes amino sugars and their derivatives, particularly a mycaminose derivatized at the C-4' position or a 4 deoxy-3-amino-glucose derivatized at the C-6' position.

The term "trisaccharide" includes amino sugars and halo sugars, where halo sugars is saccharide group having at least one halogen substituent.

The term "halogen," as used herein, refers to an atom selected from fluorine, chlorine, bromine and iodine.

The term "hydroxy activating group", as used herein, refers to a labile chemical moiety which is known in the art to activate a hydroxyl group so that it will depart during synthetic procedures such as in a substitution or an elimination reaction. Examples of hydroxyl activating group include, but not limited to, mesylate, tosylate, triflate, p-nitrobenzoate, phosphonate and the like.

The term "activated hydroxy", as used herein, refers to a hydroxy group activated with a hydroxyl activating group, as defined above, including mesylate, tosylate, triflate, p-nitrobenzoate, phosphonate groups, for example.

The term "hydroxy protecting group," as used herein, refers to a labile chemical moiety which is known in the art to protect a hydroxyl group against undesired reactions during synthetic procedures. After said synthetic procedure(s) the hydroxy protecting group as described herein may be selectively removed. Hydroxy protecting groups as known in the art are described generally in T. H. Greene and P. G. M. Wuts, *Protective Groups in Organic Synthesis,* 3rd edition, John Wiley & Sons, New York (1999). Examples of hydroxyl protecting groups include benzyloxycarbonyl, 4-nitrobenzyloxycarbonyl, 4-bromobenzyloxycarbonyl, 4-methoxybenzyloxycarbonyl, methoxycarbonyl, tert-butoxycarbonyl, isopropoxycarbonyl, diphenylmethoxycarbonyl, 2,2,2-trichloroethoxycarbonyl, 2-(trimethylsilyl)ethoxycarbonyl, 2-furfuryloxycarbonyl, allyloxycarbonyl, acetyl, formyl, chloroacetyl, trifluoroacetyl, methoxyacetyl, phenoxyacetyl, benzoyl, methyl, t-butyl, 2,2,2-trichloroethyl, 2-trimethylsilyl ethyl, 1,1-dimethyl-2-propenyl, 3-methyl-3-butenyl, allyl, benzyl, para-methoxybenzyldiphenylmethyl, triphenylmethyl (trityl), tetrahydrofuryl, methoxymethyl, methylthiomethyl, benzyloxymethyl, 2,2,2-triehloroethoxymethyl, 2-(trimethylsilyl)ethoxymethyl, methanesulfonyl, para-toluenesulfonyl, trimethylsilyl, triethylsilyl, triisopropylsilyl, and the like. Preferred hydroxyl protecting groups for the present invention are acetyl (Ac or —C(O)CH$_3$), benzoyl (Bz or —C(O)C$_6$H$_5$), and trimethylsilyl (TMS or —Si(CH$_3$)$_3$).

The term "protected hydroxy," as used herein, refers to a hydroxy group protected with a hydroxy protecting group, as defined above, including benzoyl, acetyl, trimethylsilyl, triethylsilyl, methoxymethyl groups, for example.

The term "hydroxy prodrug group", as used herein, refers to a promoiety group which is known in the art to change the physicochemical, and hence the biological properties of a parent drug in a transient manner by covering or masking the hydroxy group. After said synthetic procedure(s), the hydroxy prodrug group as described herein must be capable of reverting back to hydroxy group in vivo. Hydroxy prodrug groups as known in the art are described generally in Kenneth B. Sloan, *Prodrugs, Topical and Ocular Drug Delivery,* (Drugs and the Pharmaceutical Sciences; Volume 53), Marcel Dekker, Inc., New York (1992).

The term "amino protecting group," as used herein, refers to a labile chemical moiety which is known in the art to protect an amino group against undesired reactions during synthetic procedures. After said synthetic procedure(s) the amino protecting group as described herein may be selectively removed. Amino protecting groups as known in the art are described generally in T. H. Greene and P. G. M. Wuts, *Protective Groups in Organic Synthesis,* 3rd edition, John Wiley & Sons, New York (1999). Examples of amino protecting groups include, but are not limited to, t-butoxycarbonyl, 9-fluorenylmethoxycarbonyl, benzyloxycarbonyl, and the like.

The term "leaving group" means a functional group or atom which can be displaced by another functional group or atom in a substitution reaction, such as a nucleophilic substitution reaction. By way of example, representative leaving groups include chloro, bromo and iodo groups; sulfonic ester groups, such as mesylate, tosylate, brosylate, nosylate and the like; and acyloxy groups, such as acetoxy, trifluoroacetoxy and the like.

The term "protected amino," as used herein, refers to an amino group protected with an amino protecting group as defined above.

The term "aprotic solvent," as used herein, refers to a solvent that is relatively inert to proton activity, i.e., not acting as a proton-donor. Examples include, but are not limited to, hydrocarbons, such as hexane and toluene, for example, halogenated hydrocarbons, such as, for example, methylene chloride, ethylene chloride, chloroform, and the like, heterocyclic compounds, such as, for example, tetrahydrofuran and N-methylpyrrolidinone, and ethers such as diethyl ether, bis-methoxymethyl ether. Such compounds are well known to those skilled in the art, and it will be obvious to those skilled in the art that individual solvents or mixtures thereof may be preferred for specific compounds and reaction conditions, depending upon such factors as the solubility of reagents, reactivity of reagents and preferred temperature ranges, for example. Further discussions of aprotic solvents may be found in organic chemistry textbooks or in specialized monographs, for example: *Organic Solvents Physical Properties and Methods of Purification*, 4th ed., edited by John A. Riddick et al, Vol. II, in the *Techniques of Chemistry Series*, John Wiley & Sons, NY, 1986.

The term "protic solvent' as used herein, refers to a solvent that tends to provide protons, such as an alcohol, for example, methanol, ethanol, propanol, isopropanol, butanol, t-butanol, and the like. Such solvents are well known to those skilled in the art, and it will be obvious to those skilled in the art that individual solvents or mixtures thereof may be preferred for specific compounds and reaction conditions, depending upon such factors as the solubility of reagents, reactivity of reagents and preferred temperature ranges, for example. Further discussions of protogenic solvents may be found in organic chemistry textbooks or in specialized monographs, for example: *Organic Solvents Physical Properties and Methods of Purification*, 4th ed., edited by John A. Riddick et al., Vol. II, in the *Techniques of Chemistry Series*, John Wiley & Sons, NY, 1986.

Combinations of substituents and variables envisioned by this invention are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., therapeutic or prophylactic administration to a subject).

The synthesized compounds can be separated from a reaction mixture and further purified by a method such as column chromatography, high pressure liquid chromatography, or recrystallization. As can be appreciated by the skilled artisan, further methods of synthesizing the compounds of the formulae herein will be evident to those of ordinary skill in the art. Additionally, the various synthetic steps may be performed in an alternate sequence or order to give the desired compounds. Synthetic chemistry transformations and protecting group methodologies (protection and deprotection) useful in synthesizing the compounds described herein are known in the art and include, for example, those such as described in R. Larock, *Comprehensive Organic Transformations*, VCH Publishers (1989); T. W. Greene and P. G. M. Wuts, *Protective Groups in Organic Synthesis,* 2d. Ed., John Wiley and Sons (1991); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995), and subsequent editions thereof.

The term "subject" as used herein refers to an animal. Preferably the animal is a mammal. More preferably the mammal is a human. A subject also refers to, for example, dogs, cats, horses, cows, pigs, guinea pigs, fish, birds and the like.

The compounds of this invention may be modified by appending appropriate functionalities to enhance selective biological properties. Such modifications are known in the art and may include those which increase biological penetration into a given biological system (e.g., blood, lymphatic system, central nervous system), increase oral availability, increase solubility to allow administration by injection, alter metabolism and alter rate of excretion.

The compounds described herein contain one or more asymmetric centers and thus give rise to enantiomers, diastereomers, and other stereoisomeric forms that may be defined, in terms of absolute stereochemistry, as (R)- or (S)-, or as (D)- or (L)- for amino acids. The present invention is meant to include all such possible isomers, as well as their racemic and optically pure forms. Optical isomers may be prepared from their respective optically active precursors by the procedures described above, or by resolving the racemic mixtures. The resolution can be carried out in the presence of a resolving agent, by chromatography or by repeated crystallization or by some combination of these techniques which are known to those skilled in the art. Further details regarding resolutions can be found in Jacques, et al., *Enantiomers, Racemates, and Resolutions* (John Wiley & Sons, 1981). When the compounds described herein contain olefinic double bonds, other unsaturation, or other centers of geometric asymmetry, and unless specified otherwise, it is intended that the compounds include both E and Z geometric isomers or cis- and trans-isomers. Likewise, all tautomeric forms are also intended to be included. The configuration of any carbon-carbon double bond appearing herein is selected for convenience only and is not intended to designate a particular configuration unless the text so states; thus a carbon-carbon double bond or carbon-heteroatom double bond depicted arbitrarily herein as trans may be cis, trans, or a mixture of the two in any proportion.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describes pharmaceutically acceptable salts in detail in J. Pharmaceutical Sciences, 66: 1-19 (1977). The salts can be prepared in situ during the final isolation and purification of the compounds of the invention, or separately by reacting the free base function with a suitable organic acid. Examples of pharmaceutically acceptable include, but are not limited to, nontoxic acid addition salts are salts of an amino group formed with inorganic acids such as hydrochloric acid, hydrobromic acid, phosphoric acid, sulfuric acid and perchloric acid or with organic acids such as acetic acid, maleic acid, tartaric acid, citric acid, lactobionic acid, succinic acid or malonic acid or by using other methods used in the art such as ion exchange. Other pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, alkyl having from 1 to 6 carbon atoms, sulfonate and aryl sulfonate.

As used herein, the term "pharmaceutically acceptable ester" refers to esters which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include, but are not limited to, formates, acetates, propionates, butyrates, acrylates and ethylsuccinates.

The term "pharmaceutically acceptable prodrugs" as used herein refers to those prodrugs of the compounds of the present invention which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the present invention. "Prodrug", as used herein means a compound which is convertible in vivo by metabolic means (e.g. by hydrolysis) to a compound of Formula I. Various forms of prodrugs are known in the art, for example, as discussed in Bundgaard, (ed.), Design of Prodrugs, Elsevier (1985); Widder, et al. (ed.), Methods in Enzymology, vol. 4, Academic Press (1985); Krogsgaard-Larsen, et al., (ed). "Design and Application of Prodrugs, Textbook of Drug Design and Development, Chapter 5, 113-191 (1991); Bundgaard, et al., Journal of Drug Deliver Reviews, 8:1-38 (1992); Bundgaard, J. of Pharmaceutical Sciences, 77:285 et seq. (1988); Higuchi and Stella (eds.) Prodrugs as Novel Drug Delivery Systems, American Chemical Society (1975); and Bernard Testa & Joachim Mayer, "Hydrolysis In Drug And Prodrug Metabolism: Chemistry, Biochemistry And Enzymology," John Wiley and Sons, Ltd. (2002).

The present invention also relates to solvates of the compounds of the invention, for example hydrates.

This invention also encompasses pharmaceutical compositions containing, and methods of treating bacterial infections through administering, pharmaceutically acceptable prodrugs of compounds of the formula I. For example, compounds of formula I having free amino, amido, hydroxy or carboxylic groups can be converted into prodrugs. Prodrugs include compounds wherein an amino acid residue, or a polypeptide chain of two or more (e.g., two, three or four) amino acid residues is covalently joined through an amide or ester bond to a free amino, hydroxy or carboxylic acid group of compounds of formula I. The amino acid residues include but are not limited to the 20 naturally occurring amino acids commonly designated by three letter symbols and also includes 4-hydroxyproline, hydroxyysine, demosine, isodemosine, 3-methylhistidine, norvalin, beta-alanine, gamma-aminobutyric acid, citrulline, homocysteine, homoserine, ornithine and methionine sulfone. Additional types of prodrugs are also encompassed. For instance, free carboxyl groups can be derivatized as amides or alkyl esters. Free hydroxy groups may be derivatized using groups including but not limited to hemisuccinates, ethyl succinate, phosphate esters, dimethylaminoacetates, and phosphoryloxymethyloxycarbonyls, as outlined in Advanced Drug Delivery Reviews, 1996, 19, 115. Carbamate prodrugs of hydroxy and amino groups are also included, as are carbonate prodrugs, sulfonate esters and sulfate esters of hydroxy groups. Derivatization of hydroxy groups as (acyloxy)methyl and (acyloxy)ethyl ethers wherein the acyl group may be an alkyl ester, optionally substituted with groups including but not limited to ether, amine and carboxylic acid functionalities, or where the acyl group is an amino acid ester as described above, are also encompassed. Prodrugs of this type are described in J. Med. Chem. 1996, 39, 10. Free amines can also be derivatized as amides, sulfonamides or phosphonamides. All of these prodrug moieties may incorporate groups including but not limited to ether, amine and carboxylic acid functionalities.

As used herein, unless otherwise indicated, the term "bacterial infection(s)" or "protozoa infections"; includes, but is not limited to, bacterial infections and protozoa infections that occur in mammals, fish and birds as well as disorders related to bacterial infections and protozoa infections that may be treated or prevented by administering antibiotics such as the compounds of the present invention. Such bacterial infections and protozoa infections and disorders related to such infections include, but are not limited to, the following: pneumonia, otitis media, meningitis, sinusitus, bronchitis, tonsillitis, cystic fibrosis (CF) and mastoiditis related to infection by *Streptococcus pneumoniae, Haemophilus influenzae, Moraxella catarrhalis, Staphylococcus aureus, Peptostreptococcus* spp, or *Pseudomonas* spp.; pharyngitis, rheumatic fever, and glomerulonephritis related to infection by *Streptococcus pyogenes*, Groups C and G streptococci, *Clostridium diptheriae*, or *Actinobacillus haemolyticum*; respiratory tract infections related to infection by *Mycoplasma pneumoniae, Legionella pneumophila, Streptococcus pneumoniae, Haemophilus influenzae*, or *Chlamydia pneumoniae*; uncomplicated skin and soft tissue infections, abscesses and osteomyelitis, and puerperal fever related to infection by *Staphylococcus aureus*, coagulase-positive staphylococci (i.e., *S. epidermidis, S. hemolyticus*, etc.), *S. pyogenes, S. agalactiae*, Streptococcal groups C-F (minute-colony streptococci), viridans streptococci, *Corynebacterium* spp., *Clostridium* spp., or *Bartonella henselae*; uncomplicated acute urinary tract infections related to infection by *S. saprophyticus* or *Enterococcus* spp.; urethritis and cervicitis; and sexually transmitted diseases related to infection by

*Chlamydia trachomatis, Haemophilus ducreyi, Treponema pallidum, Ureaplasma urealyticum,* or *Nesseria gonorrheae*; toxin diseases related to infection by *S. aureus* (food poisoning and Toxic shock syndrome), or Groups A, S, and C streptococci; ulcers related to infection by *Helicobacter pylori*; systemic febrile syndromes related to infection by *Borrelia recurrentis*; Lyme disease related to infection by *Borrelia burgdorferi*; conjunctivitis, keratitis, and dacrocystitis related to infection by *C. trachomatis, N. gonorrhoeae, S. aureus, S. pneumoniae, S. pyogenes, H. influenzae,* or *Listeria* spp.; disseminated *Mycobacterium avium* complex (MAC) disease related to infection by *Mycobacterium avium,* or *Mycobacterium intracellulare*; gastroenteritis related to infection by *Campylobacter jejuni*; intestinal protozoa related to infection by *Cryptosporidium* spp. odontogenic infection related to infection by viridans streptococci; persistent cough related to infection by *Bordetella pertussis*; gas gangrene related to infection by *Clostridium perfringens* or *Bacteroides* spp.; Skin infection by *S. aureus, Propionibacterium* acne; atherosclerosis related to infection by *Helicobacter pylori* or *Chlamydia pneumoniae*; or the like.

Bacterial infections and protozoa infections and disorders related to such infections that may be treated or prevented in animals include, but are not limited to, the following: bovine respiratory disease related to infection by *P. haemolytica., P. multocida, Mycoplasma bovis,* or *Bordetella* spp.; cow enteric disease related to infection by *E. coli* or protozoa (i.e., coccidia, cryptosporidia, etc.), dairy cow mastitis related to infection by *S. aureus, S. uberis, S. agalactiae, S. dysgalactiae, Klebsiella* spp., *Corynebacterium,* or *Enterococcus* spp.; swine respiratory disease related to infection by *A. pleuropneumoniae., P. multocida,* or *Mycoplasma* spp.; swine enteric disease related to infection by *E. coli, Lawsonia intracellularis, Salmonella* spp., or *Serpulina hyodyisinteriae*; cow footrot related to infection by *Fusobacterium* spp.; cow metritis related to infection by *E. coli*; cow hairy warts related to Infection by *Fusobacterium necrophorum* or *Bacteroides nodosus*; cow pink-eye related to infection by *Moraxella bovis*, cow premature abortion related to infection by protozoa (i.e. neosporium); urinary tract infection in dogs and cats related to infection by *E. coli*; skin and soft tissue infections in dogs and cats related to infection by *S. epidermidis, S. intermedius,* coagulase neg. *Staphylococcus* or *P. multocida*; and dental or mouth infections in dogs and oats related to infection by *Alcaligenes* spp., *Bacteroides* spp., *Clostridium* spp., *Enterobacter* spp., *Eubacterium* spp., *Peptostreptococcus* spp., *Porphfyromonas* spp., *Campylobacter* spp., *Actinomyces* spp., *Erysipelothrix* spp., *Rhodococcus* spp., *Trypanosoma* spp., *Plasmodium* spp., *Babesia* spp., *Toxoplasma* spp., *Pneumocystis* spp., *Leishmania* spp., and *Trichomonas* spp. or *Prevotella* spp. Other bacterial infections and protozoa infections and disorders related to such infections that may be treated or prevented in accord with the method of the present invention are referred to in J. P. Sanford at al., "The Sanford Guide To Antimicrobial Therapy," 26th Edition, (Antimicrobial Therapy, Inc., 1996).

Antibacterial Activity

Susceptibility tests can be used to quantitatively measure the in vitro activity of an antimicrobial agent against a given bacterial isolate. Compounds are tested for in vitro antibacterial activity by a micro-dilution method. Minimal Inhibitory Concentration (MIC) is determined in 96 well microtiter plates utilizing the appropriate broth medium for the observed bacterial isolates. Antimicrobial agents are serially diluted (2-fold) in DMSO to produce a concentration range from about 64 µg/ml to about 0.03 µg/ml. The diluted compounds (2 µl/well) are then transferred into sterile, uninoculated medium (0.2 mL) by use of a 96 fixed tip-pipetting station. The inoculum for each bacterial strain is standardized to approximately $5 \times 10^5$ CFU/mL by optical comparison to a 0.5 McFarland turbidity standard. The plates are inoculated with 10 µl/well of adjusted bacterial inoculum. The 96 well plates are covered and incubated at 35+/−2° C. for 24 hours in ambient air environment. Following incubation, plate wells are visually examined by Optical Density measurement for the presence of growth (turbidity). The lowest concentration of an antimicrobial agent at which no visible growth occurs is defined as the MIC. The compounds of the invention generally demonstrated an MIC in the range from about 64 µg/ml to about 0.03 µg/ml.

All in vitro testing follows the guidelines described in the Approved Standards M7-A7 protocol, published by the Clinical Laboratory Standards Institute (CLSI).

The invention further provides compositions and methods of treating patients suffering from an inflammatory condition comprising administering to a patient in need thereof, a therapeutically effective amount of at least one compound of the invention. Specific examples of inflammatory conditions treatable according to the invention include, but are not limited to, scleritis; epi-scleritis; allergic conjunctivitis; pulmonary inflammatory diseases, particularly cystic fibrosis (CF), asthma, chronic obstructive pulmonary disease (COPD), allergic bronchopulmonary aspergillosis (ABPA), and sarcoidosis; procto-sigmoiditis; allergic rhinitis; arthritis; tendonitis; apthous stomatitis; and inflammatory bowel disease.

The invention further provides compositions and methods for i) prophylactic treatment of those patients susceptible to the symptoms CF including pulmonary infection and inflammation associated with CF, ii) treatment at the initial onset of symptoms of pulmonary infection and inflammation associated with CF, and iii) treatment of ongoing or relapsing symptoms of infection and inflammation associated with CF. In accordance with the invention a compound according to any one of compounds of the invention, is administered to a patient in need of treatment for CF, in amount sufficient to prevent, diminish or eradicate symptoms of CF including chronic pulmonary inflammation and infection.

Pharmaceutical Compositions

The pharmaceutical compositions of the present invention comprise a therapeutically effective amount of a compound of the present invention formulated together with one or more pharmaceutically acceptable carriers or excipients.

As used herein, the term "pharmaceutically acceptable carrier or excipient" means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols such as propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The pharmaceutical compositions of this invention may be administered orally, parenterally, by inhalation spray, topically, rectally, nasally, buccally, vaginally or via an implanted reservoir, preferably by oral administration or administration by injection. The pharmaceutical compositions of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intraarticular, intraarterial, intrasynovial, intrasternal, intrathecal, intralesional and intracranial injection or infusion techniques.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions, may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or: a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

For pulmonary delivery, a therapeutic composition of the invention is formulated and administered to the patient in solid or liquid particulate form by direct administration e.g., inhalation into the respiratory system. Solid or liquid particulate forms of the active compound prepared for practicing the present invention include particles of respirable size: that is, particles of a size sufficiently small to pass through the mouth and larynx upon inhalation and into the bronchi and alveoli of the lungs. Delivery of aerosolized therapeutics, particularly aerosolized antibiotics, is known in the art (see, for example U.S. Pat. No. 5,767,068 to VanDevanter et al., U.S. Pat. No. 5,508,269 to Smith et al, and WO 98/43650 by Montgomery, all of which are incorporated herein by reference). A discussion of pulmonary delivery of antibiotics is also found in U.S. Pat. No. 6,014,969, incorporated herein by reference.

According to the methods of treatment of the present invention, bacterial infections, cystic fibrosis and inflammatory conditions are treated or prevented in a patient such as a human or another animal by administering to the patient a therapeutically effective amount of a compound of the invention, in such amounts and for such time as is necessary to achieve the desired result.

By a "therapeutically effective amount" of a compound of the invention is meant an amount of the compound which confers a therapeutic effect on the treated subject, at a reasonable benefit/risk ratio applicable to any medical treatment. The therapeutic effect may be objective (i.e., measurable by some test or marker) or subjective (i.e., subject gives an indication of or feels an effect). An effective amount of the compound described above may range from about 0.1 mg/Kg to about 500 mg/Kg, preferably from about 1 to about 50 mg/Kg. Effective doses will also vary depending on route of administration, as well as the possibility of co-usage with other agents. It will be understood, however, that the total daily usage of the compounds and compositions of the present invention will be decided by the attending physician within the scope of sound medical judgment. The specific therapeutically effective dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or contemporaneously with the specific compound employed; and like factors well known in the medical arts.

The total daily dose of the compounds of this invention administered to a human or other animal in single or in divided doses can be in amounts, for example, from 0.01 to 50 mg/kg body weight or more usually from 0.1 to 25 mg/kg body weight. Single dose compositions may contain such amounts or submultiples thereof to make up the daily dose. In general, treatment regimens according to the present invention comprise administration to a patient in need of such treatment from about 10 mg to about 1000 mg of the compound(s) of this invention per day in single or multiple doses.

The compounds of the formulae described herein can, for example, be administered by injection, intravenously, intraarterially, subdermally, intraperitoneally, intramuscularly, or subcutaneously; or orally, buccally, nasally, transmucosally, topically, in an ophthalmic preparation, or by inhalation, with a dosage ranging from about 0.1 to about 500 mg/kg of body weight, alternatively dosages between 1 mg and 1000 mg/dose, every 4 to 120 hours, or according to the requirements of the particular drug. The methods herein contemplate administration of an effective amount of compound or compound composition to achieve the desired or stated effect. Typically, the pharmaceutical compositions of this invention will be administered from about 1 to about 6 times per day or alternatively, as a continuous infusion. Such administration can be used as a chronic or acute therapy. The amount of active ingredient that may be combined with pharmaceutically exipients or carriers to produce a single dosage form will vary depending upon the host treated and the particular mode of administration. A typical preparation will contain from about 5% to about 95% active compound (w/w). Alternatively, such preparations may contain from about 20% to about 80% active compound.

Lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the disease, condition or symptoms, the patient's disposition to the disease, condition or symptoms, and the judgment of the treating physician.

Upon improvement of a patient's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level. Patients may, however, require intermittent treatment on a long-term basis upon any recurrence of disease symptoms.

When the compositions of this invention comprise a combination of a compound of the formulae described herein and one or more additional therapeutic or prophylactic agents, both the compound and the additional agent should be present at dosage levels of between about 1 to 100%, and more preferably between about 5 to 95% of the dosage normally administered in a monotherapy regimen. The additional agents may be administered separately, as part of a multiple dose regimen, from the compounds of this invention. Alternatively, those agents may be part of a single dosage form, mixed together with the compounds of this invention in a single composition.

The pharmaceutical compositions of this invention can be administered orally to fish by blending said pharmaceutical compositions into fish feed or said pharmaceutical compositions may be dissolved in water in which infected fish are placed, a method commonly referred to as a medicated bath. The dosage for the treatment of fish differs depending upon the purpose of administration (prevention or cure of disease) and type of administration, size and extent of infection of the fish to be treated. Generally, a dosage of 5-1000 mg, preferably 20-100 mg, per kg of body weight of fish may be administered per day, either at one time or divided into several times. It will be recognized that the above-specified dosage is only a general range which may be reduced or increased depending upon the age, body weight, condition of disease, etc. of the fish.

Unless otherwise defined, all technical and scientific terms used herein are accorded the meaning commonly known to one of ordinary skill in the art. All publications, patents, published patent applications, and other references mentioned herein are hereby incorporated by reference in their entirety.

Abbreviations

Abbreviations which may appear in the following synthetic schemes and examples are:

Ac for acetyl;
AcOH for acetic acid;
AIBN for azobisisobutyronitrile;
BINAP for 2,2'-bis(diphenylphosphino)-1,1'-binaphthyl;
$Boc_2O$ for di-tert-butyl-dicarbonate;
Boc for t-butoxycarbonyl;
Bpoc for 1-methyl-1-(4-biphenylyl)ethyl carbonyl;
Bz for benzoyl;
Bn for benzyl;
BocNHOH for tert-butyl N-hydroxycarbamate;
t-BuOK for potassium tert-butoxide;
$Bu_3SnH$ for tributyltin hydride;
BOP for (benzotriazol-1-yloxy)tris(dimethylamino)phosphonium Hexafluorophosphate;
Brine for sodium chloride solution in water;
CDI for carbonyldiimidazole;
$CH_2Cl_2$ for dichloromethane;
$CH_3$ for methyl;
$CH_3CN$ for acetonitrile;
$Cs_2CO_3$ for cesium carbonate;
CuCl for copper (I) chloride;
CuI for copper (I) iodide;
dba for dibenzylidene acetone;
dppb for diphenylphosphino butane;
DBU for 1,8-diazabicyclo[5.4.0]undec-7-ene;
DCC for N,N'-dicyclohexylcarbodiimide;
DEAD for diethylazodicarboxylate;
DIAD for diisopropyl azodicarboxylate;
DIPEA or $(i-Pr)_2EtN$ for N,N,-diisopropylethyl amine;
Dess-Martin periodinane for 1,1,1-tris(acetyloxy)-1,1-dihydro-1,2-benziodoxol-3-(1H)-one;
DMAP for 4-dimethylaminopyridine;
DME for 1,2-dimethoxyethane;
DMF for N,N-dimethylformamide;
DMSO for dimethyl sulfoxide;
DPPA for diphenylphosphoryl azide;
EDC for N-(3-dimethylaminopropyl)-N'-ethylcarbodiimide;
EDC HCl for N-(3-dimethylaminopropyl)-N'-ethylcarbodiimide hydrochloride;
EtOAc for ethyl acetate;
EtOH for ethanol;
$Et_2O$ for diethyl ether;
HATU for O-(7-azabenzotriazol-1-yl)-N,N,N',N',-tetramethyluronium Hexafluorophosphate;
HCl for hydrogen chloride;
HOBT for 1-hydroxybenzotriazole;
$K_2CO_3$ for potassium carbonate;
n-BuLi for n-butyl lithium;
i-BuLi for i-butyl lithium;
t-BuLi for t-butyl lithium;
PhLi for phenyl lithium;
LDA for lithium diisopropylamide;
TMEDA for N,N,N',N'-tetramethylethylenediamine;
LiTMP for lithium 2,2,6,6-tetramethylpiperidinate;
MeOH for methanol;
Mg for magnesium;
MOM for methoxymethyl;
Ms for mesyl or $—SO_2—CH_3$;
$Ms_2O$ for methanesulfonic anhydride or mesyl-anhydride;
$NaN(TMS)_2$ for sodium bis(trimethylsilyl)amide;
NaCl for sodium chloride;
NaH for sodium hydride;
$NaHCO_3$ for sodium bicarbonate or sodium hydrogen carbonate;
$Na_2CO_3$ sodium carbonate;
NaOH for sodium hydroxide;
$Na_2SO_4$ for sodium sulfate;
$NaHSO_3$ for sodium bisulfite or sodium hydrogen sulfite;
$Na_2S_2O_3$ for sodium thiosulfate;
$NH_2NH_2$ for hydrazine;
$NH_4HCO_3$ for ammonium bicarbonate;
$NH_4Cl$ for ammonium chloride;
NMMO for N-methylmorpholine N-oxide;
$NaIO_4$ for sodium periodate;
Ni for nickel;
OH for hydroxyl;
$OSO_4$ for osmium tetroxide;
TEA or $Et_3N$ for triethylamine;
TFA for trifluoroacetic acid;
THF for tetrahydrofuran;
TPP or $PPh_3$ for triphenylphosphine;
Troc for 2,2,2-trichloroethyl carbonyl;
Ts for tosyl or $—SO_2—C_6H_4CH_3$;
$Ts_2O$ for tolylsulfonic anhydride or tosyl-anhydride;
TsOH for p-tolylsulfonic acid;
Pd for palladium;
Ph for phenyl;
POPd for dihydrogen dichlorobis(di-tert-butylphosphinito-κP)palladate (II);
$Pd_2(dba)_3$ for tris(dibenzylideneacetone)dipalladium (0);
$Pd(PPh_3)_4$ for tetrakis(triphenylphosphine)palladium (0);
$PdCl_2(Ph_3P)_2$ for trans-dichlorobis(triphenylphosphine) palladium (II);
Pt for platinum;
Rh for rhodium;
Ru for ruthenium;
TBS for tert-butyl dimethylsilyl; or
TMS for trimethylsilyl;
TMSCl for trimethylsilyl chloride.

Synthetic Methods

The compounds and processes of the present invention will be better understood in connection with the following synthetic schemes that illustrate the methods by which the compounds of the invention may be prepared.

The compounds and processes of the present invention will be better understood in connection with the following synthetic schemes that illustrate the methods by which the compounds of the invention may be prepared.

A preferred intermediate for the preparation of compounds of the invention is a compound represented by formula XVII as illustrated below:

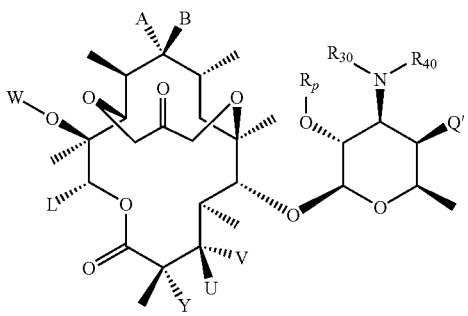

XVII wherein $R_p$, L, U, V, W, A, B, $R_{30}$, $R_{40}$, Q' and Y are as previously defined.

Schemes 1-2 describe processes for the preparation of compounds according to the invention.

Compounds of formula XVII, which are useful as the starting materials for the preparation of compounds of the present invention are prepared from erythromycin using the procedures described in U.S. Pat. Nos. 6,878,691 and 7,129,221, incorporated herein by reference.

Scheme 1

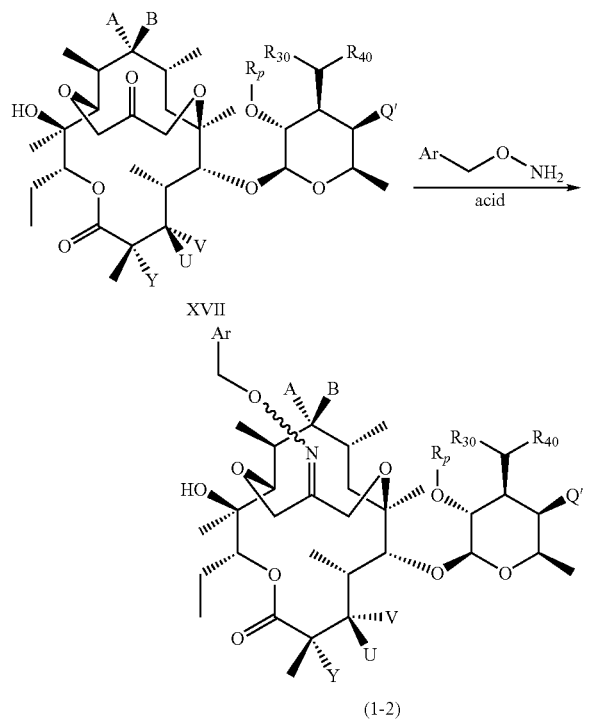

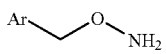

Ar is an aromatic moiety

Scheme 1 illustrates a process of preparing compounds of the present invention by converting the bridged ketone of VIII into an oxime of formula (1-2) using the appropriate substituted hydroxylamine of the formula:

Ar—CH$_2$—O—NH$_2$ where BA is as previously defined. This oxime formation can be accomplished, using the appropriate substituted hydroxy-lamine under either acidic or basic conditions in a variety of solvents. Representative acids include, but are not limited to, hydrochloric acid, phosphoric acid, sulfuric acid, p-toluene-sulfonic acid, and pyridinium p-toluene sulfonate and the likes. Likewise, representative bases include, but are not limited to, triethylamine, pyridine, diisopropylethyl amine, 2,6-lutidine, and the likes. Appropriate solvents include, but are not limited to, methanol, ethanol, water, tetrahydrofuran, 1,2-dimethoxyethane, ethyl acetate and the likes. Preferably the reaction is carried out in ethanol using aqueous hydrochloric acid. Reaction temperature is generally, but not limited to, from −20° C. to 40° C. and the reaction time is from 1 to 8 hours, preferably the reaction is carried out at 0° C.

Scheme 2

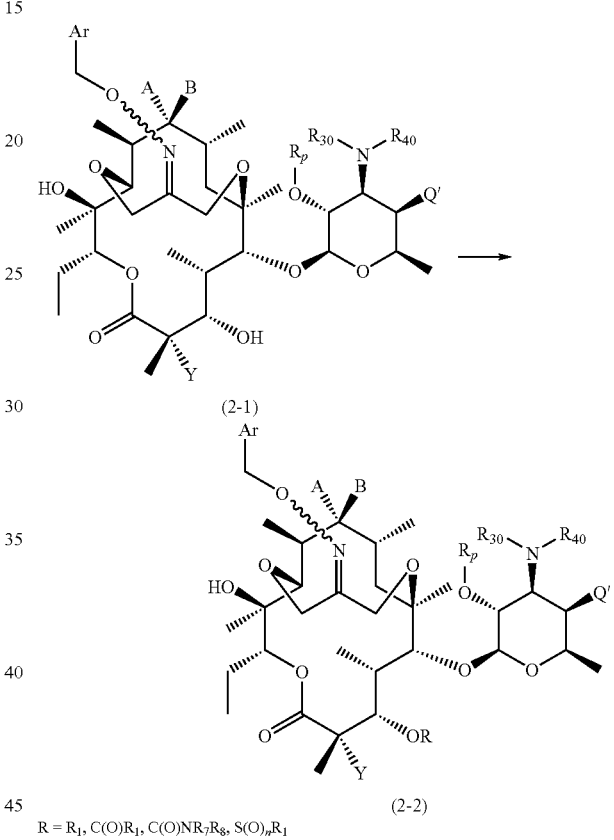

R = $R_1$, C(O)$R_1$, C(O)NR$_7$R$_8$, S(O)$_n$R$_1$

Scheme 2 illustrates the procedure by which compounds of formula (2-1) may be converted to compounds of formula (2-2) by treatment with isocyanates of formula R1-NCO, acid chlorides of formula R1-C(O)Cl or Alkyl isocyanates in the present of bases such as, but not limited to, sodium hydride, potassium hydride, potassium tert-butoxide, potassium hydroxide, KHMDS, and the like. The reaction is typically carried out in aprotic solvents such as, but not limited to, THF, DMSO, DMF, or dioxane and the likes. The temperature of the reaction is from 25° C. to 80° C. The preferred reaction time is from 5 to 20 hours.

Alternatively, some of the ester compounds of formula (2-2) can be prepared by treating compounds of formula (2-1) with acids of formula R1-C(O)OH in the presence of bases such as but not limited to Et$_3$N, Pyridine, DMAP and coupling agents such as but not limited to EDC, BOPCl, HATU, and the likes in aprotic solvents such as but not limited to dichloromethane, ethylene chloride, THF, DMF, acetonitrile and the like at a temperature from 25° C. to 80° C. and the reaction time is from 2 to 24 hours.

Compounds of formula (2-1) also can be treated with substituted tert-butyl allyl carbonate in the presence of a palladium catalyst and a phosphine additive to give allyl ethers.

The intermediates of formula

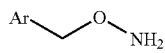

can be prepared according to methods known in the art. For example, Scheme 3 and Scheme 4 are some of the available methods of preparing

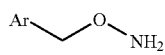

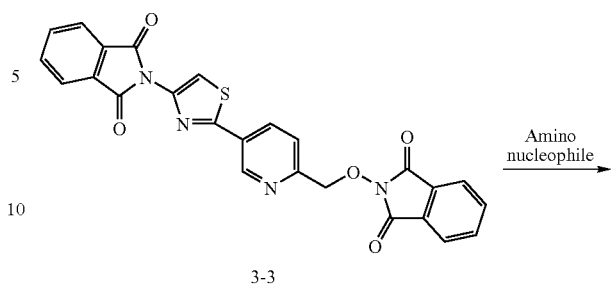

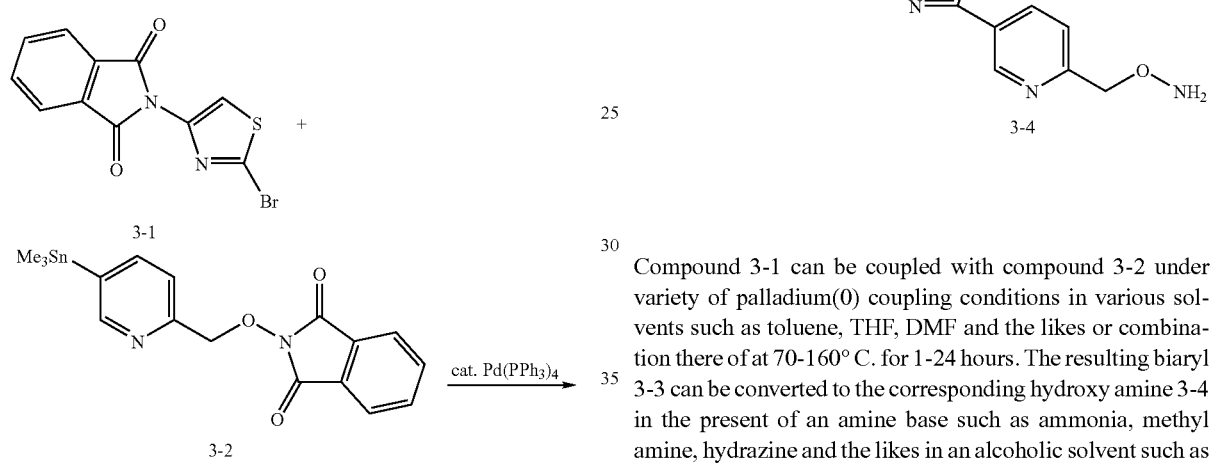

Compound 3-1 can be coupled with compound 3-2 under variety of palladium(0) coupling conditions in various solvents such as toluene, THF, DMF and the likes or combination there of at 70-160° C. for 1-24 hours. The resulting biaryl 3-3 can be converted to the corresponding hydroxy amine 3-4 in the present of an amine base such as ammonia, methyl amine, hydrazine and the likes in an alcoholic solvent such as methanol or ethanol at room temperature to 60° C.

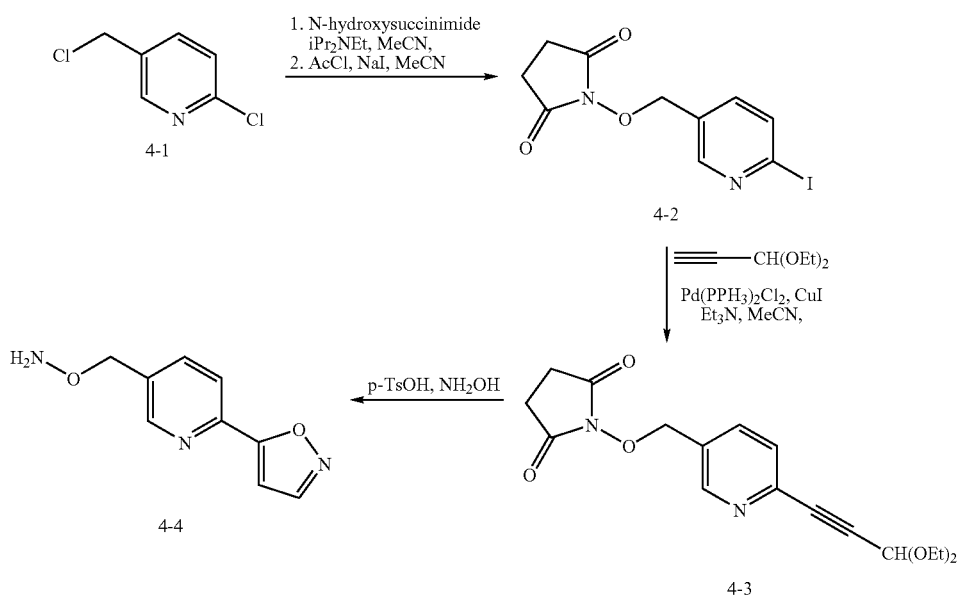

Compound 4-1 is alkylated with a protected hydroxylamine such as N-Boc hydroxy amine or N-hydroxysuccinimide in an organic solvent such as acetonitrile, THF, DMF and the likes or combination there of. The resulting alkylated product was substituted with an iodide source to converted pyridyl chloride to pyridyl iodide 4-2. Compound 4-2 is coupled with an acetylinic moiety in the present of a palladium(0) source under variety of Pd-coupling conditions to provide compound 4-3 which is further reacting with a hydroxy amine and cyclized to compound 4-4 in present of a protic acid such as HCl, MeSO$_3$H or p-toluene sulphonic acid and the likes.

All references cited herein, whether in print, electronic, computer readable storage media or other form, are expressly incorporated by reference in their entirety, including but not limited to, abstracts, articles, journals, publications, texts, treatises, internet web sites, databases, patents, and patent publications.

EXAMPLES

The compounds and processes of the present invention will be better understood in connection with the following examples, which are intended as an illustration only and not limiting of the scope of the invention. Various changes and modifications to the disclosed embodiments will be apparent to those skilled in the art and such changes and modifications including, without limitation, those relating to the chemical structures, substituents, derivatives, formulations and/or methods of the invention may be made without departing from the spirit of the invention and the scope of the appended claims.

Example 1

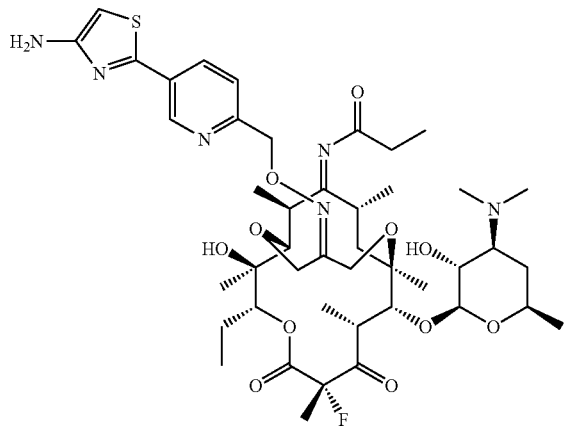

Compound 1

Step 1a

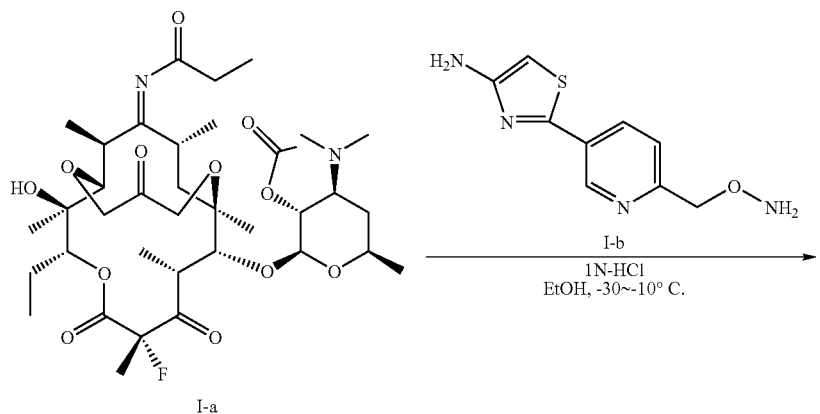

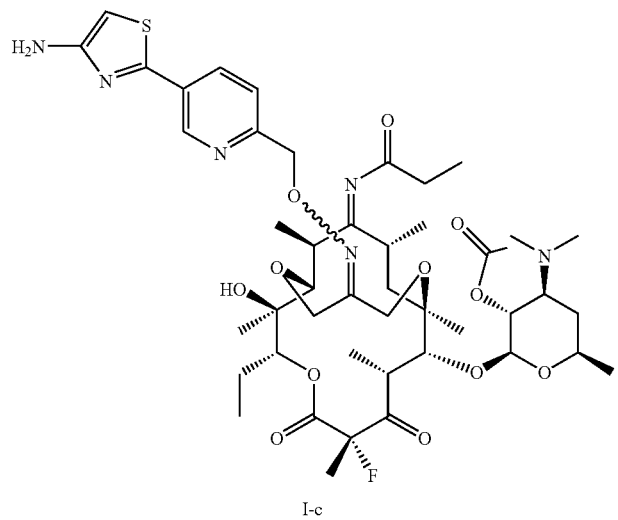

To a mixture of I-a (1.024 g, 1.378 mmol) and O-[5-(4-aminothiazol-2-yl)-pyridin-2-ylmethyl]-hydroxylamine (I-b, 306 mg, 1.378 mmol) in ethanol (17 mL) was dropwise added 1N-HCl aq. solution (2.07 mL) at −30° C. and stirred between −30° C. and −10° C. for 30 min. The reaction mixture was diluted with isopropyl acetate (200 mL), washed with aq. NaHCO$_3$ solution (50 mL), water (50 mL) and brine successively. The organic layer was dried (Na$_2$SO$_4$), filtered and evaporated to dryness. The residue was passed through a short silica gel column using 30% acetone in ethyl acetate to give the title compound I-c as a pale yellow foam. E/Z=3.4:1. MS: (ESI) m/z (M+H)$^+$ 947.7.
Step 1b I-c previously obtained was purified by RP-HPLC to afford a pure E-isomer, which was dissolved in methanol (10 mL), kept in room temperature for 32 hours to remove 2'-OAc protecting group and evaporated to provide the title compound 1 as a pale orange foam.

MS: (ESI) m/z (M+H)$^+$ 905.4.

$^{13}$C-NMR (CDCl$_3$): δ 205.1, 204.9, 187.3, 176.9, 164.7, 164.5, 162.3, 159.2, 157.3, 154.2, 146.5, 133.4, 128.3, 121.3, 103.9, 99.5, 97.9, 90.8, 79.4, 76.3, 73.5, 70.4, 69.6, 65.8, 62.9, 62.3, 41.1, 40.2, 38.7, 31.0, 29.6, 28.1, 24.3, 24.1, 22.9, 21.2, 20.6, 17.1, 14.7, 14.2, 12.4, 8.6.

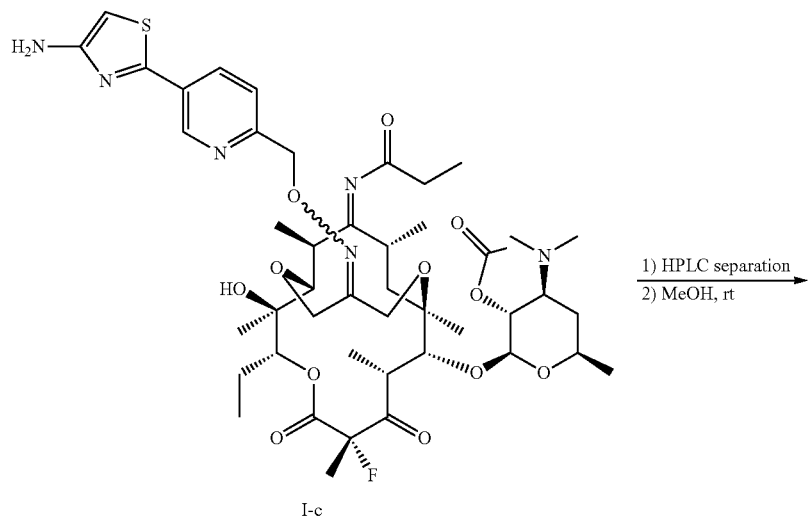

I-c

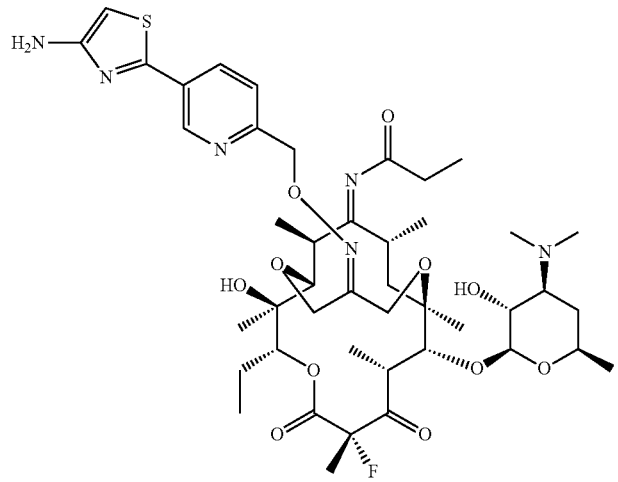

1

Example 2

Compound 2

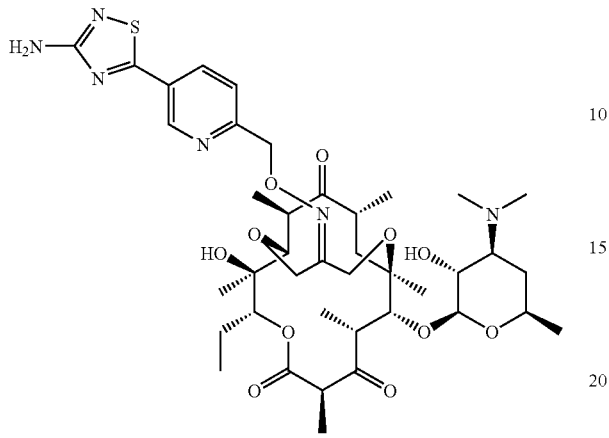

Step 2a

To a mixture of II-a (120 mg, 0.18 mmol) and O-[5-(3-amino-[1,2,4]thiadiazol-5-yl)-pyridin-2-ylmethyl]-hydroxylamine (II-b, 0.18 mmol) in ethanol (3 mL) was dropwise added 1N-HCl (0.27 mL) at −40° C. and stirred between −30° C. and −10° C. for 30 min. The reaction was diluted with $CH_2Cl_2$ (10 mL), washed with saturated aq. $NaHCO_3$ solution (5 mL), water (5 mL) and brine successively. The organic layer was dried ($Na_2SO_4$), filtered and evaporated to give a crude title compound II-c as a white foam. E/Z=2.0:1.

MS: (ESI) m/z (M+H)$^+$ 875.5.

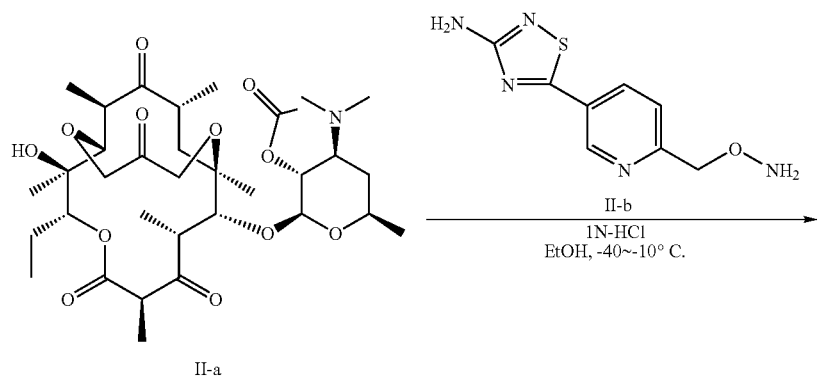

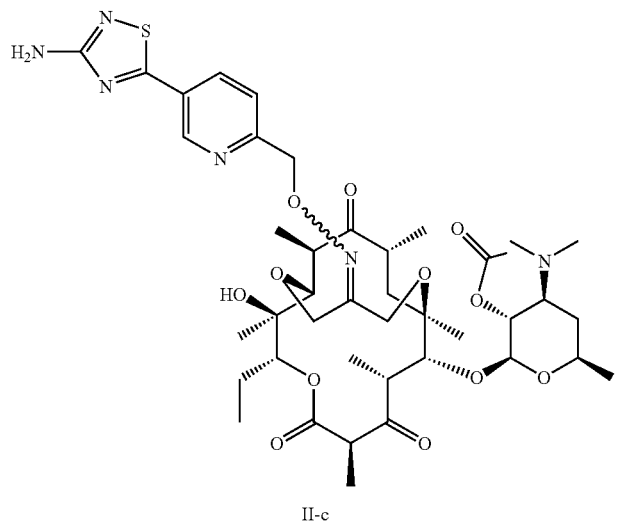

Step 2b:
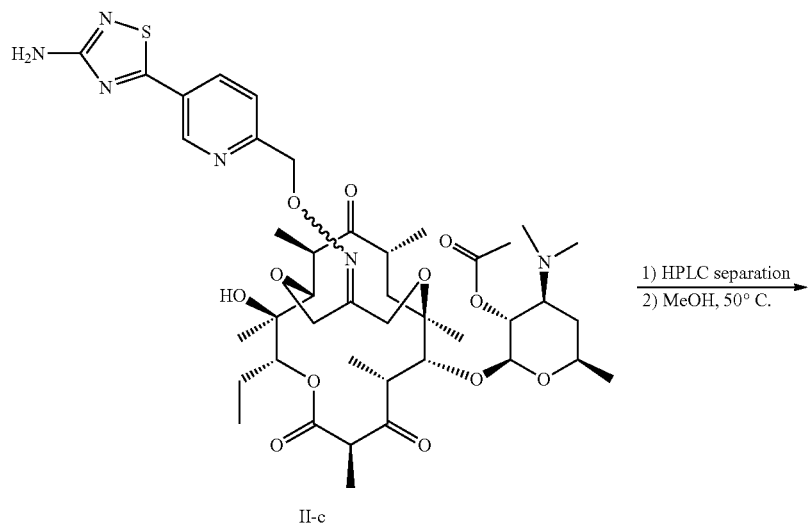
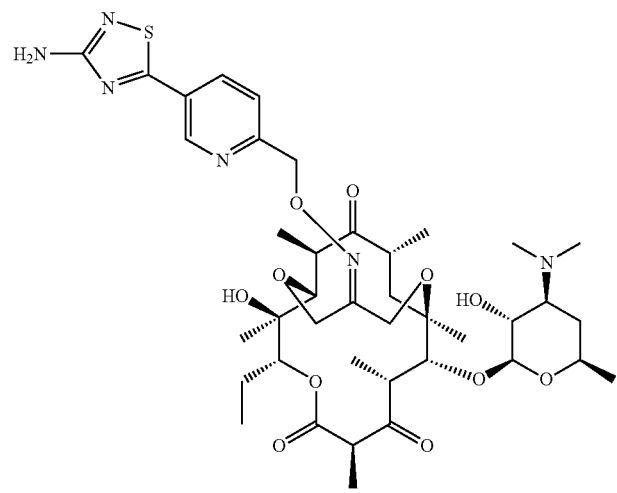
II-c previously obtained was purified by RP-HPLC to afford a pure E-isomer, which was dissolved in methanol (3 mL), kept at 50° C. for 3 hours to remove 2'-OAc protecting group and evaporated to provide the title compound 2 as a white foam. MS: (ESI) m/z (M+H)$^+$ 833.5.
$^{13}$C-NMR (CDCl$_3$): δ 217.6, 205.6, 184.6, 170.4, 168.3, 161.9, 154.1, 147.5, 134.9, 125.6, 122.3, 103.2, 79.5, 78.8, 76.7, 76.5, 75.9, 75.6, 70.5, 69.7, 66.0, 62.8, 62.0, 51.0, 47.1, 46.1, 40.4, 39.3, 39.2, 28.5, 23.4, 21.4, 20.3, 18.5, 18.0, 14.6, 14.2, 12.4, 12.2.

Example 3
Compound 3
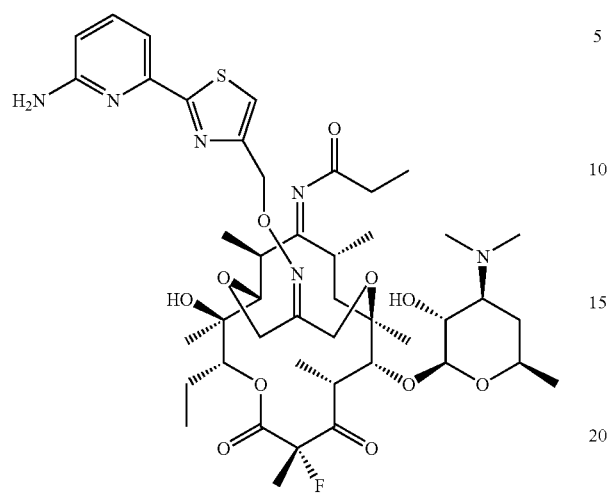
Step 3a
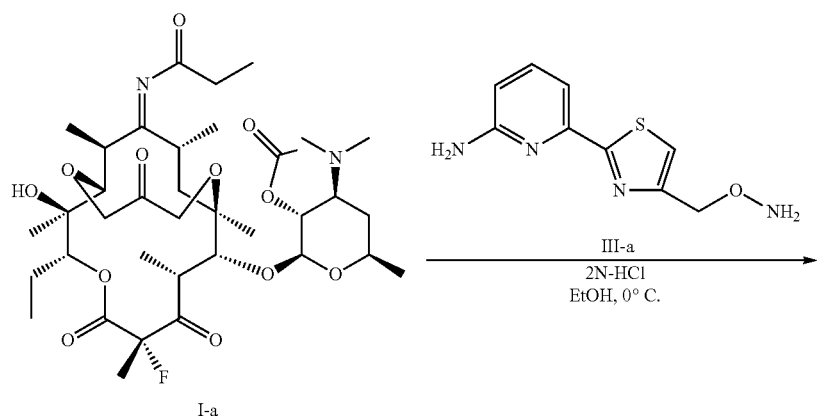
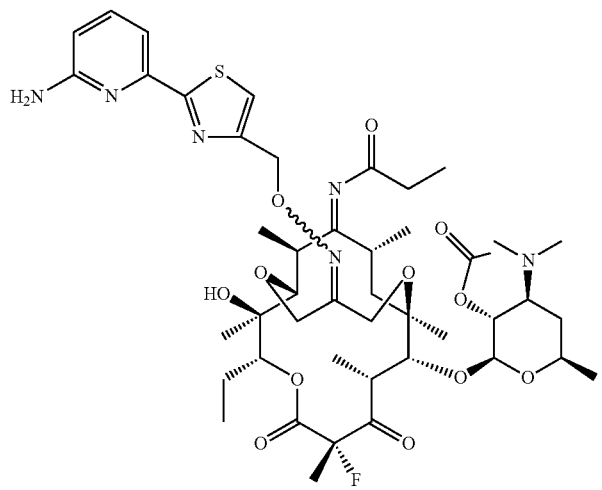

To a solution of O-[2-(6-aminopyridyl-2-yl)-thiazol-4-ylmethyl]-hydroxylamine (III-a, 655 mg, 2.7 mmol) in ethanol (40 mL) was added 2N-HCl (2.7 mL) at 0° C. and stirred for 5 min. Then, I-a (2.0 g, 2.7 mmol) was added to the reaction mixture in one portion and stirred at 0° C. for 30 min. The reaction was quenched by addition of saturated aqueous NaHCO$_3$ solution and extracted with CH$_2$Cl$_2$ (3×70 mL). The combined organic layer was washed with brine, dried (Na$_2$SO$_4$), filtered and evaporated to dryness. The crude compound was purified by silica gel column chromatography using 50% acetone in hexanes to give the title compound III-b (1.84 g) as a white foam. E/Z=2.7:1.

MS: (ESI) m/z (M+H)$^+$ 947.8.

Step 3b

The previously obtained III-b was purified by RP-HPLC to afford a pure E-isomer (660 mg), which was dissolved in methanol (15 mL), heated in microwave at 100° C. for 15 min to remove 2'-OAc protecting group and evaporated to afford the title compound 3 as a white foam.

MS: (ESI) m/z (M+H)$^+$ 905.6.

$^{13}$C-NMR (CDCl$_3$): δ 205.1, 204.9, 187.3, 169.3, 157.9, 154.3, 149.5, 138.5, 118.3, 110.1, 109.6, 103.9, 99.5, 97.8, 79.4, 76.3, 73.3, 72.0, 70.3, 69.6, 65.7, 62.9, 41.0, 40.2, 31.0, 28.1, 24.3, 23.0, 21.2, 20.6, 17.1, 14.7, 14.2, 12.4, 8.6.

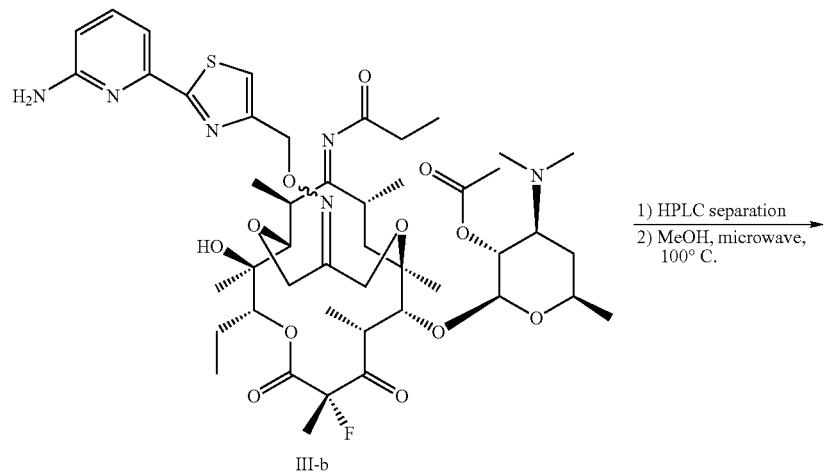

III-b

1) HPLC separation
2) MeOH, microwave, 100° C.

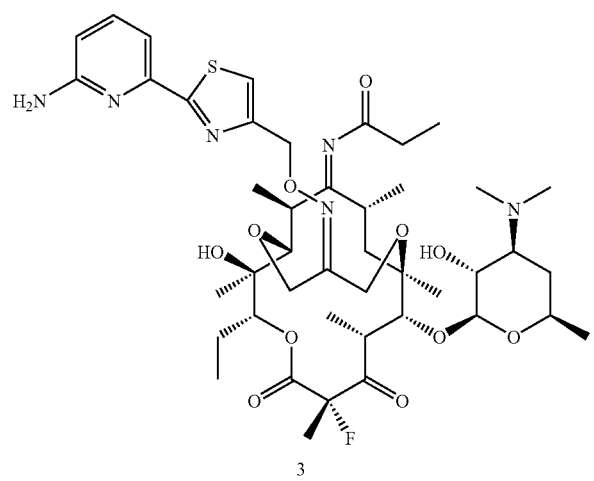

3

Example 4

Compound 4

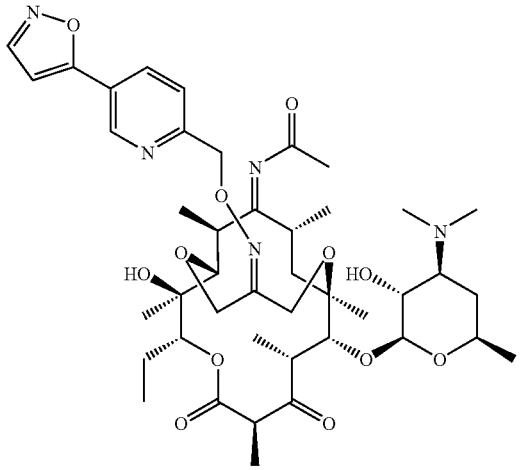

Into a solution of O-(6-Isoxazol-5-yl-pyridin-3-ylmethyl)-hydroxylamine (4.2 mmol at most) in EtOH (30 mL) and HCl (1.0 M aq, 20 mL, 20 mmol) was charged bridged ketone IV-a (3.30 g, 4.2 mmol) at −10° C. The mixture was stirred at −10° C. for 1.5 hours before being neutralized with solidic NaHCO$_3$ and partitioned (EtOAc—H$_2$O). The organics were washed with water and brine, dried (Na$_2$SO$_4$) and evaporated. The residue was chromatographed (silica, hexanes-EtOAc) to give the desired compound IV-b (3.22 g, 87%) as an oxime E/Z mixture (4:1). MS: (ESI) m/e: 884.42 (M+H)$^+$. 1.075 g of this mixture was separated by RP-HPLC to afford 530 mg pure E-isomer.

Step 4a

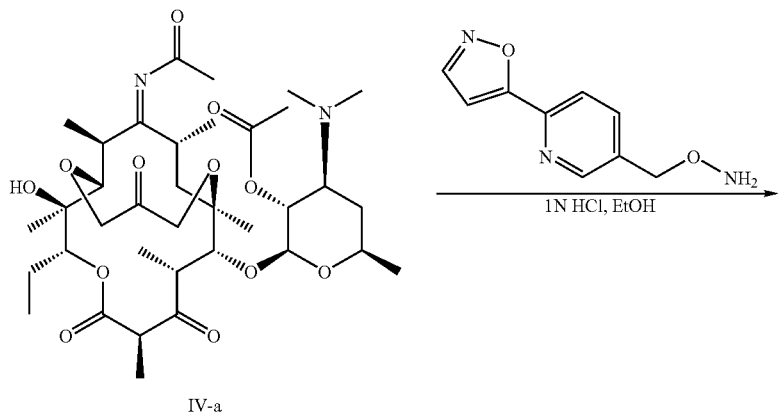

IV-a

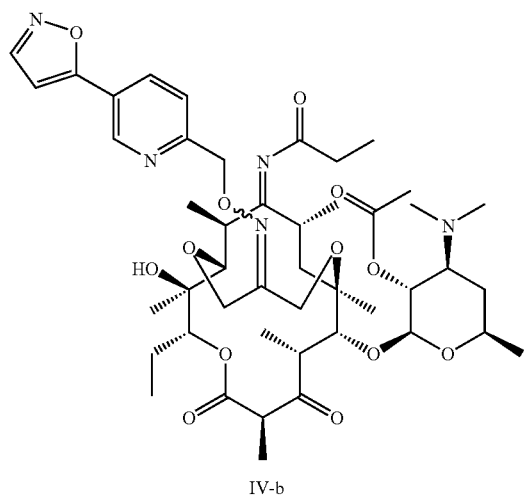

IV-b

Step 4b

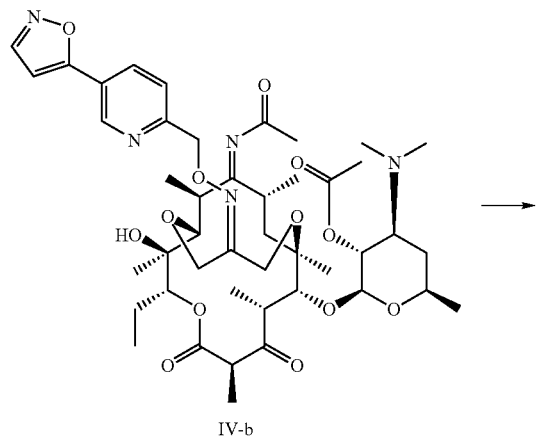

Example 5

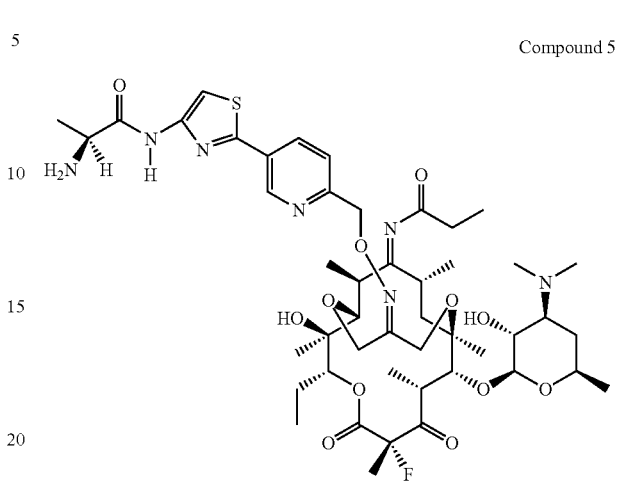

Step 5a

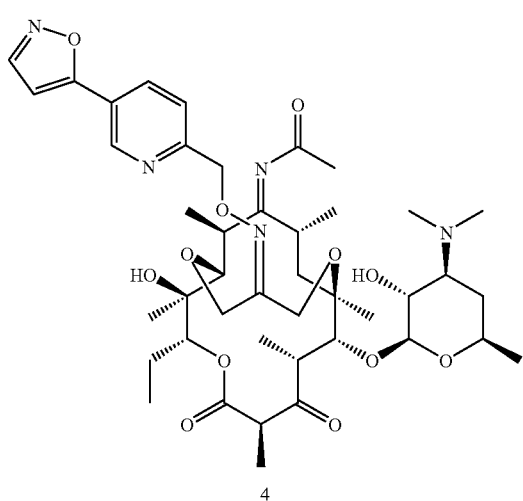

A mixture of O-[5-(4-Aminothiazol-2-yl)-pyridin-2-ylm-ethyl]-hydroxylamine (I-b, 31.54 mmol) in dioxane-water (1:1, 316 mL) was cooled to 0° C. Sodium bicarbonate (3.15 g, 37.85 mmol) and BOC-anhydride (7.57 g, 34.7 mmol) were added successively and stirred at room temperature for 14 hrs. The solid was filtered through a fritted funnel, washed with water (50 mL) and dried on vacuum for overnight to provide the title compound V-b (5.65 g) as a white solid. Second solid obtained from the filtrate was purified with silica gel column chromatography using 0-7% methanol (0.5N-ammonia contained) in methylene chloride to afford the title compound V-b (1.713 g) as a white powder. Combined yield (7.363 g, 73%). MS: (ESI) m/z (M+H) 323.2.

Step 5b

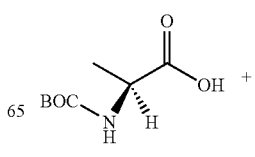

A solution of the compound from step 4a (546 mg) in MeOH was stood at room temperature for 63 hours before being evaporated and dried to give the title compound 4 (520 mg, 100%).

MS: (ESI) m/e: 842.39 (M+H)$^+$; $^{13}$CNMR (CDCl$_3$): δ 205.8, 184.7, 177.9, 169.0, 167.9, 154.3, 151.3, 150.0, 145.9, 137.1, 134.8, 120.8, 103.0, 101.6, 79.4, 79.2, 76.8, 75.6, 74.7, 73.2, 70.4, 73.2, 70.4, 69.6, 66.2, 63.0, 62.8, 50.7, 46.2, 40.5, 38.8, 37.2, 28.8, 25.3, 23.8, 21.4, 20.2, 19.5, 17.8, 15.1, 14.1, 13.6, 13.0.

-continued

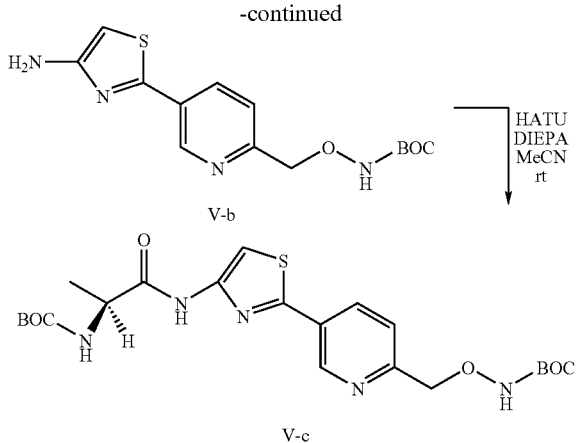

To a mixture of BOC L-alanine (189.2 mg, 1.0 mmol), V-b (306 mg, 0.95 mmol) and N,N'-diisopropylethylamine (0.348 mL, 2.0 mmol) in acetonitrile (7 mL) was added HATU (456 mg, 1.2 mmol) portion wise at room temperature and stirred for 70 min. Additional 0.1 equivalent of BOC L-alanine was added to the reaction mixture and stirred for 30 min. The reaction was diluted with isopropyl acetate (100 mL), washed with saturated aqueous sodium bicarbonate solution (30 mL), water (20 mL) and brine. The organic layer was dried (Na$_2$SO$_4$), filtered and evaporated to dyness. The residue was purified by silica gel column chromatography using 0-55% ethyl acetate in hexanes to give the title compound V-c (324 mg, 69%) as a pale yellow foam.

MS: (ESI) m/z (M+H) 494.1.

$^{13}$C NMR (in CD$_3$OD): δ 173.9, 162.6, 159.2, 150.1, 147.2, 135.7, 130.3, 124.6, 104.1, 82.5, 80.9, 79.1, 51.9, 39.0, 28.9, 28.7, 18.6.

Step 5c

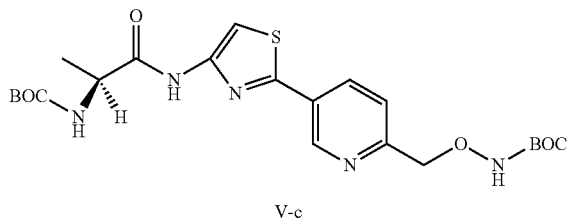

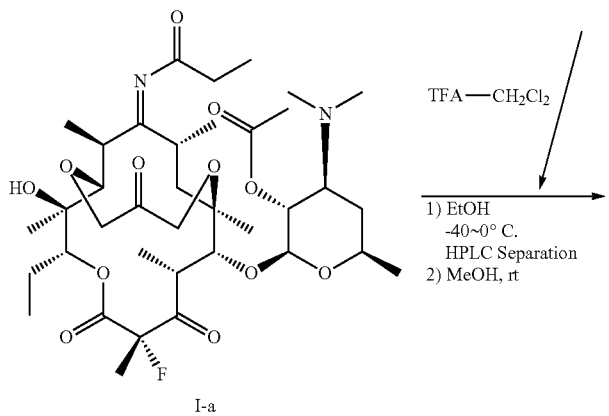

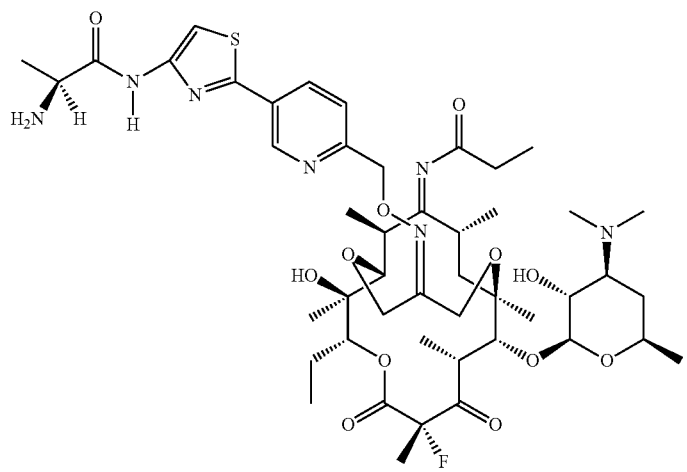

A solution of V-c (296 mg, 0.6 mmol) in methylene chloride (4 mL) was cooled to 0° C., treated with trifluoroacetic acid (4 mL) and stirred at room temperature for 1 hr. The reaction was evaporated in vacuo, dissolved in methylene chloride (3 mL) and evaporated in vacuo (repeated once). The residue was dissolved in ethanol (8.6 mL), cooled to −40° C. Then, I-a (446 mg, 0.6 mmol) was added to the reaction mixture portion wise and slowly allowed to warm to 0° C. for 40 min. After being cooled to −30° C., Additional I-a (22 mg) was added to the reaction and slowly allowed to warm to 0° C. for 20 min. The reaction was diluted with $CH_2Cl_2$ (50 mL), washed with saturated aqueous sodium bicarbonate solution (2×10 mL), water (5 mL) and brine successively. The organic layer was dried ($Na_2SO_4$), filtered and evaporated to dryness (E/Z=12.5:1 by analytical RP-HPLC). The residue was purified by preparative RP-HPLC using 50% acetonitrile in 20 mM aqueous ammonium acetate solution as a mobile phase to afford a pure E-isomer. Thus, the pure E-isomer was dissolved in methanol (10 mL), kept at room temperature for 48 hours and evaporated to give the title compound 5 (322 mg, 55% over two steps) as a pale yellow foam.

MS: (ESI) m/z (M+H) 976.7.

$^{13}C$ NMR (in $CDCl_3$): δ 205.4, 205.1, 187.6, 177.1, 174.0, 165.0, 164.8, 162.0, 160.0, 154.6, 148.3, 146.9, 134.0, 128.2, 121.8, 104.0, 102.1, 99.8, 98.1, 80.4, 79.7, 76.5, 73.8, 70.6, 69.6, 66.0, 63.2, 62.6, 51.1, 41.4, 40.3, 39.0, 37.6, 31.3, 28.8, 24.6, 24.4, 23.2, 21.8, 21.4, 20.9, 17.4.

Example 6

Compound 6

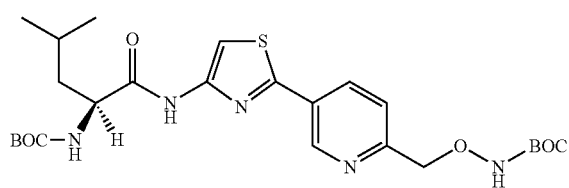 [SMILES: CC(C)C[C@H](NC(=O)OC(C)(C)C)C(=O)Nc1csc(-c2ccc(CONC(=O)OC(C)(C)C)nc2)n1]

The title compound was prepared according to the procedures of Example 5 replacing Boc-L-alanine with Boc-L-leucine.

Spectral data for:

MS: (ESI) m/z (M+H) 536.2.

$^{13}C$ NMR (in $CD_3OD$): δ 173.8, 162.4, 159.2, 150.0, 147.2, 135.7, 130.3, 124.6, 104.2, 82.5, 80.9, 79.2, 55.0, 42.5, 28.9, 28.7, 26.2, 23.7, 22.2.

Spectral data for the title compound 6:

MS: (ESI) m/z (M+H) 1018.5.

$^{13}C$ NMR (in $CDCl_3$): δ 205.4, 205.1, 187.6, 177.2, 174.0, 165.0, 164.8, 162.0, 160.0, 154.6, 148.4, 146.9, 133.9, 128.2, 121.7, 110.0, 104.1, 102.1, 99.8, 98.1, 80.4, 79.7, 76.5, 73.8, 70.6, 69.7, 66.0, 63.2, 62.6, 53.9, 44.2, 41.3, 40.3, 39.0, 37.5, 31.3, 28.6, 25.2, 24.6, 24.4, 23.6, 23.2, 21.6, 21.4, 20.9, 17.4, 15.0, 14.5, 12.7, 8.9.

Example 7-8

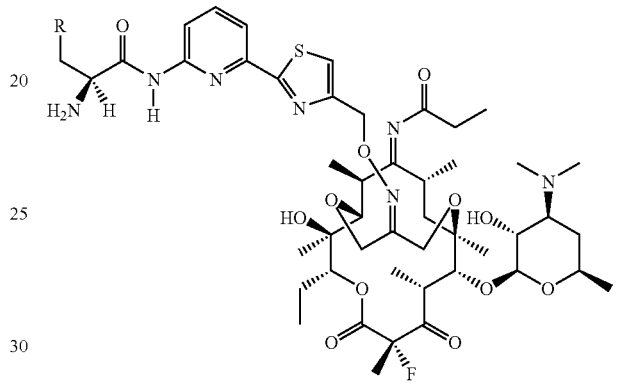

Compound 7: R = H
Compound 8: R = Isopropyl

Step 7a

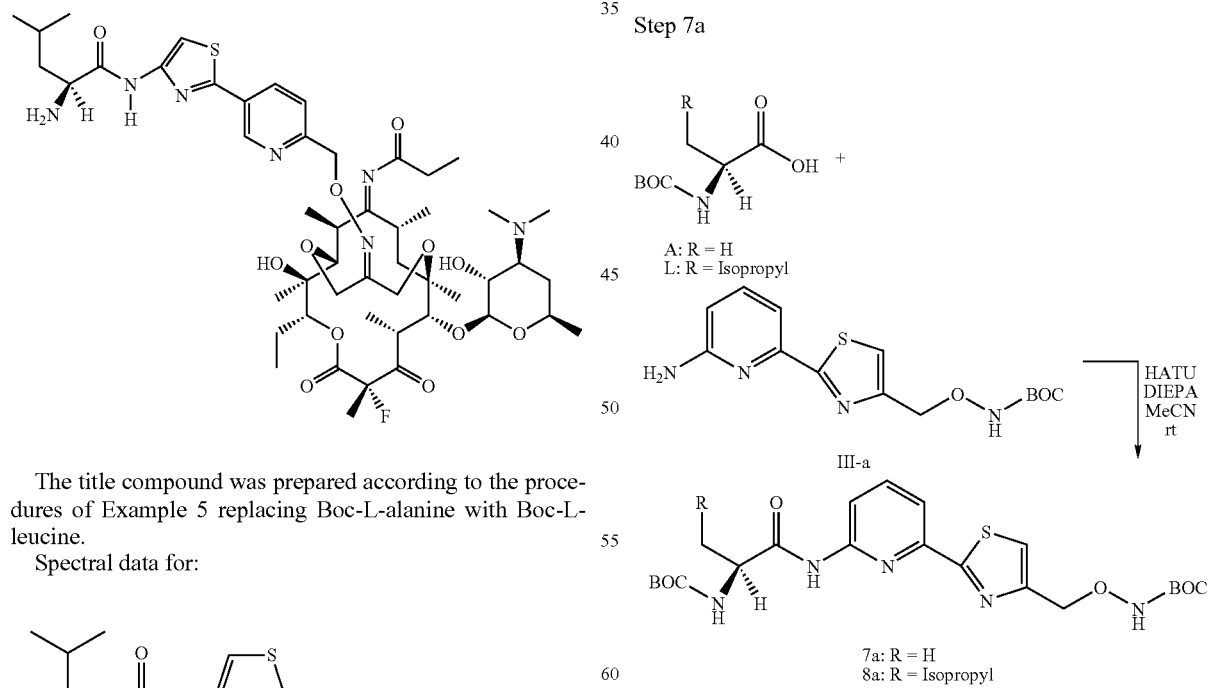

A: R = H
L: R = Isopropyl

III-a

7a: R = H
8a: R = Isopropyl

R=H: The title compound 7a was prepared according to the procedure described in the preparation of V-c (Example 5, Step 5b). MS: (ESI) m/z (M+H) 494.3.

$^{13}C$ NMR (in $CDCl_3$): δ 171.8, 168.9, 157.0, 153.0, 150.9, 149.4, 139.5, 120.9, 116.0, 115.1, 82.1, 73.7, 28.5, 28.4, 18.1,

Step 8a

R=Isopropyl: The title compound 8a was prepared according to the procedure described in the preparation of 5a (Example 5, Step 5b). MS: (ESI) m/z (M+H) 536.3.

Step 7b and 8b

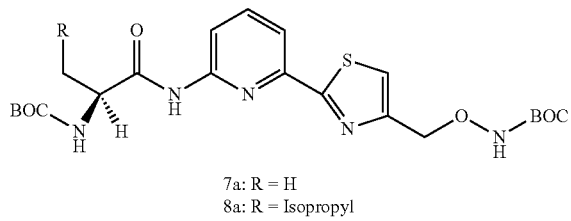

7a: R = H
8a: R = Isopropyl

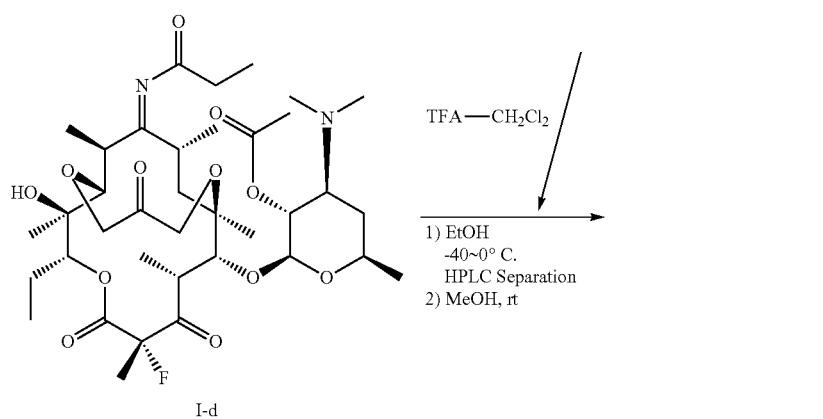

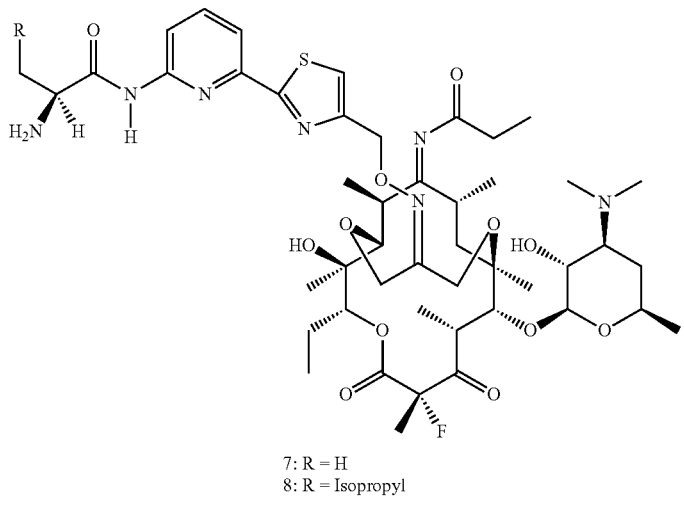

7: R = H
8: R = Isopropyl

Step 7b

R=H: The title compound 7 (R=H) was prepared according to the procedure described in the preparation of 5 (Example 5, Step 5c).

MS: (ESI) m/z (M+H) 976.4.

$^{13}$C NMR (in CDCl$_3$): δ 205.4, 205.2, 187.5, 177.1, 174.9, 168.5, 165.0, 164.8, 154.9, 154.1, 151.0, 149.8, 139.5, 119.0, 115.9, 114.5, 104.2, 99.8, 98.1, 80.3, 79.7, 76.6, 73.7, 72.2, 70.6, 69.9, 66.1, 63.1, 62.6, 51.6, 41.3, 40.5, 39.0, 37.5, 31.3, 29.9, 28.4, 24.6, 24.4, 23.2, 21.8, 21.5, 20.9, 17.4, 15.0, 14.4, 12.7, 8.9.

Step 8b

R=Isopropyl: The title compound 8 (R=isopropyl) was prepared according to the procedure described on the preparation of 5 (Example 5, Step 5c).

MS: (ESI) m/z (M+H) 1018.5.

$^{13}$CNMR (in CDCl$_3$): δ 205.4, 205.2, 187.5, 177.2, 174.9, 168.5, 165.0, 164.8, 154.9, 154.1, 151.0, 149.8, 139.5, 119.0, 115.8, 114.6, 104.2, 99.8, 98.1, 80.3, 79.7, 76.6, 73.7, 72.2, 70.6, 69.9, 66.0, 63.1, 62.6, 54.3, 44.1, 41.3, 40.5, 39.0, 37.6, 31.3, 29.9, 28.4, 25.2, 24.6, 24.4, 23.6, 23.2, 21.6, 21.4, 20.9, 17.3, 15.0, 14.4, 12.7, 8.9.

Example 9
Compound 9
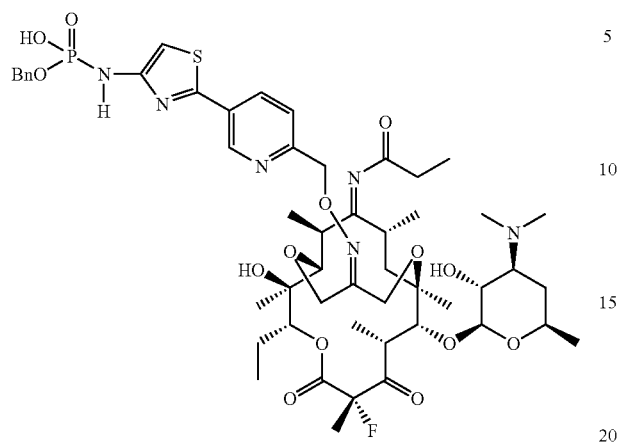
Step 9a
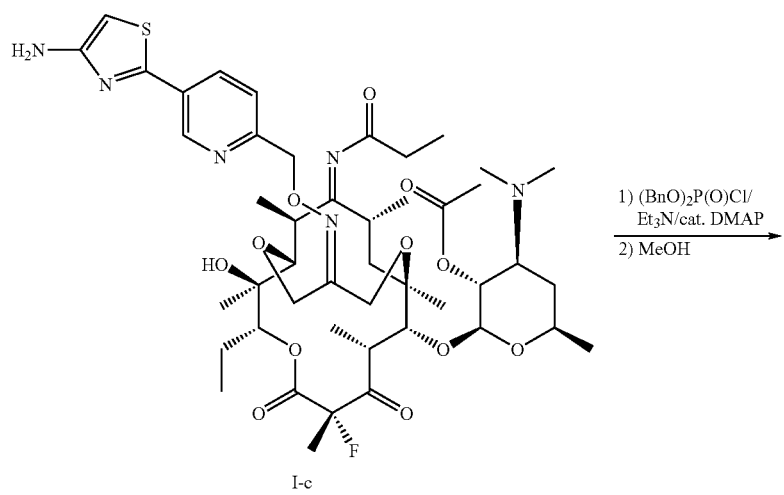
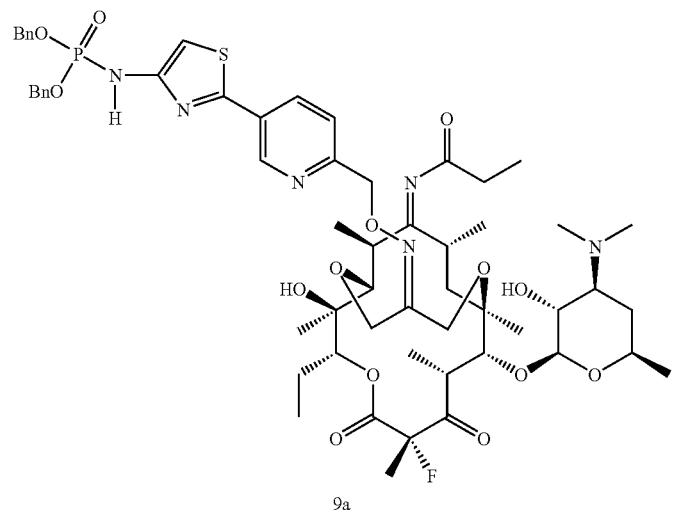

To a mixture of I-c (1.1 g, 1.16 mmol) and 10% dibenzylphosphoryl chloride (1.45 mL) in toluene was added triethylamine (0.3 mL) and N,N-dimethylaminopyridine (DMAP, 5 mg). The reaction mixture was heated at 50° C. for 16 hr. The reaction was diluted with ethyl acetate (20 mL), washed with saturated acqueous sodium bicarbonate solution (2×10 mL), water (10 mL) and brine. The organic layer was dried ($Na_2SO_4$), filtered and evaporated to dryness. The residue was purified by silica gel column chromatography using 40-80% acetone in hexanes to give the N-phosphorylated product (210 mg, 15%) as a yellow foam (MS: (ESI) m/z (M+H) 1207.9. The resulting foam was dissolved in methanol and stirred at room temperature for 16 hrs and evaporated to afford the title compound 9a. MS: (ESI) m/z (M+H) 1165.7. Step 9b A mixture of 9a (28 mg) and 10% palladium on carbon (10% Pd—C, 30 mg) in ethanol (3 mL) was degassed and filled with hydrogen gas. It was vigorously stirred under hydrogen atmosphere (16 psi) for 17 hr to give the title compound 9. MS: (ESI) m/z (M+H) 1075.6.

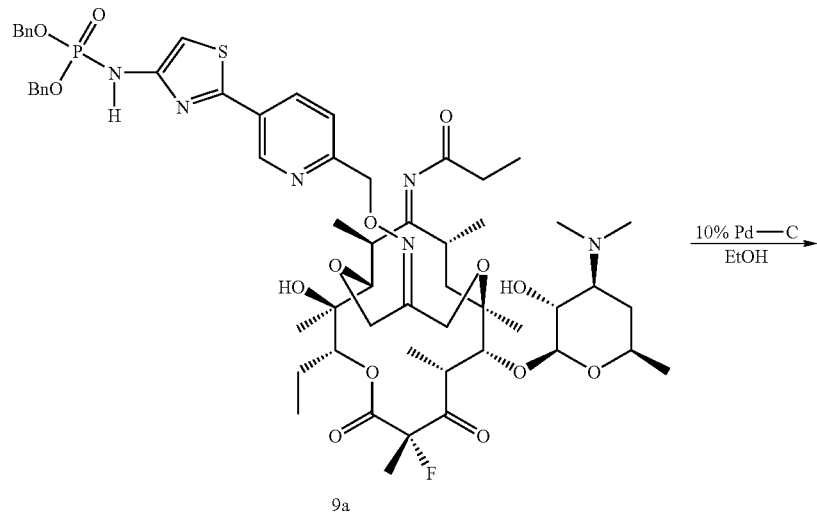

9a

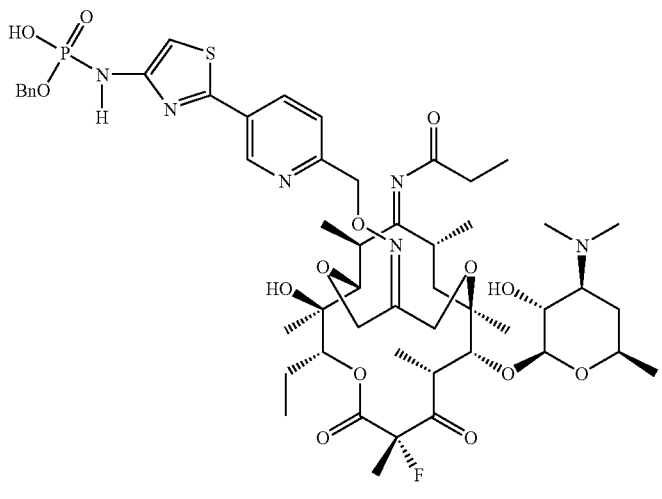

9

Example 10

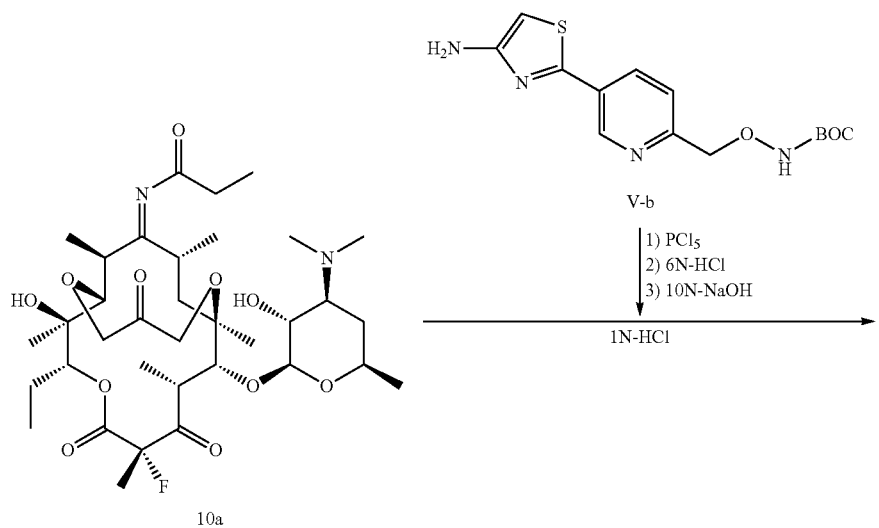

To a mixture of phosphorous pentachloride (458 mg, 2.2 mmol) in ethyl acetate (5 mL) was added dropwise V-b (644 mg, 2.0 mmol) in methylene chloride (14 mL) at 0° C. for 5 min. 6N-HCl (1 mL) was dropwise added to the above reaction mixture at 0° C. and stirred vigorously for 1 hr. After being evaporated, it was dissolved in water (8 mL), cooled to 0° C., diluted with ethanol (20 mL) and neutralized with 10N-sodium hydroxide (1.8 mL). Then, 10a (981 mg, 1.4 mmol) was added, cooled to −30° C. and diluted further by adding acetonitrile (10 mL). 1N-HCl (3 mL) was dropwised added to the reaction, diluted with water (20 mL) and slowly allowed to warm up to −10° C. with stirring for 50 min. Additional 1N-HCl (0.5 mL) was added and slowly allowed to warm up to 0° C. for 30 min. The reaction was neutralized by adding concentrated ammonia and evaporated off. The reaction was filtered and dried to afford a crude product, which was purified with $C_{18}$ RP-column using 0-50% methanol (0.5N—$NH_3$) in water as a mobile phase and lyophilized to give the title compound 10.

MS: (ESI) m/z (M+H) 985.5.

Example 11

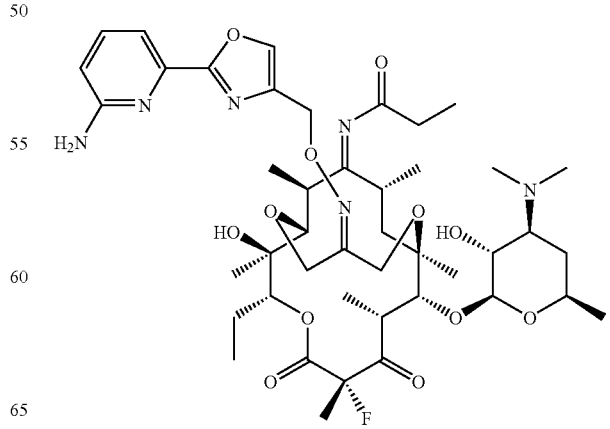

Step 11a

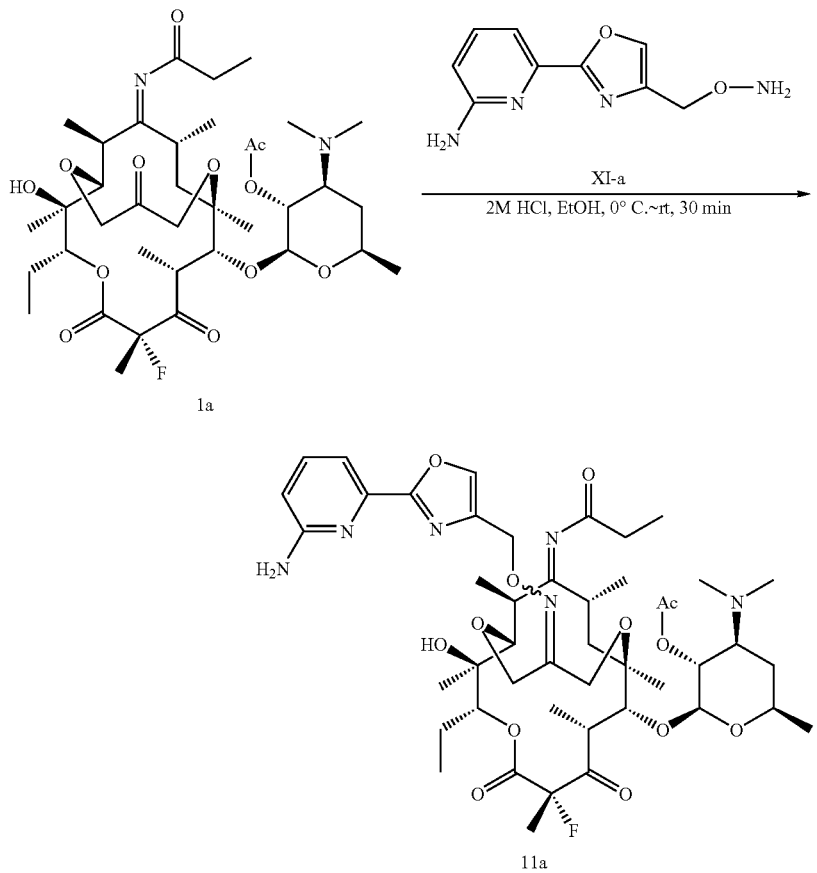

To a solution of the hydroxylamine XI-a (187 mg, 0.91 mmol) in EtOH (10 mL) was added 2 M HCl aqueous solution (0.37 mL, 0.74 mmol) at 0° C. After stirring 5 min, the bridged ketone 1a was added as a solid in one portion, the mixture was stirred at room temperature for 30 min. The reaction mixture was quenched with aqueous saturated sodium bicarbonate solution, extracted with $CH_2Cl_2$ (×3), washed with brine. The organic layer was concentrated to dryness. The residue was purified on silica gel column chromatography eluting with 50% acetone in hexane to afford 408 mg (60% yield) of the title compound 11a as a mixture of the bridged oxime (E/Z=5:1). MS: (ESI) m/z (M+H) 931.6.

Step 11b

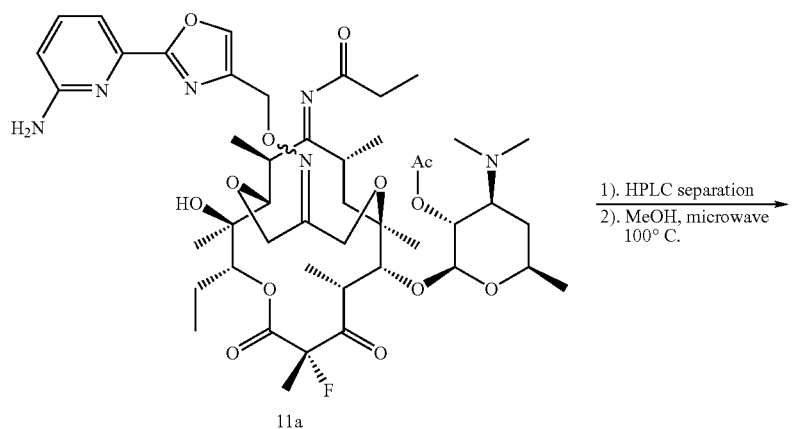

-continued

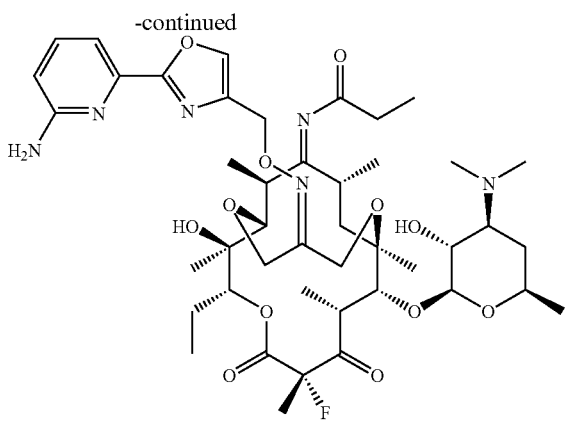

11

The E, Z mixture from step 11a was separated by HPLC to give 172 mg of E-isomer and 27 mg of Z-isomer. The E-isomer (172 mg) was microwaved in MeOH (10 mL) at 100° C. for 12 min. The reaction solution was concentrated to dryness, the residue was further dried in vacuo to provide the title compound 11 (165 mg) as quantitative yield.

MS: (ESI) m/z (M+H) 889.4.

$^{13}$C NMR (in CDCl$_3$) δ: 205.1, 204.9, 187.3, 164.5, 160.7, 158.4, 153.8, 144.2, 138.9, 138.3, 137.3, 112.5, 110.1, 103.5, 99.5, 97.9, 79.5, 76.3, 73.4, 70.2, 69.2, 68.2, 66.0, 62.8, 62.4, 41.0, 40.2, 31.0, 24.3, 24.1, 22.9, 21.1, 20.6, 17.1, 14.7, 14.2, 12.4, 8.6.

Examples 12-140 (Table 6) were prepared according to the procedures of examples 1-11 and that of U.S. Pat. No. 6,878,691.

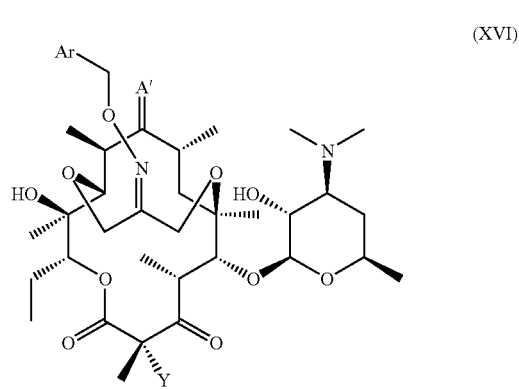
(XVI)

TABLE 6

| Example | Ar | Y | A' | MS (M + H): m/e | Selected $^{13}$C (125 MHz, CDCl$_3$) δ |
|---|---|---|---|---|---|
| 12 | ![pyridine-thiadiazole with H2N] | F | NC(O)Me | 892 | 205.1, 204.9, 184.0, 171.7, 168.6, 164.8, 158.2, 155.3, 147.2, 138.6, 111.1, 110.4, 103.9, (99.5, 97.9), 79.5, 76.3, 73.5, 70.6, 70.4, 69.6, 65.8, 62.8, 62.3, 41.1, 40.2, 38.6, 28.2, 25.0, 24.3, 24.1, 23.0, 21.2, 20.7, 17.1, 14.7, 14.1, 12.6 |
| 13 | ![pyridine-imidazole with H2N] | H | NC(O)Me | 856 | 205.6, 184.4, 177.7, 167.4, 158.1, 152.9, 147.7, 140.0, 139.6, 134.6, 115.1, 106.2, 102.6, 100.8, 79.1, 78.8, 76.4, 74.5, 70.1, 70.0, 69.3, 65.7, 62.8, 62.5, 50.5, 50.4, 45.9, 40.1, 38.4, 29.8, 29.6, 28.4, 25.0, 23.4, 21.1, 20.2, 19.2, 17.4, 14.7, 14.0, 13.8, 13.4, 12.5. |
| 14 | ![isoxazole-pyridine] | H | O | 801.4 | 218.3, 205.5, 169.0, 168.1, 153.7, 151.3, 150.1, 145.9, 137.3, 134.7, 120.8, 103.1, 101.6, 79.4, 79.0, 76.8, 75.9, 74.7, 73.3, 70.4, 69.6, 66.2, 62.9, 61.4, 50.9, 47.1, 46.2, 40.5, 39.4, 39.3, 28.9, 23.5, 21.4, 20.1, 18.5, 18.0, 14.6, 14.2, 122.7, 12.1. |

TABLE 6-continued

| Example | Ar | Y | A' | MS (M + H): m/e | Selected $^{13}$C (125 MHz, CDCl$_3$) δ |
|---|---|---|---|---|---|
| | | H | O | 801.4 | 281.4, 205.5, 168.0, 162.5, 159.2, 153.6, 149.7, 147.8, 137.2, 134.6, 121.6, 103.6, 103.3, 79.4, 79.0, 76.8, 75.9, 74.6, 73.4, 70.5, 69.7, 66.2, 62.9, 61.4, 50.9, 47.1, 46.2, 40.5, 39.4, 39.3, 28.7, 23.5, 21.5, 20.1, 18.5, 18.0, 14.6, 14.2, 12.7, 12.1. |
| 16 | 3-amino-1-(pyridin-2-yl)pyrazole | H | O | 815.46 | 218.44, 205.5, 168.0, 153.2, 148.3, 139.4, 129.6, 128.6, 111.0, 103.3, 97.3, 79.3, 79.0, 76.9, 76.9, 74.5, 73.5, 70.6, 69.8, 66.1, 63.0, 61.4, 50.9, 47.1, 46.2, 40.5, 39.4, 39.3, 28.6, 23.5, 21.5, 201, 18.5, 18.0, 14.6, 14.2, 12.7, 12.1. |
| 17 | 2-amino-5-(pyridin-2-yl)-1,3,4-thiadiazole | H | O | 833.72 | 217.7, 205.7, 168.3, 160.1, 154.0, 147.5, 134.6, 126.1, 122.3, 103.2, 79.5, 78.9, 75.9, 75.5, 70.5, 69.7, 66.1, 62.9, 62.0, 51.1, 47.1, 46.2, 40.5, 39.4, 39.3, 28.6, 23.4, 21.5, 20.3, 18.5, 18.0, 14.7, 14.3, 12.5, 12.2 |
| 18 | 5-amino-3-(pyridin-2-yl)isoxazole | H | NC(O)Me | 857 | 205.8, 184.7, 178.0, 169.2, 167.9, 164.6, 154.2, 149.4, 148.6, 136.8, 134.4, 121.1, 103.1, 79.4, 79.3, 76.8, 75.6, 74.7, 73.4, 70.5, 69.8, 66.1, 63.1, 62.8, 50.7, 46.3, 40.5, 38.8, 28.5, 25.3, 23.8, 21.5, 20.3, 19.5, 17.8, |
| 19 | 2-amino-2,3'-bipyridine | H | NC(O)Me | 867 | 205.5, 184.4, 177.6, 167.5, 158.4, 157.9, 153.7, 153.2, 147.5, 138.4, 134.5, 133.7, 121.4, 110.7, 107.6, 102.7, 79.0, 76.4, 75.2, 74.7, 70.2, 69.4, 65.7, 62.7, 50.5, 45.9, 40.1, 38.5, 28.2, 25.0, 23.4, 21.1, 19.3, 17.4, 14.8, 13.8, 13.3, 12.5. |
| 20 | 5-amino-3-(pyridin-2-yl)isoxazole | H | O | 816 | 218.4, 205.5, 169.2, 168.0, 164.7, 153.6, 149.6, 148.6, 137.0, 134.3, 121.1, 103.4, 79.4, 79.3, 79.0, 76.8, 75.9, 74.6, 73.5, 70.6, 69.8, 66.1, 62.9, 61.4, 50.9, 47.2, 46.2, 40.5, 39.4, 39.3, 28.5, 23.5, 21.5, 20.1, 18.5, 18.0, 14.6, 14.2, 12.7, 12.1. |
| 21 | 2-amino-2,3'-bipyridine | H | O | 826 | N/A |

TABLE 6-continued
| Example | Ar | Y | A' | MS (M + H): m/e | Selected $^{13}$C (125 MHz, CDCl$_3$) δ |
|---|---|---|---|---|---|
| 22 | 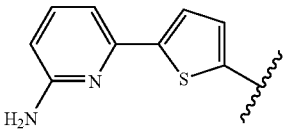 | H | NC(O)Me | 915.5 | 205.9, 184.7, 178.0, 167.8, 157.0, 154.1, 152.6, 149.8, 144.6, 142.4, 139.2, 128.2, 124.5, 112.1, 110.4, 103.1, 79.3, 74.5, 70.8, 70.5, 69.8, 66.1, 63.0, 62.8, 50.8, 46.3, 40.5, 38.8, 29.9, 28.5, 25.4, 23.7, 21.5, 20.3, 19.6, 17.8, 15.1, 14.1, 13.8, 12.9 |
| 23 | 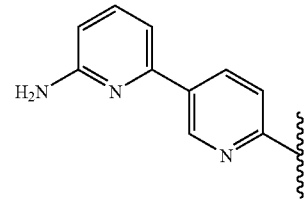 [SMILES: *c1ccc(-c2cccc(N)n2)cn1] | F | NH | 843.37 | 204.5, 204.3, 187.4, 166.1, 166.0, 158.6, 158.0, 154.1, 153.5, 147.9, 138.7, 134.9, 134.1, 121.8, 111.1, 107.9, 104.3, 99.2, 97.5, 81.9, 81.5, 79.9, 76.4, 75.6, 70.6, 69.9, 66.1, 64.7, 62.3, 41.7, 40.8, 40.5, 38.8, 35.2, 28.4, 25.7, 25.5, 22.6, 21.4, 21.2, 20.1, 17.4, 15.5, 13.3, 11.7. |
| 24 | 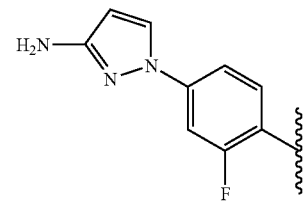 [SMILES: *c1ccc(-n2ccc(N)n2)cc1F] | F | O | 850.4 | 219.3, 205.3, 205.0, 165.1, 165.0, 162.6, 160.6, 156.2, 153.1, 141.3, 141.2, 131.8, 128.0, 121.3, 121.2, 112.6, 105.4, 105.2, 104.2, 99.5, 97.9, 97.1, 80.3, 79.4, 79.3, 76.7, 73.2, 70.6, 69.8, 66.1, 62.4, 61.4, 46.1, 41.0, 40.4, 40.0, 39.7, 29.9, 28.5, 25.3, 25.2. 23.0, 21.4, 20.8, 20.4, 19.0, 17.9, 15.5, 12.3, 11.3. |
| 25 | 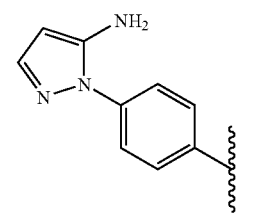 [SMILES: *c1ccc(-n2nccc2N)cc1] | F | NC(O)Me | 873.37 | 205.4, 205.2, 184.2, 165.1, 164.9, 153.9, 145.2, 140.5, 138.3, 137.2, 129.1, 123.9, 117.7, 104.2, 99.7, 98.1, 90.8, 79.7, 76.5, 75.6, 73.6, 70.6, 69.9, 66.0, 63.2, 62.3, 41.3, 40.5, 38.9, 37.5, 28.4, 25.3, 24.6, 24.5, 23.2, 21.4, 21.0, 17.4, 15.0, 14.3, 12.7. |
| 26 | 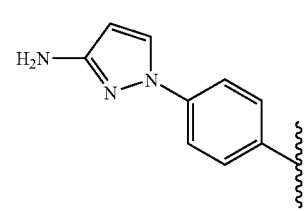 | F | O | 832.4 | N/A. |
| 27 | 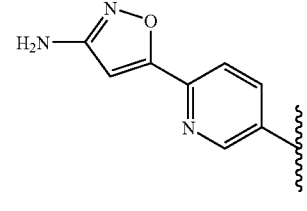 | F | O | 816 | 218.4, 205.6, 169.1, 168.1, 164.1, 153.7, 149.9, 146.2, 137.2, 134.5, 120.4, 103.3, 94.7, 79.4, 78.9, 76.8, 75.9, 74.6, 73.3, 70.5, 69.7, 66.1, 62.8, 61.4, 50.9, 47.2, 46.2, 40.5, 39.4, 39.3, 28.6, 23.5, 21.5, 20.1, 18.5, 18.0, 14.7, 14.2, 12.7, 12.1. |
| 28 | 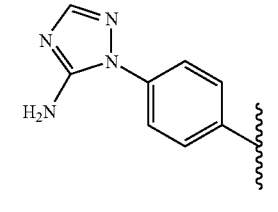 [SMILES: *c1ccc(-n2ncnc2N)cc1] | F | NC(O)Me | 874.5 | N/A. |

TABLE 6-continued

| Example | Ar | Y | A' | MS (M + H): m/e | Selected $^{13}$C (125 MHz, CDCl$_3$) δ |
|---|---|---|---|---|---|
| 29 | 3-amino-1-(4-yl-phenyl)-1,2,4-triazole | F | NC(O)Me | 874.5 | N/A. |
| 30 | 6-amino-pyridin-2-yl-pyrimidin-2-yl | F | NC(O)Me | N/A. | 205.3, 184.2, 166.6, 158.9, 155.5155.3, 154.4, 150.8, 138.8, 130.1, 110.9, 108.7, 103.8, 99.7, 79.7, 76.8, 76.5, 73.7, 70.5, 69.5, 66.3, 63.3, 62.5, 41.2, 40.5, 29.0, 25.3, 24.6, 24.7, 23.2, 21.4, 21.0, 17.4, 15.0, 14.3, 12.6. |
| 31 | 2,4-diamino-pyrimidin-6-yl-(6-methylpyridin-3-yl) | F | NC(O)Me | 901 | 205.36, 184.3, 176.9, 165.1, 164.8, 163.3, 161.7, 159.4, 154.4, 147.8, 135.1, 132.4, 121.7, 104.0, 92.6, 79.7, 76.8, 74.0, 70.6, 69.7, 66.1, 63.1, 62.5, 41.3, 40.5, 39.0, 28.7, 25.3, 24.7, 24.5, 23.2, 21.4, 21.0, 17.6, 15.0, 14.4, 12.6. |
| 32 | 4-amino-thiazol-2-yl-pyridin-2-yl | H | O | 832 | 217.6, 205.6, 168.2, 162.7, 159.6, 157.5, 153.7, 146.7, 133.8, 128.6, 122.1, 103, 91.1, 79.4, 78.9, 76.7, 75.8, 75.3, 70.4, 69.6, 66.2, 62.9, 61.9, 51.0, 46.9, 46.2, 40.5, 39.3, 39.2, 28.8, 23.4, 21.4, 20.2, 18.5, 17.9, 14.5, 14.3, 14.2, 12.4, 12.2 |
| 33 | 4-amino-thiazol-2-yl-pyridin-2-yl | F | O | 850 | 218.8, 205.2, 205.0, 165.1, 165.0, 159.4, 157.5, 153.7, 146.7, 133.7, 128.6, 122.0, 104.2, 99.5, 97.8, 91.1, 80.4, 79.4, 79.3, 76.7, 76.6, 73.5, 70.6, 69.9, 66.0, 62.3, 61.7, 46.0, 41.0, 40.4, 39.9, 39.5, 34.9, 31.8, 28.4, 25.3, 22.9, 22.8, 21.4, 20.8, 18.9, 17.8, 15.4, 14.3, 12.3 |
| 34 | 6-amino-pyridin-2-yl-thiazol-2-yl | H | O | 832 | 218.6, 205.5, 170.6, 167.9, 158.2, 153.5, 149.9, 143.2, 138.7, 136.5, 110.0, 109.8, 103.2, 79.3, 79.0, 76.8, 75.8, 74.3, 70.4, 69.6, 68.4, 66.1, 62.8, 61.3, 50.9, 47.0, 46.3, 40.4, 39.4, 39.2, 28.7, 23.5, 21.4, 20.0, 18.5, 17.9, 14.5, 14.2, 12.7, 12.1 |
| 35 | 5-amino-1,2,4-thiadiazol-3-yl-pyridin-2-yl | H | O | 833 | N/A |
| 36 | 6-amino-pyridin-2-yl-thiazol-5-yl | H | O | 832 | 218.5, 205.5, 168.7, 167.9, 158.4, 154.2, 149.2, 141.3, 139.3, 138.5, 110.1, 107.7, 103.2, 79.4, 78.8, 76.8, 75.8, 74.5, 73.3, 70.5, 69.7, 66.1, 62.8, 61.4, 50.9, 47.0, 46.2, 40.4, 39.5, 39.2, 28.6, 23.5, 21.4, 20.0, 18.5, 17.9, 14.5, 14.2, 12.5, 12.1 |
| 37 | 6-amino-pyridin-2-yl-thiazol-5-yl | H | NC(O)Me | 873.46 | 205.8, 184.6, 178.0, 170.5, 167.7, 158.2, 154.1, 149.9, 143.0, 138.7, 136.7, 110.0, 109.8, 102.9, 79.4, 79.1, 76.7, 74.5, 70.4, 69.5, 68.4, 66.2, 63.0, 62.7, 50.7, 46.1, 40.4, 38.7, 28.8, 25.3, 23.8, 21.4, 20.2, 19.4, 17.7, 15.0, 14.1, 13.5, 13.0 |

TABLE 6-continued
| Example | Ar | Y | A' | MS (M + H): m/e | Selected $^{13}$C (125 MHz, CDCl$_3$) δ |
|---|---|---|---|---|---|
| 38 | 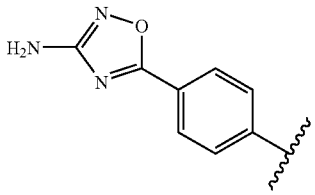 | F | O | 834.54 | 219.1, 205.3, 205.0, 174.8, 168.7, 165.2, 165.0, 153.4, 143.1, 128.4, 128.1, 123.7, 104.1, 99.5, 97.9, 80.3, 79.5, 79.2, 76.7, 75.5, 73.3, 70.6, 69.8, 66.1, 62.3, 61.5, 46.1, 41.0, 40.5, 39.9, 39.5, 28.6, 25.3, 25.1, 23.0, 21.4, 20.8, 18.9, 17.9, 15.5, 12.4, 11.3. |
| 39 | 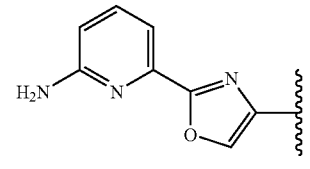 [SMILES: *c1coc(-c2cccc(N)n2)n1] | H | O | 816 | 217.7, 205.3, 167.8, 160.7, 158.4, 153.0, 144.3, 139.1, 138.3, 137.7, 112.4, 110.0, 102.9, 79.0, 78.7, 76.5, 75.5, 74.7, 70.2, 69.5, 68.3, 65.8, 62.7, 61.4, 50.7, 46.7, 45.9, 40.2, 39.1, 28.2, 23.2, 21.2, 19.9, 18.2, 17.6, 14.2, 13.9, 12.3, 11.9. |
| 40 | 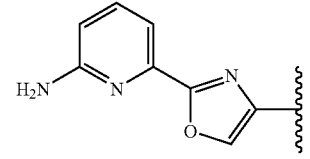 [SMILES: *c1coc(-c2cccc(N)n2)n1] | H | NC(O)Me | 857 | 205.6, 184.4, 177.7, 167.5, 160.7, 158.4, 153.5, 144.3, 139.0, 138.3, 137.4, 112.5, 110.1, 102.7, 79.1, 78.9, 76.4, 75.2, 74.3, 70.2, 69.5, 68.1, 65.8, 62.8, 50.4, 45.9, 40.2, 38.5, 28.2, 25.1, 23.5, 21.2, 20.0, 19.2, 17.5, 14.8, 13.8, 13.3, 12.6. |
| 41 | 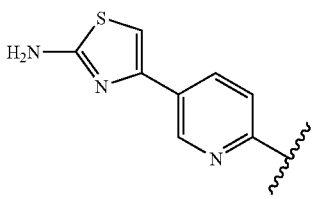 | H | O | 832 | 127.9, 205.7, 168.2, 168.0, 157.0, 153.4, 148.5, 147.2, 133.8, 129.6, 122.1, 103.7, 103.2, 79.4, 78.9, 76.8, 76.7, 75.8, 75.1, 70.5, 69.7, 66.1, 62.9, 61.8, 51.0, 47.0, 46.1, 40.4, 39.4, 39.2, 28.5, 23.4, 21.4, 20.1, 18.5, 17.9, 14.6, 14.2, 12.5, 12.2. |
| 42 | 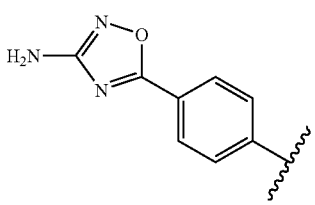 [SMILES: *c1ccc(-c2nc(N)no2)cc1] | H | O | 816 | 218.2, 205.5, 174.8, 168.7, 168.0, 153.4, 143.2, 128.5, 128.1, 123.7, 103.1, 79.3, 78.9, 76.8, 75.8, 75.4, 74.8, 70.4, 69.6, 66.1, 62.9, 61.5, 50.9, 47.1, 46.2, 40.4, 39.4, 39.3, 28.8, 23.5, 21.4, 20.1, 18.5, 18.0, 14.6, 14.2, 12.6, 12.1. |
| 43 | 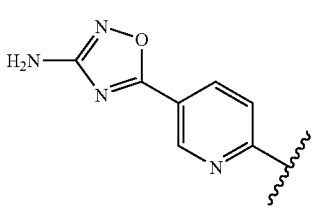 [SMILES: *c1ccc(-c2nc(N)no2)cn1] | F | O | 836 | 218.6, 205.1, 204.9, 173.1, 168.7, 165.3, 165.1, 163.2, 163.0, 154.1, 148.6, 148.4, 143.4, 140.8, 135.9, 135.7, 122.2, 121.9, 119.5, 103.6, 99.5, 97.9, 80.8, 80.4, 79.5, 79.3, 76.5, 73.8, 70.4, 69.5, 66.5, 62.3, 61.8, 46.1, 41.0, 40.6, 39.9, 39.5, 36.8, 29.5, 25.3, 25.1, |
| 44 | 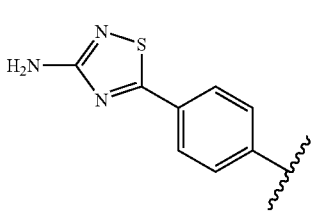 [SMILES: *c1ccc(-c2nc(N)ns2)cc1] | H | O | 833 | N/A |

TABLE 6-continued
| Example | Ar | Y | A' | MS (M + H): m/e | Selected $^{13}$C (125 MHz, CDCl$_3$) δ |
|---|---|---|---|---|---|
| 45 | 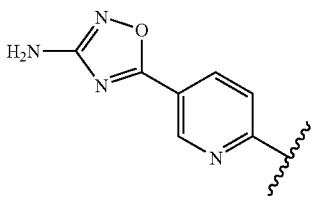 [SMILES: *c1ccc(-c2nc(N)no2)cn1] | H | O | 817 | 217.3, 205.6, 173.1, 168.7, 168.3, 163.0, 154.1, 148.6, 135.8, 122.1, 119.5, 102.8, 79.5, 78.9, 76.7, 76.5, 75.9, 75.8, 70.3, 69.3, 66.4, 62.9, 62.1, 51.0, 46.9, 46.2, 40.5, 39.3, 39.2, 29.4, 23.4, 21.3, 20.2, 18.5, 17.9, 14.5, 14.3, 12.4, 12.2. |
| 46 | 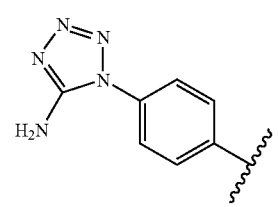 [SMILES: *c1ccc(-n2nnnc2N)cc1] | H | O | 816 | 218.1, 205.6, 168.2, 154.4, 153.7, 140.5, 132.6, 129.9, 123.9, 110.0, 103.2, 79.4, 79.0, 76.8, 75.9, 75.1, 75.0, 70.5, 69.6, 66.1, 62.9, 61.6, 51.0, 47.2, 46.2, 40.4, 39.3, 28.8, 23.5, 21.4, 20.1, 18.5, 18.0, 14.7, 14.2, 12.6, 12.1. |
| 47 | 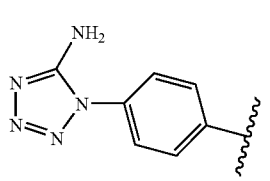 [SMILES: *c1ccc(-n2nnnc2N)cc1] | H | NC(O)Me | 857 | 205.8, 184.8, 177.7, 168.0, 154.5, 154.2, 140.6, 132.6, 129.7, 123.9, 103.0, 79.4, 79.3, 76.7, 75.5, 75.1, 75.0, 70.4, 69.6, 66.1, 63.0, 50.7, 46.3, 40.2, 38.7, 28.7, 25.3, 23.8, 21.4, 20.3, 19.6, 17.8, 15.1, 14.1, 13.7, 12.9. |
| 48 | 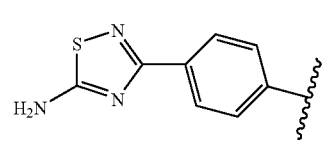 [SMILES: *c1ccc(-c2nsc(N)n2)cc1] | H | NC(O)Me | 873 | N/A |
| 49 | 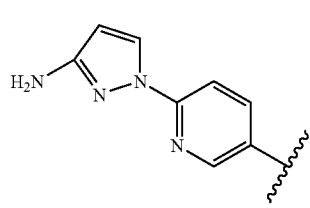 | F | O | 833 | N/A |
| 50 | 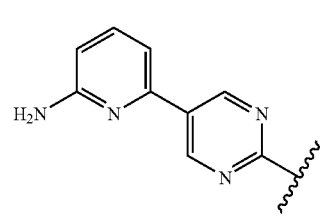 | H | O | 827 | N/A |
| 51 | 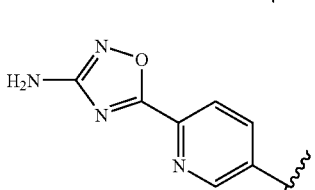 | H | O | 817.4 | 218.2, 205.5, 173.5, 168.8, 168.2, 154.0, 150.3, 142.9, 137.1, 123.6, 110.0, 103.1, 79.4, 78.9, 76.8, 75.9, 74.8, 73.0, 70.4, 69.4, 66.1, 62.8, 61.4, 50.9, 47.1, 46.2, 40.2, 39.3, 39.2, 29.0, 23.5, 21.4, 20.1, 18.5, 18.0, 14.6, 14.2, 12.6, 12.1. |
| 52 | 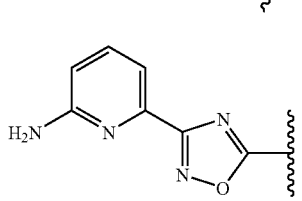 | F | O | 835.5 | 219.3, 205.2, 205.0, 176.3, 168.5, 165.2, 165.0, 158.9, 155.0, 144.5, 138.6, 113.9, 111.4, 104.0, 99.6, 97.9, 80.4, 79.5, 79.0, 76.8, 73.3, 70.5, 69.6, 66.8, 66.1, 62.1, 61.3, 46.1, 41.1, 40.4, 39.9, 39.5, 28.8, 25.2, 25.1, 23.0, 21.4, 20.7, 18.8, 17.9, 15.4, 12.4, 11.3. |

TABLE 6-continued
| Example | Ar | Y | A' | MS (M + H): m/e | Selected $^{13}$C (125 MHz, CDCl$_3$) δ |
|---|---|---|---|---|---|
| 53 | 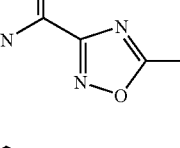 | H | O | 817.45 | 218.6, 205.5, 176.4, 168.5, 168.0, 158.9, 155.0, 144.6, 138.6, 114.0, 111.4, 103.0, 79.4, 79.0, 76.8, 75.7, 74.5, 70.4, 69.4, 66.8, 66.2, 62.6, 61.2, 50.9, 47.0, 46.2, 40.3, 39.4, 39.2, 29.0, 23.6, 21.4, 20.0, 18.5, 18.0, 14.5, 14.2, 12.7, 12.1. |
| 54 | 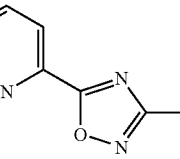 | H | O | 817.11 | 218.6, 205.5, 175.2, 168.3, 168.0, 159.2, 154.3, 141.7, 138.6, 114.7, 112.8, 103.2, 79.4, 79.0, 76.8, 75.7, 74.5, 70.5, 67.2, 66.1, 62.7, 61.3, 50.9, 46.9, 46.2, 40.4, 39.5, 39.3, 28.5, 23.6, 21.5, 20.0, 18.5, 17.9, 14.5, 14.2, 12.6, 12.1. |
| 55 | 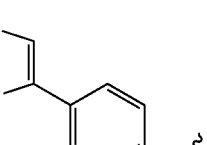 | H | O | 816 | 217.6, 205.6, 168.1, 160.7, 157.4, 153.4, 146.3, 137.6, 133.1, 128.2, 126.5, 122.1, 102.7, 79.3, 78.9, 76.8, 76.7, 75.8, 75.3, 70.3, 69.2, 66.5, 62.9, 61.9, 51.0, 46.7, 46.1, 40.5, 39.4, 39.2, 29.9, 29.6, 23.4, 21.3, 20.1, 18.5, 17.9, 14.4, 14.3, 12.4, 12.2 |
| 56 | 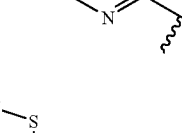 | F | O | 850 | N/A |
| 57 | 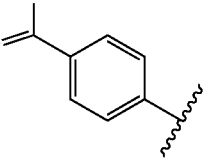 | F | NC(O)Et | 888 | 207.8, 205.1, 204.9, 187.3, 157.3, 153.2, 150.2, 141.7, 140.0, 126.6, 119.4, 105.6, 103.9, 101.3, 99.5, 97.9, 79.6, 79.4, 76.3, 73.3, 70.4, 69.6, 67.2, 65.8, 62.8, 62.4, 41.0, 40.2, 31.0, 28.1, 24.3, 24.2, 22.9, 21.2, 17.1, 14.7, 14.2. |
| 58 | 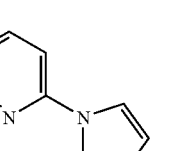 | H | O | 815 | 218.3, 205.3, 167.6, 157.3, 152.4, 150.2, 142.0, 140.0, 126.9, 119.4, 105.5, 103.0, 101.3, 79.0, 78.7, 76.6, 75.6, 74.1, 70.3, 69.5, 67.1, 65.8, 62.7, 61.1, 50.7, 46.8, 45.9, 40.2, 39.3, 39.0, 28.2, 23.2, 21.2, 19.8, 18.3, 17.7, 14.3. |
| 59 | 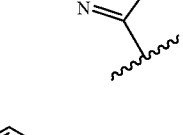 | F | NC(O)Me | 856 | 205.6, 184.4, 177.8, 67.5, 157.3, 153.0, 150.2, 141.8, 140.0, 126.7, 119.4, 105.5, 102.8, 101.3, 79.1, 78.9, 76.5, 74.3, 70.2, 69.4, 67.1, 65.8, 62.9, 62.5, 50.5, 46.0, 40.2, 38.5, 28.2, 25.1, 23.5, 21.2, 20.1, 19.3, 17.5, 14.8, 13.8, 13.4, 12.6. |

TABLE 6-continued

| Example | Ar | Y | A' | MS (M + H): m/e | Selected $^{13}$C (125 MHz, CDCl$_3$) δ |
|---|---|---|---|---|---|
| 60 | [oxazol-2-amine linked to pyridine] | H | O | 816 | 218.4, 205.5, 168.0, 160.4, 153.3, 150.6, 149.7, 140.4, 137.2, 132.1, 131.0, 119.6, 103.0, 79.2, 79.0, 76.8, 75.8, 74.6, 73.6, 70.4, 69.4, 66.3, 62.9, 61.4, 50.9, 47.0, 46.2, 40.5, 39.4, 39.2, 29.1, 23.5, 21.4, 20.0, 18.5, 17.9, 14.5, 14.2, 12.6, 12.1 |
| 61 | [1,2,4-thiadiazol-3-amine linked to pyridine] | H | O | 833 | N/A |
| 62 | [1,2,4-oxadiazol-5-amine linked to pyridine] | H | O | 817 | 218.3, 205.6, 172.1, 168.4, 168.2, 153.8, 150.0, 146.2, 136.9, 135.5, 122.4, 102.9, 79.4, 79.0, 76.8, 75.9, 74.9, 73.3, 70.4, 69.4, 66.3, 62.9, 61.5, 51.0, 47.1, 46.2, 40.6, 39.4, 39.3, 29.4, 23.5, 21.4, 20.1, 18.5, 18.0, 14.6, 14.3, 12.6, 12.1. |
| 63 | [aminopyridine linked to thiazole] | H | O | 832 | 218.6, 205.6, 167.9, 167.7, 158.3, 155.7, 154.3, 151.2, 138.8, 117.2, 111.9, 108.3, 103.3, 79.4, 78.9, 76.8, 75.9, 74.5, 73.2, 70.5, 69.8, 66.1, 62.7, 61.5, 51.0, 47.1, 46.2, 40.5, 39.5, 39.3, 29.9, 28.5, 23.5, 21.5, 20.1, 18.5, 17.9, 14.7, 14.2, 12.6, 12.1. |
| 64 | [1,2,4-thiadiazol-3-amine linked to pyrazine] | F | O | 852 | N/A |
| 65 | [aminopyridine linked to oxazole] | F | NC(O)Et | 889 | 205.1, 204.9, 187.2, 161.2, 158.5, 154.2, 148.7, 144.2, 138.2, 128.1, 113.3, 110.1, 103.9, 99.5, 97.9, 79.4, 76.4, 73.4, 70.4, 69.6, 65.8, 62.7, 62.3, 41.1, 40.2, 34.6, 31.5, 31.0, 28.1, 25.2, 24.3, 22.9, 22.6, 21.2, 20.6, 17.2, 14.7. |
| 66 | [aminopyridine linked to oxazole] | H | O | 816 | 218.4, 205.3, 167.6, 161.2, 158.5, 153.4, 148.9, 144.1, 138.3, 128.2, 112.3, 110.2, 103.0, 79.0, 78.7, 76.3, 76.5, 75.6, 74.0, 70.2, 69.5, 65.7, 65.6, 62.5, 60.9, 50.6, 46.8, 45.9, 40.2, 39.2, 39.0, 29.6, 28.2, 23.3, 21.2, 19.7, 18.2. |

TABLE 6-continued

| Example | Ar | Y | A' | MS (M + H): m/e | Selected $^{13}$C (125 MHz, CDCl$_3$) δ |
|---|---|---|---|---|---|
| 67 | H$_2$N-[5-amino-1,2,4-thiadiazol-3-yl]-pyrazin-2-yl | F | NC(O)Et | 907 | N/A |
| 68 | H$_2$N-[5-amino-1,2,4-thiadiazol-3-yl]-pyrazin-2-yl | H | O | 834 | N/A |
| 69 | pyridin-2-yl | F | NC(O)Et | 807 | N/A |
| 70 | H$_2$N-pyridin-6-yl-oxazol-5-yl | H | NC(O)Me | 857 | N/A |
| 71 | H$_2$N-pyridin-6-yl-thiazol-4-yl | H | O | 832 | 217.9, 205.4, 169.3, 167.8, 157.9, 154.4, 153.0, 149.6, 138.5, 118.6, 110.2, 109.6, 102.9, 79.1, 78.7, 76.5, 75.5, 74.6, 72.1, 70.3, 69.5, 65.8, 62.7, 61.4, 50.7, 46.7, 45.9, 40.2, 39.2, 39.0, 29.7, 28.2, 23.3, 21.2, 19.9, 18.3, 17.6. |
| 72 | H$_2$N-pyridin-6-yl-thiazol-4-yl | F | O | 850 | N/A |
| 73 | H$_2$N-pyrazin-yl-thiazol-2-yl | H | O | 833 | N/A |
| 74 | H$_2$N-pyridin-6-yl-pyridin-5-yl | F | NC(O)Me | 885 | 205.0, 204.8, 183.9, 158.4, 153.9, 153.2, 147.5, 138.4, 134.5, 133.7, 121.2, 110.7, 107.7, 103.8, 79.4, 76.5, 73.4, 70.4, 69.6, 65.7, 47.1, 41.2, 41.0, 40.2, 30.5, 28.2, 28.1, 25.0, 24.3, 22.9, 21.1, 20.7, 17.1, 14.7, 14.0, 12.3. |

TABLE 6-continued

| Example | Ar | Y | A' | MS (M + H): m/e | Selected $^{13}$C (125 MHz, CDCl$_3$) δ |
|---|---|---|---|---|---|
| 75 | 6-amino-pyridin-2-yl-pyridin-2-yl | F | NC(O)Et | 899 | 205.1, 204.8, 187.3, 176.9, 164.7, 158.4, 158.0, 154.0, 153.3, 147.6, 138.5, 134.6, 133.7, 121.2, 110.8, 107.7, 103.9, 99.5, 97.9, 80.1, 79.4, 76.5, 76.3, 73.5, 70.4, 69.6, 65.8, 63.0, 62.3, 41.1, 40.9, 40.2, 38.8, 31.6, 29.7, 28.2, 24.3 |
| 76 | 6-amino-pyridin-2-yl-pyridin-2-yl | F | NC(O)-propyl | 913 | 205.0, 204.8, 176.6, 164.7, 164.5, 158.4, 158.0, 154.0, 153.3, 147.6, 138.5, 134.5, 133.7, 121.2, 110.8, 107.7, 103.9, 99.5, 97.9, 80.0, 79.4, 76.5, 76.3, 73.5, 70.4, 19.6, 65.8, 63.0, 62.3, 41.1, 40.2, 39.9, 38.8, 29.7, 28.2, 24.3, 24.1 |
| 77 | 6-amino-pyridin-2-yl-pyridin-2-yl | F | NC(O)-cyclo-pro-pyl | 911 | N/A |
| 78 | 3-amino-pyrazol-1-yl-pyridin-2-yl | F | NC(O)Me | 874 | N/A |
| 79 | 3-amino-pyrazol-1-yl-pyridin-2-yl | F | NC(O)Et | 888 | 205.1, 204.9, 187.3, 164.8, 164.7, 156.4, 153.8, 151.0, 147.8, 138.8, 129.4, 128.4, 110.7, 104.0, 99.6, 97.9, 97.1, 79.4, 76.3, 73.4, 73.2, 70.4, 69.6, 65.9, 62.9, 62.5, 41.2, 40.2, 38.8, 31.0, 29.7, 28.2, 24.3, 24.1, 23.0, 21.2, 20.6, 17.1, 14.7, 14.2, 12.5, 8.7 |
| 80 | 6-amino-pyridin-2-yl-pyridin-2-yl | F | NC(O)-isopropyl | 913 | 205.4, 205.1, 190.3, 158.7, 158.3, 154.3, 153.6, 147.8, 138.7, 134.8, 134.0, 121.4, 111.0, 108.0, 104.2, 99.8, 98.2, 80.3, 79.7, 76.7, 76.6, 73.8, 70.6, 69.9, 66.1, 63.2, 62.6, 41.4, 40.5, 39.2, 37.5, 28.4, 24.5, 24.4, 23.2, 21.5, 21.3, 20.0, 18.8, 17.3, 14.9, 14.6, 14.4, 12.7. |
| 81 | 3-amino-pyrazol-1-yl-phenyl | F | NC(O)Me | 873.35 | 205.1, 204.9, 183.9, 164.6, 155.7, 153.4, 139.6, 134.5, 129.1, 127.7, 117.5, 103.9, 99.5, 97.9, 96.1, 79.4, 76.3, 75.5, 73.4, 70.4, 69.6, 65.8, 63.0, 62.4, 41.0, 40.7, 38.8, 28.2, 25.1, 24.4, 24.2, 22.9, 21.2, 20.8, 17.1, 14.8, 14.1, 12.4. |

TABLE 6-continued
| Example | Ar | Y | A' | MS (M + H): m/e | Selected $^{13}$C (125 MHz, CDCl$_3$) δ |
|---|---|---|---|---|---|
| 82 | 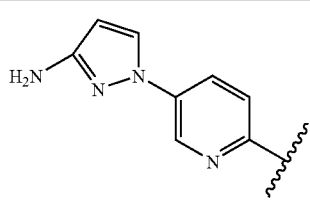 [SMILES: *c1ccc(-n2ccc(N)n2)cn1] | F | NC(O)Me | 874 | 205.3, 205.1, 184.2, 165.0, 164.8, 156.6, 154.5, 154.3, 138.7, 135.7, 128.0, 125.4, 122.3, 104.1, 97.3, 79.7, 76.5, 73.7, 70.6, 69.8, 66.0, 63.2, 62.5, 41.3, 40.5, 39.0, 37.5, 28.4, 25.3, 24.6, 24.4, 23.2, 21.4, 21.0, 17.4, 15.0, 14.3, 12.6. |
| 83 | 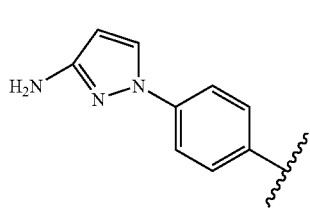 | H | NC(O)Et | 887 | 205.3, 205.1, 187.6, 164.8, 165.0, 156.0, 153.7, 139.8, 134.7, 129.3, 127.9, 117.8, 104.1, 99.8, 99.1, 96.4, 79.8, 76.6, 75.7, 73.7, 70.6, 69.7, 66.1, 63.2, 62.7, 53.7, 51.0, 41.3, 40.5, 31.3, 28.7, 24.6, 24.4, 23.2, 21.4, 20.9, 17.4 |
| 84 | 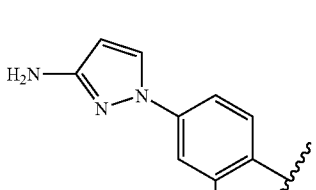 | H | NC(O)Me | 873 | 205.9, 184.8, 178.0, 167.8, 162.5, 160.5, 156.2, 153.7, 141.3, 141.2, 131.7, 128.0, 121.5, 121.4, 112.6, 112.5, 105.4, 105.2, 103.0, 97.0, 79.3, 76.7, 75.6, 74.7, 70.5, 69.7, 66.1, 63.1, 62.8, 50.8, 46.2, 40.4, 38.8, 37.3, 28.5, 25.4, 23.8, 21.5, 20.3, 19.6, 17.8, 15.1, |
| 85 | 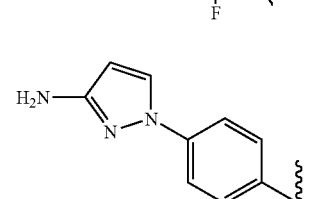 | F | NC(O)Me | 891.41 | 205.4, 205.1, 184.2, 165.1, 164.9, 162.5, 160.5, 156.2, 153.9, 141.2, 131.5, 128.0, 121.3, 112.6, 105.4, 105.2, 104.2, 99.7, 98.1, 97.1, 79.6, 76.5, 73.6, 70.7, 69.9, 66.0, 63.1, 62.6, 41.3, 40.5, 39.0, 28.4, 25.3, 24.7, 24.5, 23.2, 21.5, 21.0, 17.4, 15.0, 14.3, 12.6. |
| 86 | 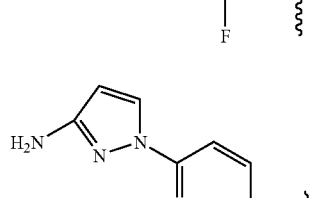 | F | NC(O)-isopropyl | 902 | :205.4, 205.2, 190.2, 176.9, 165.1, 164.9, 156.6, 154.1, 151.2, 148.0, 139.0, 129.6, 128.6, 111.0, 104.2, 97.3, 80.3, 79.8, 79.7, 76.6, 73.7, 73.4, 70.6, 69.9, 66.1, 63.1, 62.7, 41.4, 40.5, 39.1, 37.5, 30.0, 28.5, 24.5, 24.4, 23.2, 21.5, 21.2, 20.7, 20.0, 18.8, 17.4, 15.0, 14.5, 1 |
| 87 | 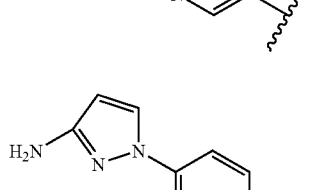 | F | NC(O)-isopropyl | 902 | 13C(CDCl3): 205.4, 205.1, 190.3, 177.0, 164.9, 164.8, 156.6, 154.7, 154.4, 138.8, 135.7, 128.0, 125.5, 122.2, 104.2, 97.3, 80.3, 79.8, 79.7, 76.6, 76.5, 73.7, 70.6, 69.9, 66.1, 63.2, 62.6, 41.4, 40.5, 39.1, 37.5, 29.9, 28.5, 24.5, 24.4, 23.2, 21.5, 21.2, 20.7, 20.0, 18.8, 17.3, 15.0, 14.6, 12.7 |
| 88 | 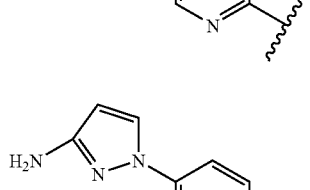 | H | NC(O)Me | 889 | N/A |

TABLE 6-continued

| Example | Ar | Y | A' | MS (M + H): m/e | Selected $^{13}$C (125 MHz, CDCl$_3$) δ |
|---|---|---|---|---|---|
| 89 | 3-amino-pyrazol-1-yl attached to 3-chloro-phenyl | F | NC(O)Me | 907.5 | N/A. |
| 90 | 3-amino-pyrazol-1-yl attached to phenyl | H | NC(O)-isopropyl | 883 | 205.9, 190.7, 178.3, 167.7, 155.9, 153.6, 139.7, 135.0, 129.3, 128.0, 117.7, 103.1, 96.3, 79.3, 79.1, 76.8, 75.8, 75.6, 74.5, 70.5, 69.7, 66.1, 63.1, 62.9, 50.7, 46.3, 40.5, 39.0, 37.4, 28.5, 23.8, 21.5, 210.2, 19.8, 19.3, 18.8, 17.8, 15.3, 14.1, 13.7, 12.9. |
| 91 | 3-amino-pyrazol-1-yl attached to phenyl | F | NC(O)-isopropyl | 901 | 205.4, 205.2, 176.9, 165.0, 164.8, 155.9, 153.8, 139.8, 134.8, 129.2, 127.9, 117.8, 104.2, 96.4, 80.2, 79.8, 76.6, 75.7, 73.6, 70.7, 69.9, 66.1, 63.2, 62.7, 41.4, 40.5, 39.2, 37.5, 28.4, 24.6, 24.4, 23.2, 21.5, 21.2, 20.7, 20.0, 18.8, 17.3, 15.0, 14.5, 12.7. |
| 92 | 3-amino-pyrazol-1-yl attached to pyridyl | F | NC(O)Et | 888 | 205.4, 205.1, 187.6, 177.2, 165.0, 164.8, 156.8, 154.5, 154.3, 138.6, 135.7, 128.1, 125.6, 122.4, 103.9, 99.7, 98.1, 97.3, 80.3, 79.6, 76.5, 76.4, 73.7, 70.5, 69.4, 66.0, 63.1, 62.6, 41.3, 40.1, 39.0, 37.5, 31.3, 29.9, 28.9, 25.6, 25.4, 23.2, 21.4, 20.9, 17.4, 15.0, 14.4, |
| 93 | 3-amino-pyrazol-1-yl attached to phenyl | F | NC(O)-cyclopropyl | 899 | N/A |
| 94 | 3-amino-pyrazol-1-yl attached to pyridyl | F | NC(O)-cyclopropyl | 900 | N/A |
| 95 | 3-amino-pyrazol-1-yl attached to 2-fluoro-phenyl | F | NC(O)Me | 891 | 205.4, 205.2, 184.2, 165.1, 155.6, 154.0, 153.9, 151.9, 136.4, 132.4, 132.3, 127.8, 124.4, 116.4, 116.2, 104.2, 99.7, 98.1, 96.6, 79.7, 75.0, 73.7, 70.7, 69.9, 66.0, 63.2, 6.4, 41.3, 40.5, 28.4, 25.3, 24.6, 24.5, 21.4, 17.4, 15.0, 14.3, 12.7, |
| 96 | 3-amino-4-vinyl-pyrazol-1-yl attached to pyridyl | F | NC(O)Me | 900 | 205.4, 184.2, 165.0, 154.3, 138.7, 135.4, 125.9, 125.4, 125.2, 122.3, 113.2, 110.9, 104.1, 99.8, 79.7, 73.7, 70.7, 69.9, 66.0, 62.5, 41.3, 40.5, 39.0, 28.4, 28.1, 25.3, 24.6, 24.4, 23.2, 21.4, 21.0, 17.4, 15.0, 14.3, 13.8, 12.6, |

TABLE 6-continued

| Example | Ar | Y | A' | MS (M + H): m/e | Selected $^{13}$C (125 MHz, CDCl$_3$) δ |
|---|---|---|---|---|---|
| 97 | 6-amino-pyridin-2-yl-thiazol-5-yl | F | NC(O)Me | 891.55 | 205.3, 205.1, 184.1, 176.9, 170.6, 165.0, 164.8, 158.2, 154.3, 149.8, 143.0, 138.8, 138.6, 136.4, 109.9, 104.1, 99.6, 98.0, 79.9, 76.5, 73.5, 70.6, 69.72, 69.67, 68.5, 65.9, 63.0, 62.5, 54.0, 41.2, 40.3, 38.9, 31.9, 29.8, 29.4, 28.4, 25.2, 24.5, 24.4, 23.1, 21.4, 21.2, 20.9, 17.3, 14.94, 14.92, 14.2, 12.7 |
| 98 | 3-amino-pyrazol-1-yl-(3-fluorophenyl) | F | NC(O)-isopropyl | 901 | 205.9, 190.7, 178.3, 171.4, 167.6, 162.5, 160.5, 156.2, 153.8, 113.6, 128.0, 112.5, 105.4, 105.2, 97.0, 79.3, 76.8, 74.5, 70.4, 69.6, 69.3, 66.3, 63.1, 62.7, 60.6, 50.7, 40.5, 37.4, 29.9, 29.2, 23.8, 21.4, 21.3, 20.2, 19.8, 19.3, 18.8, 17.8 |
| 99 | 3-amino-pyrazol-1-yl-(3-methoxyphenyl) | F | NC(O)Me | 903 | 205.3, 205.0, 184.3, 171.4, 158.3, 155.9, 153.4, 141.0, 128.1, 108.8, 103.9, 101.3, 96.4, 79.7, 73.6, 71.2, 70.5, 69.6, 69.2, 62.7, 60.6, 55.8, 41.2, 40.5, 41.2, 40.5, 25.3, 23.2, 21.4, 21.3, 21.0, 17.3, 15.0, 14.4, 12.5. |
| 100 | 6-amino-pyridin-2-yl-pyrimidin-2-yl | F | NC(O)-isopropyl | 914 | 205.4, 205.1, 190.2, 177.0, 166.6, 165.0, 164.8, 158.9, 155.4, 154.5, 150.8, 138.8, 130.9, 110.8, 108.7, 104.0, 99.8, 98.2, 80.3, 79.7, 76.8, 76.7, 76.6, 76.5, 73.7, 70.6, 69.6, 66.2, 63.3, 62.6, 41.3, 40.5, 39.2, 37.5, 29.9, 28.8, 24.6, 24.4, 23.2, 21.4, 21.3, 20.7, 19.9, 18.9, |
| 101 | 4-amino-thiazol-2-yl-pyridin-5-yl | F | NC(O)Me | 891 | 205.1, 204.9, 184.0, 176.8, 164.8, 164.6, 162.4, 159.2, 157.3, 154.2, 146.5, 133.5, 128.4, 121.4, 103.9, 99.5, 97.9, 90.9, 79.4, 76.6, 76.3, 73.5, 70.4, 69.6, 67.1, 65.8, 62.9, 62.3, 41.0, 40.2, 29.7, 28.2, 25.1, 24.3, 24.2, 23.0, 21.2, 20.7, 17.1, 14.7, 14.0, 12.4 |
| 102 | 4-amino-pyrimidin-2-yl-pyridin-5-yl | F | NC(O)Me | 886 | 205.6, 184.3, 176.9, 165.0, 163.5, 162.7, 159.5, 156.2, 154.2, 149.4, 136.2, 132.9, 121.5, 104.0, 103.9, 98.9, 80.3, 79.8, 76.6, 73.7, 70.5, 69.6, 66.1, 63.2, 62.6, 41.2, 40.5, 38.9, 37.5, 28.9, 25.3, 24.7, 24.6, 23.3, 21.4, 21.0, 17.4, 15.1, 14.3, 12.7. |
| 103 | 6-amino-pyridin-2-yl-pyrazin-5-yl | F | NC(O)Me | 886 | 205.3, 205.1, 184.1, 177.0, 165.0, 164.8, 158.3, 154.7, 152.8, 152.5, 150.3, 142.5, 142.3, 138.8, 112.0, 109.7, 104.1, 99.7, 98.1, 79.7, 76.5, 75.0, 73.7, 70.6, 69.8, 66.0, 63.0, 62.5, 41.3, 40.4, 38.9, 29.5, 28.4, 25.3, 24.5, 24.4, 23.2, 21.4, 20.9, 17.4, 14.9, 14.3, 12.6. |
| 104 | 2-amino-thiazol-4-yl-pyridin-5-yl | F | NC(O)Me | 891 | 205.2, 205.0, 184.0, 167.8, 167.7, 164.8, 164.6, 156.7, 153.9, 148.3, 147.0, 133.5, 129.3, 121.5, 103.9, 103.6, 99.5, 97.9, 80.1, 79.7, 79.5, 76.6, 76.5, 73.5, 70.4, 70.3, 69.6, 65.8, 62.9, 62.3, 41.0, 40.2, 38.7, 28.1, 25.1, 24.4, 24.2, 23.0, 21.2, 20.8, 17.1, 17.0, 14.8, 14.0, 12.4 |

TABLE 6-continued

| Example | Ar | Y | A' | MS (M + H): m/e | Selected $^{13}$C (125 MHz, CDCl$_3$) δ |
|---|---|---|---|---|---|
| 105 | 4-amino-pyrimidin-2-yl-phenyl | F | NC(O)Me | 885 | 205.2, 184.2, 177.0, 165.0, 164.6, 163.2, 156.6, 153.7, 140.1, 137.6, 128.2, 127.9, 103.6, 98.9, 79.7, 76.5, 76.0, 73.6, 70.5, 69.6, 66.2, 63.2, 62.6, 41.2, 40.5, 39.0, 28.9, 25.3, 24.7, 24.5, 23.2, 21.4, 21.0, 17.4, 15.0, 14.3, 12.6. |
| 106 | 6-amino-pyridin-2-yl-thiazol-2-yl | F | NC(O)Me | 891 | 205.3, 205.1, 184.2, 176.9, 168.6, 165.0, 164.8, 158.5, 155.0, 149.1, 141.2, 139.2, 138.6, 110.1 107.7, 104.1, 99.7, 98.1, 80.3, 79.7, 76.5, 73.7, 73.3, 70.6, 69.6, 66.0, 63.1, 62.5, 41.3, 40.4, 38.9, 37.5, 29.9, 28.4, 25.3, 24.6, 24.4, 23.2, 21.4, 21.2, 20.9, 17.3, 14.9, 14.3, |
| 107 | 5-amino-1,2,4-thiadiazol-3-yl-pyridin-2-yl | F | NC(O)Me | 892 | 206.9, 206.7, 184.3, 183.8, 176.6, 166.9, 165.2, 165.0, 157.4, 153.5, 135.4, 128.9, 123.1, 104.1, 99.3, 97.7, 80.0, 79.5, 76.3, 76.1, 73.4, 70.4, 69.7, 65.8, 62.7, 62.3, 40.9, 40.2, 38.7, 37.2, 29.7, 28.1, 25.0, 24.9, 24.7, 21.1, 20.9, 20.7, 17.2, 15.0, 14.1, 12.7 |
| 108 | 4-amino-thiazol-2-yl-pyridin-2-yl | H | NC(O)Me | 873 | 207.8, 205.5, 184.5, 177.6, 167.5, 162.4, 159.3, 157.3, 153.9, 146.5, 133.4, 128.3, 121.6, 102.7, 90.8, 79.0, 76.4, 76.2, 74.7, 70.2, 69.5, 65.8, 62.7, 50.5, 45.9, 40.2, 38.5, 28.2, 25.1, 23.5, 21.2, 20.0, 19.3, 17.5, 14.9, 13.8, 13.3, 12.5 |
| 109 | 4-amino-thiazol-2-yl-pyridin-2-yl | F | NC(O)-isopropyl | 919 | 205.1, 204.9, 190.0, 164.7, 164.5, 162.4, 159.3, 154.3, 146.5, 133.4, 128.3, 121.3, 103, 9, 99.5, 97.9, 90.9, 80.1, 76.3, 76.2, 73.5, 70.4, 69.2, 65.8, 62.9, 62.3, 41.1, 40.2, 38.9, 37.3, 29.7, 28.1, 24.3, 24.1, 23.0, 21.2, 20.9, 20.4, 19.7, 18.5, 17.1, 14.6, 14.3, 12.4 |
| 110 | 6-amino-pyridin-2-yl-thiazol-5-yl | F | NC(O)Et | 905 | 205.3, 205.0, 187.6, 177.2, 168.8, 164.9, 164.8, 158.4, 155.1, 149.2, 141.2, 139.2, 138.5, 110.1, 107.7, 103.8, 99.8, 98.2, 80.379.7, 76.6, 73.7, 73.5, 70.5, 69.5, 66.3, 63.1, 62.5, 41.3, 40.5, 38.9, 37.5, 31.3, 29.9, 29.0, 24.5, 24.3, 23.2, 21.3, 20.8, 17.3, 14.9, 14.5, 12.7, |
| 111 | 6-amino-pyridin-2-yl-thiazol-5-yl | F | NC(O)-isopropyl | 919 | 205.3, 205.1, 190.3, 176.9, 168.8, 164.9, 164.8, 158.4, 155.1, 149.1, 141.2, 139.2, 138.5, 110.1, 107.7, 103.9, 99.8, 98.2, 80.3, 79.7, 76.8, 76.6, 73.7, 70.5, 69.5, 66.3, 63.1, 62.6, 41.4, 40.5, 39.1, 37.5, 29.9, 28.9, 24.5, 24.3, 23.2, 21.4, 21.1, 20.7, 20.0, 18.7, 17.3, 14.9, 14.6, 12.7. |
| 112 | 4-amino-pyrimidin-2-yl-thiazol-5-yl | F | NC(O)-cyclopropyl | 917 | 205.3, 205.1, 188.1, 178.2, 168.8, 164.9, 164.8, 158.4, 155.1, 149.1, 141.2, 139.2, 138.5, 110.1, 107.7, 103.9, 99.8, 98.2, 95.2, 80.3, 79.7, 76.8, 73.7, 76.6, 73.4, 70.5, 69.6, 66.2, 63.1, 62.5, 41.4, 40.9, 40.5, 38.8, 37.6, 29.5, 29.0, 24.5, 24.3, 23.2, 21.3, 21.2, 20.8, 17.4, 16.6, 14.9, 14.5, 12.7, 10.0, 9.8. |
| 113 | 4-amino-pyrimidin-2-yl-pyridin-5-yl | F | NC(O)Et | 901 | 205.6, 205.4, 187.6, 177.1, 165.0, 164.8, 163.4, 162.8, 159.6, 156.3, 154.2, 149.4, 136.2, 132.7, 121.4, 103.9, 103.8, 99.7, 98.1, 80.3, 79.8, 76.8, 76.6, 73.7, 70.5, 69.6, 66.2, 63.2, 62.6, 54.0, 41.3, 40.5, 39.0, 37.5, 31.3, 29.5, 28.8, 24.7, 24.5, 23.3, 21.4, 20.9, 17.3, 15.0, 14.4, 12.7, 8.9 |
| 114 | 4-amino-pyrimidin-2-yl-pyridin-5-yl | F | NC(O)-isopropyl | 915 | 205.7, 205.4, 190.3, 176.9, 165.0, 164.8, 163.4, 162.8, 159.6, 156.3, 154.3, 149.4, 136.2, 132.7, 121.4, 104.0, 103.8, 99.7, 98.1, 80.3, 79.8, 76.8, 76.6, 73.7, 70.5, 69.7, 66.2, 63.2, 62.6, 41.3, 40.5, 39.1, 37.5, 29.5, 28.8, 24.6, 24.4, 23.3, 21.4, 21.2, 20.7, 20.2, 18.7, 17.3, 14.9, 14.5, 12.7 |

TABLE 6-continued

| Example | Ar | Y | A' | MS (M + H): m/e | Selected $^{13}$C (125 MHz, CDCl$_3$) δ |
|---|---|---|---|---|---|
| 115 | 3-amino-1-(4-chloro-phenyl)pyrazole | F | NC(O)Et | 922 | N/A |
| 116 | 3-amino-1-(4-chloro-phenyl)pyrazole | F | NC(O)-isopropyl | 936 | N/A |
| 117 | 6-amino-pyridin-2-yl thiazole | F | NC(O)Et | 905 | 205.3, 205.1, 187.5, 170.6, 158.2, 154.4, 149.9, 143.0, 138.7, 136.5, 110.0, 109.9, 103.9, 99.7, 98.1, 79.7, 76.5, 73.6, 70.5, 69.5, 68.5, 66.2, 63.1, 62.6, 60.6, 41.3, 40.5, 39.0, 31.2, 29.0, 24.5, 24.3, 23.2, 21.4, 21.3, 20.8, 17.3, 14.9, 14.4, 12.8, 8.9 |
| 118 | 6-amino-pyridin-2-yl oxazole | F | NC(O)-isopropyl | 903 | 189.9, 158.3, 153.9, 144.3, 139.0, 138.4, 137.3, 112.5, 110.1, 103.8, 103.6, 99.2, 79.4, 76.3, 73.4, 70.3, 69.5, 69.4, 68.3, 66.0, 62.8, 62.4, 53.8, 41.1, 40.2, 37.2, 36.6, 31.7, 29.2, 28.4, 24.7, 23.0, 21.1, 20.4, 19.7, 18.5, 17.1, 17.0, 14.7, 14.3, 12.4. |
| 119 | 4-aminothiazol-2-yl pyridine | H | NC(O)Et | 887 | 205.8, 188.0, 178.2, 167.7, 162.7, 159.7, 157.5, 154.2, 146.7, 133.6, 128.5, 121.8, 102.8, 91.1, 79.3, 79.2, 76.7, 76.5, 74.9, 70.4, 69.5, 66.2, 63.0, 50.7, 46.1, 40.5, 38.8, 31.3, 28.8, 23.8, 21.4, 20.3, 19.4, 17.7, 15.2, 14.3, 14.1, 13.5, 12.8, 8.8 |
| 120 | 4-aminothiazol-2-yl phenyl | F | NC(O)Et | 905 | 205.3, 205.1, 187.6, 177.2, 166.0, 165.0, 164.8, 157.1, 153.8, 139.7, 133.2, 128.4, 126.1, 104.0, 99.8, 98.1, 90.6, 80.2, 79.7, 76.6, 75.8, 73.7, 70.6, 69.7, 66.2, 63.2, 62.7, 41.3, 40.4, 39.0, 37.5, 31.3, 29.9, 28.8, 24.6, 24.4, 23.2, 21.4, 20.9, 17.4, 15.0, 14.5, 12.6, |
| 121 | 4-aminothiazol-2-yl phenyl | H | NC(O)Et | 887 | 205.8, 188.0, 178.4, 167.7, 166.0, 157.1, 153.7, 139.9, 133.2, 128.5, 126.1, 103.0, 90.6, 79.4, 79.1, 76.8, 75.6, 74.6, 70.5, 69.6, 66.1, 63.1, 62.9, 50.7, 46.2, 40.5, 38.9, 37.3, 31.3, 29.9, 28.7, 23.8, 21.4, 20.4, 19.4, 17.8, 15.2, 14.1, 13.7, 12.9, 8.9. |
| 122 | 2-aminothiazol-5-yl phenyl | F | NC(O)Et | 904.62 | 205.3, 205.1, 187.6, 177.1, 167.6, 165.0, 164.8, 153.6, 151.3, 137.4, 134.4, 128.3, 126.1, 103.9, 102.9, 99.8, 98.1, 80.2, 79.9, 79.7, 76.5, 76.0, 73.6, 70.5, 69.6, 66.1, 63.2, 62.7, 41.4, 40.5, 39.0, 37.5, 31.3, 29.9, 28.9, 24.6, 24.4, 23.1, 21.4, 20.9, 17.3, 15.0, 14.5, 12.6, 9.0. |
| 123 | 5-amino-1,2,4-thiadiazol-3-yl pyridine | F | NC(O)Et | 906 | N/A |
| 124 | 3-amino-1H-pyrazol-1-yl pyridine | F | NC(O)OMe | 890.5 | 205.4, 185.8, 163.5, 156.6, 154.6, 154.1, 138.8, 135.7, 128.0, 125.5, 122.4, 104.1, 97.3, 73.9, 70.6, 69.9, 66.1, 62.6, 53.2, 41.4, 40.5, 38.7, 28.5, 23.2, 21.4, 17.3, 14.9, 14.1, 12.6 |

TABLE 6-continued

| Example | Ar | Y | A' | MS (M + H): m/e | Selected $^{13}$C (125 MHz, CDCl$_3$) δ |
|---|---|---|---|---|---|
| 125 | 2-amino-thiazol-4-yl-pyridin-2-yl | F | NC(O)Et | 905 | 205.5, 205.2, 187.6, 168.3, 165.0, 164.8, 156.9, 154.1, 148.5, 147.2, 133.7, 129.6, 121.7, 104.1, 103.6, 99.7, 98.1, 79.7, 76.6, 76.5, 73.7, 70.6, 69.8, 66.1, 63.1, 62.6, 41.3, 40.4, 39.0, 31.2, 28.5, 24.6, 24.4, 23.2, 21.4, 20.9, 17.3, 14.9, 14.4, 12.6, 8.9 |
| 126 | 6-amino-pyridin-2-yl-oxazol-4-yl | F | NC(O)Me | 875 | 205.1, 204.9, 183.9, 164.8, 164.6, 160.7, 158.4, 153.8, 138.3, 137.3, 112.5, 110.1, 103.9, 99.5, 97.8, 79.4, 76.3, 73.5, 70.4, 69.6, 68.3, 65.8, 62.8, 62.3, 41.0, 40.2, 38.7, 29.6, 28.1, 25.0, 24.3, 24.1, 22.9, 21.2, 20.7, 17.1, 14.7, 14.0, 12.4. |
| 127 | 5-amino-1,2,4-thiadiazol-3-yl-phenyl | F | NC(O)Et | 905.6 | N/A. |
| 128 | 4-amino-thiazol-2-yl-pyridin-2-yl | F | NC(O)Et | 905.6 | N/A. |
| 129 | 5-amino-1,2,4-thiadiazol-3-yl-pyridin-2-yl | F | NC(O)Et | 906.6 | 205.5, 205.2, 187.6, 183.9, 169.2, 165.1, 165.0, 154.4, 150.4, 149.3, 136.5, 134.4, 122.7, 104.2, 99.7, 98.1, 80.3, 79.7, 76.8, 76.6, 73.7, 73.3, 70.7, 69.9, 66.1, 63.1, 62.6, 41.3, 40.5, 39.0, 31.3, 29.9, 28.4, 24.6, 24.4, 23.2, 21.5, 20.9, 17.4, 15.0, 14.4, 12.7, 8.9. |
| 130 | 5-amino-1,2,4-thiadiazol-3-yl-pyridin-2-yl | F | NC(O)-iso-propyl | 920.4 | N/A. |
| 131 | 4-amino-pyrimidin-2-yl-thiazol-5-yl | F | NC(O)Et | 906.61 | 205.4, 205.1, 187.5, 177.2, 172.7, 168.1, 165.0, 164.9, 163.3, 159.5, 156.5, 154.6, 143.5, 138.5, 104.9, 104.1, 99.7, 98.1, 79.7, 76.5, 73.6, 70.6, 69.8, 68.4, 66.0, 63.1, 62.6, 41.3, 40.4, 38.9, 31.7, 31.2, 30.3, 28.5, 24.5, 24.3, 23.2, 22.8, 21.4, 21.3, 20.8, 17.3, 14.9, 14.4, 12.8, 8.9. |
| 132 | 4-amino-thiazol-2-yl-pyrimidin-2-yl | F | NC(O)Et | 906.6 | 205.4, 205.2, 187.5, 167.5, 159.0, 158.1, 154.6, 154.2, 126.3, 104.1, 99.8, 98.1, 91.8, 79.7, 76.6, 76.3, 73.7, 70.6, 69.8, 66.1, 63.3, 62.6, 41.3, 40.4, 39.0, 37.6, 31.3, 29.9, 29.6, 28.5, 24.6, 24.4, 23.3, 21.4, 20.9, 17.4, 15.0, 14.4, 12.7, 8.9. |
| 133 | 4-amino-thiazol-2-yl-pyrazin-2-yl | F | NC(O)Et | 906 | 205.3, 205.1, 187.5, 165.0, 164.8, 163.7, 158.1, 154.9, 153.6, 145.6, 142.9, 140.1, 104.1, 99.8, 98.1, 94.5, 79.7, 76.6, 74.8, 73.8, 70.6, 69.8, 66.0, 63.0, 62.5, 41.4, 40.4, 38.9, 31.2, 29.9, 28.4, 24.5, 24.3, 23.2, 21.4, 21.3, 20.8, 17.4, 14.9, 14.4, 12.7, 8.9 |

TABLE 6-continued

| Example | Ar | Y | A' | MS (M+H): m/e | Selected $^{13}$C (125 MHz, CDCl$_3$) δ |
|---|---|---|---|---|---|
| 134 | 6-aminopyridin-2-yl-oxazol-2-yl (H$_2$N-pyridine-oxazole) | F | NC(O)Et | 889 | N/A. |
| 135 | 4-aminothiazol-2-yl-pyridin-5-yl (H$_2$N-thiazole-pyridine) | F | NC(O)Et-d$_5$ | 910.5 | 205.4, 205.2, 187.7, 177.1, 165.0, 164.8, 162.5, 159.4, 157.7, 154.5, 146.7, 133.7, 128.6, 121.6, 104.1, 99.8, 98.1, 91.0, 80.4, 79.7, 76.5, 73.8, 70.6, 69.8, 66.0, 63.2, 62.5, 41.3, 40.4, 39.0, 37.5, 28.4, 24.6, 24.4, 23.2, 21.4, 20.9, 17.4, 14.9, 14.4, 12.6. |
| 136 | 6-aminopyridin-2-yl-thiazol-2-yl | F | NC(O)Me | 891 | 205.1, 204.9, 183.9, 169.3, 158.0, 154.3, 153.6, 149.5, 138.5, 118.3, 110.1, 109.6, 103.8, 99.5, 97.8, 79.4, 76.3, 73.4, 72.0, 69.5, 65.8, 62.9, 62.3, 41.0, 40.2, 28.1, 25.0, 24.3, 24.2, 23.0, 21.1, 20.7, 17.1, 14.7, 14.1, 12.4. |
| 137 | 6-aminopyridin-2-yl-thiazol-2-yl | F | NC(O)-isopropyl | 919 | 205.1, 204.9, 189.9, 169.3, 157.9, 154.4, 153.7, 149.6, 138.5, 118.2, 110.1, 109.6, 103.9, 99.5, 97.9, 80.0, 79.4, 76.3, 73.4, 72.0, 70.4, 69.6, 65.8, 62.9, 62.4, 41.1, 40.2, 38.9, 37.2, 28.1, 24.3, 24.1, 23.0, 21.2, 20.9, 20.4, 19.7, 18.5, 17.0, 14.7, 14.3, 12.4. |
| 138 | 6-aminopyrazin-2-yl-thiazol-2-yl | F | NC(O)Et | 850 | N/A. |
| 139 | lysyl-amide linked to 6-(thiazol-2-yl)pyridin-2-yl | F | NC(O)Et | 1033.56 | 205.3, 205.1, 187.5, 177.1, 174.3, 168.5, 164.9, 164.8, 154.8, 154.0, 150.9, 149.8, 139.4, 118.9, 115.8, 114.6, 104.1, 99.7, 98.1, 79.7, 76.5, 73.6, 72.2, 70.6, 69.8, 66.0, 63.1, 62.6, 55.9, 41.9, 41.3, 40.4, 38.9, 34.9, 31.2, 28.3, 27.2, 24.5, 24.4, 23.4, 23.2, 21.4, 20.9, 17.3, 14.9, 14.4, 12.7, 8.9. |
| 140 | lysyl-amide linked to 6-(oxazol-2-yl)pyridin-2-yl | F | NC(O)Et | 1016.96 | 205.4, 205.1, 187.5, 174.8, 160.3, 154.2, 151.7, 144.4, 139.4, 137.9, 118.2, 115.3, 104.1, 99.7, 98.1, 79.6, 76.5, 73.6, 69.8, 68.3, 66.0, 63.0, 62.5, 56.0, 42.0, 41.3, 40.4, 38.9, 35.0, 31.2, 28.3, 27.2, 24.6, 24.4, 23.3, 23.2, 21.4, 20.8, 17.3, 14.9, 14.4, 12.7, 8.9. |

Prodrug Studies

In vitro and in vivo studies were conducted on compounds 5, 6, 7 and 8, each of which is an amino acid prodrug of either compound 1 or compound 3, to see the effectiveness of these amino acid derivatives to cleave at the amide bond to liberate the free amino thiazole and amino pyridine of compounds 1 and 3.

The amino acid derivatives were rapidly cleaved to the active free amino compounds in human, rat and mouse blood plasma and human intestinal tissue. The amino acid derivatives were cleaved in human blood very efficiently with a shorter half life than in either rat or mouse blood. An in vivo pharmacokinetic study in rats also confirmed the rapid cleavage of the amino acid to provide the corresponding amino thiazole, compound 1. In addition, incubation with leucine aminopeptidase completely cleaved the amino acid within one minutes (data not shown).

Experimental procedures and results are summarized in the Tables 7-11 below.

In Vitro Experimental Procedures

Human Intestine S9 Incubations

Compound 5 (1 μM) was incubated with human intestine S9 and human liver S9 (2 mg protein/mL) in potassium phosphate buffer (100 mM, pH 7.2) containing MgCl$_2$ (5 mM) in the presence of NADPH (2 mM) at 37±1° C. Reaction was started by the addition of compound 5, and was stopped at predefined time points (0, 5, 10, 15, 20, 25, 30, 45 and 60 minutes) by removing one aliquot from the incubation mixture (0.1 mL per aliquot) and adding it to 3-fold volume of stop reagent (ice-cold acetonitrile, 0.3 mL). Precipitated protein was removed by centrifugation. Prodrug compound 5 and parent compound 1 concentrations in the supernatant were analyzed by LC/MS/MS.

Human, Rat and Mouse Blood Incubations

Compounds 5, 6, 7 and 8 (2 μM) were incubated with fresh human blood (conducted in duplicate), rat and mouse blood. Reaction was started by the addition of compound 5, and was stopped at predefined time points (0, 5, 10, 15, 30, 45 and 60 minutes) by removing one aliquot from the incubation mixture (0.1 mL per aliquot) and adding it to 3-fold volume of stop reagent (ice-cold acetonitrile, 0.3 mL). Precipitated protein was removed by centrifugation. Prodrug compound 5-8 and parent compound 1 or 3 concentrations in the supernatant were analyzed by LC/MS/MS.

TABLE 7

Cleavage of amino acid prodrugs in blood incubations

| Compounds | Formula IIIa Ar | In vitro Blood incubations % remaining after 60 min | | |
|---|---|---|---|---|
| | | Mice | Rat | Human |
| 5 | Ala-NH-thiazole-pyridine | 9.0% | 23.7% | 12.9% |
| 6 | Leu-NH-thiazole-pyridine | 5.6% | 9.3% | 8.3% |
| 7 | Ala-NH-pyridine-thiazole | 27.5% | 38.7% | 23.5% |
| 8 | Leu-NH-pyridine-thiazole | 8.6% | 8.7% | 12.0% |

After oral (po) and IV adminstration of compound 5 or 6 to rat, it was rapidly converted to the parent amino derivative (Compound 1).

TABLE 8

Rat PK parameters of amino acid prodrug after IV/PO administrations of Compound 5 or Compound 6

| Dose mg/kg | Dose Route | Compound | $C_{max}$ (µg/mL) | $T_{max}$ (hr) | $V_d$ (L/kg) | $Cl_F$ (L/hr · kg) | $t_{1/2}$ (hr) | $AUC_{0-\infty}$ (µg · hr/mL) | F (%) |
|---|---|---|---|---|---|---|---|---|---|
| 10 | IV | 5 | 1.16 | 0.08 | 4.94 | 23.8 | 0.14 | 0.42 | |
| | | Conversion to 1 | 4.85 | 0.08 | 2.09 | 0.45 | 3.19 | 22.03 | |
| 10 | PO | 5 | None detected in plasma via oral route-All cleaved to parent | | | | | | |
| | | Conversion to 1 | 1.32 | 6.0 | | | 2.98 | 8.84 | 40.1 |
| 10 | IV | 6 | 0.31 | 0.08 | 13.3 | 47.3 | 0.2 | 0.21 | |
| | | Conversion to 1 | 5.97 | 0.08 | 2.35 | 0.41 | 3.98 | 24.4 | |
| 10 | PO | 6 | None detected in plasma via oral route-All cleaved to parent | | | | | | |
| | | Conversion to 1 | 1.35 | 3.0 | | | 3.34 | 8.21 | 33.6 |

No prodrug was detected in the plasma when compound 5 or 6 given orally. All were converted to the parent compound 1.

Biological Activity

Representative compounds of the invention showed improved MICs (minimum inhibition concentration) and/or pharmacodynamic properties over compounds disclosed in U.S. Pat. No. 6,878,691.

In particular, the compounds of the invention have improved activities against methecillin resistant *Staphylococcus aureus* (MRSA) and/or *Haemophilus influenzae* isolates. Traditional macrolide antibiotics are not active against resistant MRSA. However the unique features of the biaryl side chains of the invention provided improved activities against this highly resistant MRSA including constitutively resistant isolates while some unique side chains improve activity against *H. influenzae* isolates which is also a weakness of macrolide antibiotics.

In addition compound like example 4 provided improved in vivo pharmacological data such as animal infection models and pharmacokinetic properties particularly the high AUC (area under the curve) in dogs.

Tables 9 and 10 below show microbiological data of the present inventions (compounds of Formula XVI) and Table 11 shows microbiological data for related compounds of U.S. Pat. No. 6,878,691 for reference.

For simplicity only selected data against either MRSA or *H. influenzae* isolates are highlighted here.

TABLE 9

MIC (µg/mL) Data of Compounds of Formula XVI

| Compound | Ar | Y | A' | H. influenzae 33929 | H. influenzae 49247 |
|---|---|---|---|---|---|
| 2 | 3-amino-1,2,4-thiadiazol-5-yl pyridine | H | O | 2 | 1 |
| 4 | isoxazol-5-yl pyridine | H | NC(O)Me | 4 | 4 |
| 12 | 6-amino-pyridin-2-yl thiadiazole | F | NC(O)Me | 4.00 | 2.00 |
| 13 | 6-amino-pyridin-2-yl imidazole | H | NC(O)Me | 4.00 | 2.00 |

TABLE 9-continued
MIC (μg/mL) Data of Compounds of Formula XVI
| | | | | H. influenzae | |
|---|---|---|---|---|---|
| Compound | Ar | Y | A' | 33929 | 49247 |
| 14 | 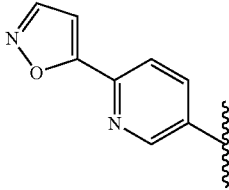 [SMILES: *c1ccc(-c2ccno2)nc1] | H | O | 4.00 | 2.00 |
| 15 | 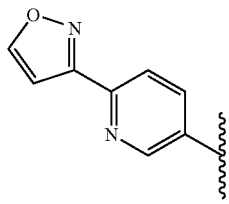 [SMILES: *c1ccc(-c2ccon2)nc1] | H | O | 4.00 | 2.00 |
| 16 | 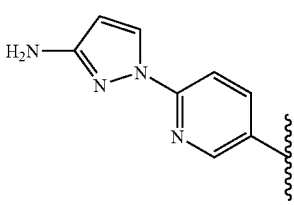 [SMILES: *c1ccc(-n2ccc(N)n2)nc1] | H | O | 2.00 | 2.00 |
| 17 | 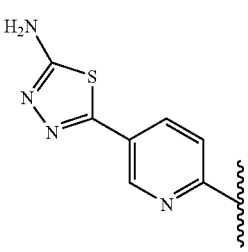 [SMILES: *c1ccc(-c2nnc(N)s2)cn1] | H | O | 2.00 | 1.00 |
| 18 | 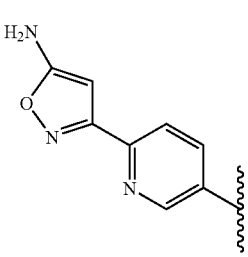 [SMILES: *c1ccc(-c2cc(N)on2)nc1] | H | NC(O)Me | 4.00 | 2.00 |
| 19 | 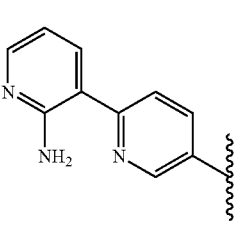 [SMILES: *c1ccc(-c2cccnc2N)nc1] | H | NC(O)Me | 4.00 | 2.00 |

TABLE 9-continued

MIC (μg/mL) Data of Compounds of Formula XVI

| | | | | H. influenzae | |
|---|---|---|---|---|---|
| Compound | Ar | Y | A' | 33929 | 49247 |
| 20 | 5-amino-isoxazol-3-yl-pyridin-5-yl | H | O | 4.00 | 2.00 |
| 21 | 2-amino-pyridin-3-yl-pyridin-5-yl | H | O | 2.00 | 4.00 |
| 22 | 6-amino-pyridin-2-yl-thiophen-5-yl | H | NC(O)Me | 2.00 | 2.00 |
| 23 | 6-amino-pyridin-2-yl-pyridin-5-yl | F | NH | 4.00 | 2.00 |
| 24 | 3-amino-pyrazol-1-yl-(3-fluoro)phenyl | F | O | 4.00 | 4.00 |
| 25 | 5-amino-pyrazol-1-yl-phenyl | F | NC(O)Me | 4.00 | 4.00 |
| 26 | 3-amino-pyrazol-1-yl-phenyl | F | O | 4.00 | 4.00 |

TABLE 9-continued
MIC (μg/mL) Data of Compounds of Formula XVI
| Compound | Ar | Y | A' | H. influenzae 33929 | 49247 |
|---|---|---|---|---|---|
| 27 | 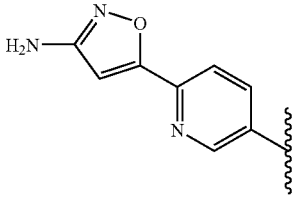 [SMILES: *c1ccc(-c2cc(N)no2)nc1] | F | O | 2.00 | 2.00 |
| 28 | 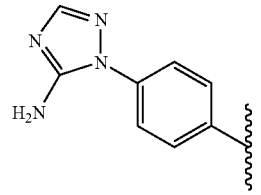 [SMILES: *c1ccc(-n2ncnc2N)cc1] | F | NC(O)Me | 2.00 | 2.00 |
| 29 | 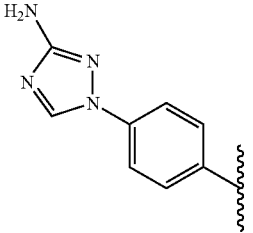 [SMILES: *c1ccc(-n2cnc(N)n2)cc1] | F | NC(O)Me | 4.00 | 2.00 |
| 30 | 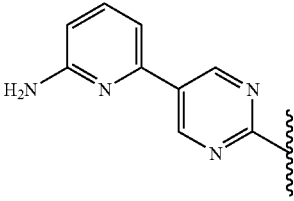 [SMILES: *c1ncc(-c2cccc(N)n2)cn1] | F | NC(O)Me | 4.00 | 2.00 |
| 31 | 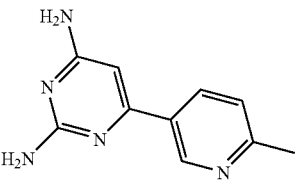 | F | NC(O)Me | 4 | 2 |
| 32 | 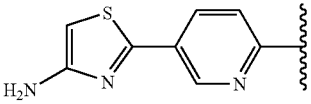 | H | O | 2 | 2 |
| 33 | 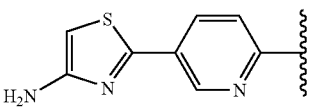 | F | O | 4 | 2 |
| 34 | 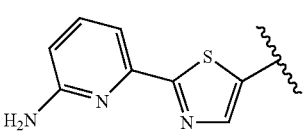 | H | O | 2 | 2 |

TABLE 9-continued

MIC (μg/mL) Data of Compounds of Formula XVI

| Compound | Ar | Y | A' | H. influenzae 33929 | H. influenzae 49247 |
|---|---|---|---|---|---|
| 35 | 5-amino-1,2,4-thiadiazol-3-yl-pyridin-2-yl | H | O | 2 | 2 |
| 36 | 6-aminopyridin-2-yl-thiazol-2-yl | H | O | 2 | 2 |
| 37 | 6-aminopyridin-2-yl-thiazol-5-yl | H | NC(O)Me | 4 | 2 |
| 38 | 3-amino-1,2,4-oxadiazol-5-yl-phenyl | F | O | 2 | 4 |
| 39 | 6-aminopyridin-2-yl-oxazol-4-yl | H | O | 1 | 1 |
| 40 | 6-aminopyridin-2-yl-oxazol-4-yl | H | NC(O)Me | 2 | 2 |
| 41 | 2-aminothiazol-4-yl-pyridin-2-yl | H | O | 2 | 1 |
| 42 | 3-amino-1,2,4-oxadiazol-5-yl-phenyl | H | O | 2 | 1 |

TABLE 9-continued

MIC (μg/mL) Data of Compounds of Formula XVI

| Compound | Ar | Y | A' | H. influenzae 33929 | H. influenzae 49247 |
|---|---|---|---|---|---|
| 43 | 3-amino-1,2,4-oxadiazol-5-yl pyridine | F | O | 2 | 2 |
| 44 | 3-amino-1,2,4-thiadiazol-5-yl phenyl | H | O | 2 | 1 |
| 45 | 3-amino-1,2,4-oxadiazol-5-yl pyridine | H | O | 2 | 1 |
| 46 | 5-amino-tetrazol-1-yl phenyl | H | O | 2 | 2 |
| 47 | 5-amino-tetrazol-1-yl phenyl | H | NC(O)Me | 2 | — |
| 48 | 3-amino-1,2,4-thiadiazol-5-yl phenyl | H | NC(O)Me | 2 | — |
| 49 | 3-amino-pyrazol-1-yl pyridine | F | O | 2 | 2 |

TABLE 9-continued

MIC (μg/mL) Data of Compounds of Formula XVI

| Compound | Ar | Y | A' | H. influenzae 33929 | H. influenzae 49247 |
|---|---|---|---|---|---|
| 50 | 6-amino-pyridin-2-yl-pyrimidin-2-yl | H | O | 2 | 2 |
| 51 | 3-amino-1,2,4-oxadiazol-5-yl-pyridin-2-yl | H | O | 2 | 2 |
| 52 | 6-amino-pyridin-2-yl-1,2,4-oxadiazol-5-yl | F | O | 1 | 2 |
| 53 | 6-amino-pyridin-2-yl-1,2,4-oxadiazol-5-yl | H | O | 1 | 1 |
| 54 | 6-amino-pyridin-2-yl-1,2,4-oxadiazol-3-yl | H | O | 1 | 1 |
| 55 | 2-amino-oxazol-4-yl-pyridin-5-yl | H | O | 2 | 1 |
| 56 | 3-amino-1,2,4-thiadiazol-5-yl-phenyl | F | O | 2 | 2 |

TABLE 9-continued

MIC (μg/mL) Data of Compounds of Formula XVI

| | | | | H. influenzae | |
|---|---|---|---|---|---|
| Compound | Ar | Y | A' | 33929 | 49247 |
| 57 | H₂N-pyrimidine-pyrazole | F | NC(O)Et | 4 | 2 |
| 58 | H₂N-pyridine-pyrazole | H | O | 2 | 2 |
| 59 | H₂N-pyridine-pyrazole | F | NC(O)Me | 2 | 2 |
| 60 | H₂N-oxazole-pyridine | H | O | 2 | 2 |
| 61 | H₂N-thiadiazole-pyridine | H | O | 2 | 2 |
| 62 | H₂N-oxadiazole-pyridazine | H | O | 2 | 2 |
| 63 | H₂N-pyridine-thiazole | H | O | 2 | 1 |

TABLE 9-continued
MIC (µg/mL) Data of Compounds of Formula XVI
| Compound | Ar | Y | A' | H. influenzae 33929 | H. influenzae 49247 |
|---|---|---|---|---|---|
| 64 | 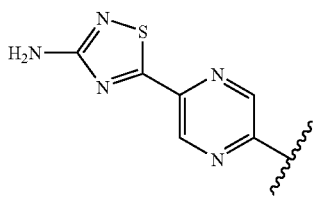 [SMILES: *c1cnc(-c2nc(N)ns2)cn1] | F | O | 2 | 1 |
| 65 | 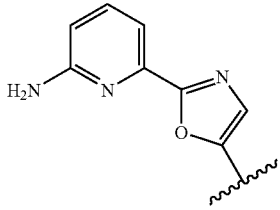 | F | NC(O)Et | 4 | 1 |
| 66 | 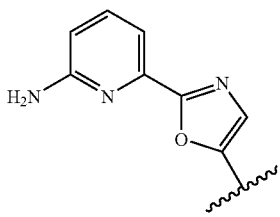 | H | O | 2 | 0.5 |
| 67 | 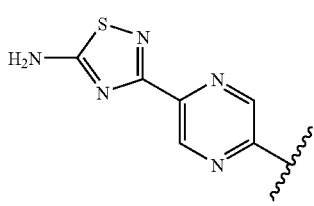 [SMILES: *c1cnc(-c2nsc(N)n2)cn1] | F | NC(O)Et | 4 | 2 |
| 68 | 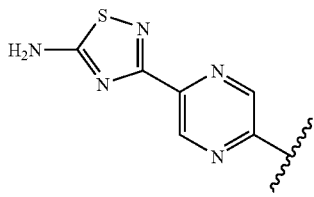 [SMILES: *c1cnc(-c2nsc(N)n2)cn1] | H | O | 2 | 2 |
| 69 | 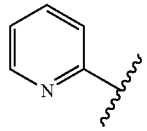 [SMILES: *c1ccccn1] | F | NC(O)Et | 2 | 2 |
| 70 | 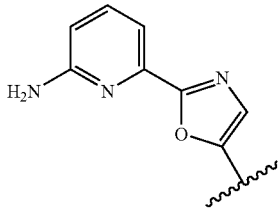 | H | NC(O)Me | 2 | 2 |

TABLE 9-continued

MIC (μg/mL) Data of Compounds of Formula XVI

| | | | | H. influenzae | |
|---|---|---|---|---|---|
| Compound | Ar | Y | A' | 33929 | 49247 |
| 71 | ![pyridine-thiazole with H2N] | H | O | 2 | N/A |
| 72 | ![pyridine-thiazole with H2N] | F | O | 1 | 0.5 |
| 73 | ![pyrazine-thiazole with H2N] | H | O | 2 | N/A |

TABLE 10

MIC (μg/mL) Data of Compounds of Formula XVI

| | | | | MRSA | |
|---|---|---|---|---|---|
| Compound | Ar | Y | A' | 33591 | 7662 |
| 1 | ![thiazole-pyridine with H2N] | F | NC(O)Et | 2 | 1 |
| 3 | ![pyridine-thiazole with H2N] | F | NC(O)Et | 2 | 1 |
| 11 | ![pyridine-oxazole with H2N] | F | NC(O)Et | 4 | 2 |
| 74 | ![bipyridine with H2N] | F | NC(O)Me | 8 | 8 |

TABLE 10-continued

MIC (μg/mL) Data of Compounds of Formula XVI

| Compound | Ar | Y | A' | MRSA 33591 | 7662 |
|---|---|---|---|---|---|
| 75 | 6-(6-aminopyridin-3-yl)pyridin-2-yl | F | NC(O)Et | 4 | 4 |
| 76 | 6-(6-aminopyridin-3-yl)pyridin-2-yl | F | NC(O)-propyl | 4 | 4 |
| 77 | 6-(6-aminopyridin-3-yl)pyridin-2-yl | F | NC(O)-cyclopro-pyl | 8 | 8 |
| 78 | 6-(3-amino-1H-pyrazol-1-yl)pyridin-3-yl | F | NC(O)Me | 8 | 8 |
| 79 | 6-(3-amino-1H-pyrazol-1-yl)pyridin-3-yl | F | NC(O)Et | 4 | 2 |
| 80 | 6-(6-aminopyridin-3-yl)pyridin-2-yl | F | NC(O)-isopropyl | 4 | 4 |
| 81 | 4-(3-amino-1H-pyrazol-1-yl)phenyl | F | NC(O)Me | 4 | 4 |

TABLE 10-continued

MIC (μg/mL) Data of Compounds of Formula XVI

| Compound | Ar | Y | A' | MRSA 33591 | MRSA 7662 |
|---|---|---|---|---|---|
| 82 | H₂N-pyrazole-N-pyridine | F | NC(O)Me | 8 | 4 |
| 83 | H₂N-pyrazole-N-phenyl | H | NC(O)Et | 4 | 2 |
| 84 | H₂N-pyrazole-N-phenyl(F) | H | NC(O)Me | 8 | 8 |
| 85 | H₂N-pyrazole-N-phenyl(F) | F | NC(O)Me | 8 | 4 |
| 86 | H₂N-pyrazole-N-pyridine | F | NC(O)-isopropyl | 4 | 4 |
| 87 | H₂N-pyrazole-N-pyridine | F | NC(O)-isopropyl | 4 | 2 |
| 88 | H₂N-pyrazole-N-phenyl(Cl) | H | NC(O)Me | 8 | 8 |

TABLE 10-continued

MIC (μg/mL) Data of Compounds of Formula XVI

| Compound | Ar | Y | A' | MRSA 33591 | MRSA 7662 |
|---|---|---|---|---|---|
| 89 | 3-amino-pyrazol-1-yl, 3-chloro-phenyl | F | NC(O)Me | 4 | 4 |
| 90 | 3-amino-pyrazol-1-yl, phenyl | H | NC(O)-isopropyl | 8 | 8 |
| 91 | 3-amino-pyrazol-1-yl, phenyl | F | NC(O)-isopropyl | 4 | 4 |
| 92 | 3-amino-pyrazol-1-yl, pyridyl | F | NC(O)Et | 4 | 2 |
| 93 | 3-amino-pyrazol-1-yl, phenyl | F | NC(O)-cyclopropyl | 8 | 8 |
| 94 | 3-amino-pyrazol-1-yl, pyridyl | F | NC(O)-cyclopropyl | 8 | 8 |
| 95 | 3-amino-pyrazol-1-yl, 2-fluoro-phenyl | F | NC(O)Me | 8 | 8 |

TABLE 10-continued
MIC (μg/mL) Data of Compounds of Formula XVI
| Compound | Ar | Y | A' | MRSA 33591 | MRSA 7662 |
|---|---|---|---|---|---|
| 96 | 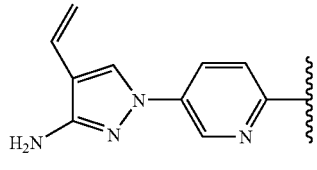 [SMILES: *c1ccc(-n2cc(C=C)c(N)n2)cn1] | F | NC(O)Me | 8 | 8 |
| 97 | 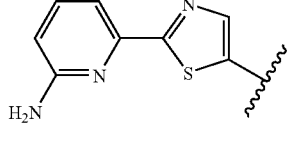 | F | NC(O)Me | 8 | 8 |
| 98 | 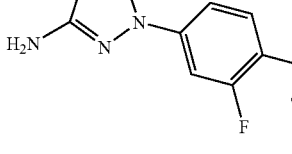 | H | NC(O)-isopropyl | 8 | 8 |
| 99 | 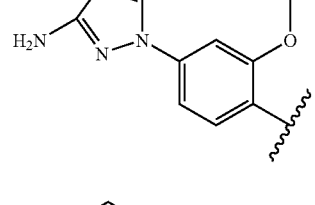 | F | NC(O)Me | 8 | 8 |
| 100 | 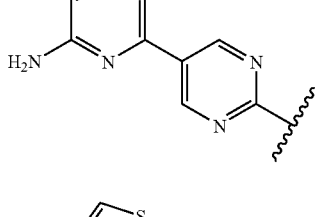 | F | NC(O)-isopropyl | 8 | 8 |
| 101 | 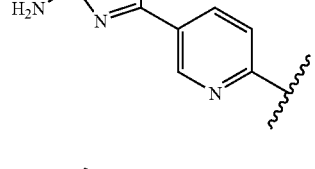 | F | NC(O)Me | 4 | 2 |
| 102 | 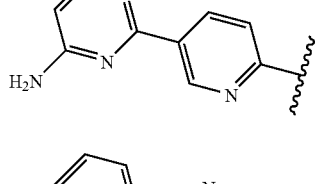 | F | NC(O)Me | 8 | 8 |
| 103 | 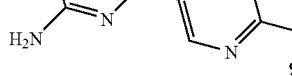 | F | NC(O)Me | 8 | 8 |

TABLE 10-continued
MIC (µg/mL) Data of Compounds of Formula XVI
| Compound | Ar | Y | A' | MRSA 33591 | MRSA 7662 |
|---|---|---|---|---|---|
| 104 | 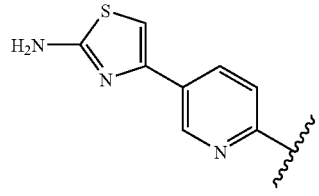 | F | NC(O)Me | 8 | 8 |
| 105 | 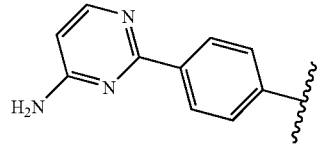 [SMILES: *c1ccc(-c2nccc(N)n2)cc1] | F | NC(O)Me | 8 | 8 |
| 106 | 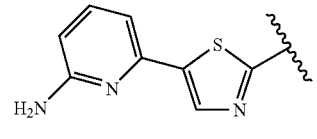 | F | NC(O)Me | 8 | 4 |
| 107 | 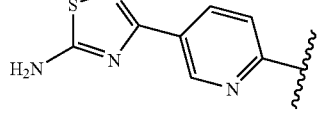 | F | NC(O)Me | 16 | 8 |
| 108 | 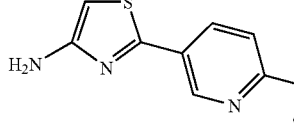 | H | NC(O)Me | 8 | 8 |
| 109 | 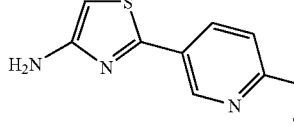 | F | NC(O)-isopropyl | 2 | 2 |
| 110 | 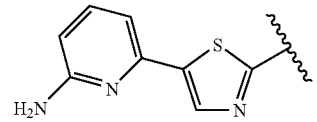 | F | NC(O)Et | 2 | 2 |
| 111 | 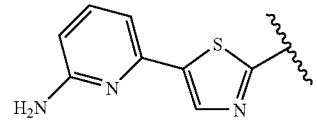 | F | NC(O)-isopropyl | 2 | 2 |
| 112 | 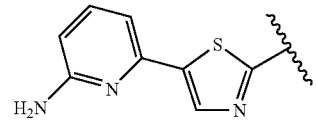 | F | NC(O)-cyclopropyl | 8 | 4 |

TABLE 10-continued

MIC (μg/mL) Data of Compounds of Formula XVI

| Compound | Ar | Y | A' | MRSA 33591 | MRSA 7662 |
|---|---|---|---|---|---|
| 113 | 4-amino-pyrimidin-2-yl-pyridin-2-yl | F | NC(O)Et | 8 | 4 |
| 114 | 4-amino-pyrimidin-2-yl-pyridin-2-yl | F | NC(O)-isopropyl | 8 | 4 |
| 115 | 3-amino-pyrazol-1-yl-(3-chloro)phenyl | F | NC(O)Et | 4 | 4 |
| 116 | 3-amino-pyrazol-1-yl-(3-chloro)phenyl | F | NC(O)-isopropyl | 4 | 4 |
| 117 | 6-amino-pyridin-2-yl-thiazol-2-yl | F | NC(O)Et | 4 | 2 |
| 118 | 6-amino-pyridin-2-yl-oxazol-2-yl | F | NC(O)-isopropyl | 8 | 4 |
| 119 | 4-amino-thiazol-2-yl-pyridin-2-yl | H | NC(O)Et | 8 | 4 |
| 120 | 4-amino-thiazol-2-yl-phenyl | F | NC(O)Et | 4 | 4 |
| 121 | 4-amino-thiazol-2-yl-phenyl | H | NC(O)Et | 8 | 8 |
| 122 | 2-amino-thiazol-4-yl-phenyl | F | NC(O)Et | 4.00 | 4.00 |

TABLE 10-continued

MIC (μg/mL) Data of Compounds of Formula XVI

| | | | | MRSA | |
|---|---|---|---|---|---|
| Compound | Ar | Y | A' | 33591 | 7662 |
| 123 | [5-amino-1,2,4-thiadiazol-3-yl-pyridin-2-yl] | F | NC(O)Et | 4 | 4 |
| 124 | [3-amino-pyrazol-1-yl-pyridin-2-yl] | F | NC(O)OMe | 8.00 | 4.00 |
| 125 | [2-amino-thiazol-4-yl-pyridin-2-yl] | F | NC(O)Et | 8 | 4 |
| 126 | [6-amino-pyridin-2-yl-oxazol-4-yl] | F | NC(O)Me | 8 | 4 |
| 127 | [5-amino-1,2,4-thiadiazol-3-yl-phenyl] | F | NC(O)Et | 4.00 | 2.00 |
| 128 | [4-amino-thiazol-2-yl-pyridin-2-yl] | F | NC(O)Et | 8.00 | 4.00 |
| 129 | [5-amino-1,2,4-thiadiazol-3-yl-pyridin-2-yl] | F | NC(O)Et | 8.00 | 4.00 |
| 130 | [5-amino-1,2,4-thiadiazol-3-yl-pyridin-2-yl] | F | NC(O)-isopropyl | 4.00 | 2.00 |
| 131 | [4-amino-pyrimidin-2-yl-thiazol-5-yl] | F | NC(O)Et | 8.00 | 4.00 |

TABLE 10-continued

MIC (μg/mL) Data of Compounds of Formula XVI

| Compound | Ar | Y | A' | MRSA 33591 | MRSA 7662 |
|---|---|---|---|---|---|
| 132 | 4-amino-thiazole-pyrimidine | F | NC(O)Et | 4.00 | 2.00 |
| 133 | 4-amino-thiazole-pyrazine | F | NC(O)Et | 4.00 | 2.00 |
| 134 | 6-amino-pyridine-oxazole | F | NC(O)Et | 8.00 | 4.00 |
| 135 | 4-amino-thiazole-pyridine | F | NC(O)Et-d$_5$ | 2.00 | 2.00 |
| 136 | 6-amino-pyridine-thiazole | F | NC(O)Me | 2.00 | 2.00 |
| 137 | 6-amino-pyridine-thiazole | F | NC(O)-isopropyl | 2.00 | 1.00 |
| 138 | 6-amino-pyrazine-thiazole | F | NC(O)Et | 4.00 | 4.00 |

Table 11 shows microbiological data for related compounds of U.S. Pat. No. 6,878,691 for reference.
TABLE 11
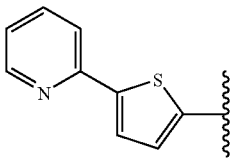 [SMILES: *c1ccc(-c2ccccn2)s1]
MIC (μg/mL) Data
| Example No. in U.S. Pat. No. 6,878,691 | Ar | Y | A' | MRSA 33591 | H. influenzae 33929 | H. influenzae 49247 |
|---|---|---|---|---|---|---|
| 115 | 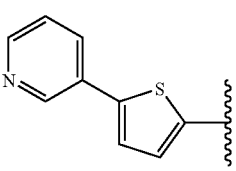 [SMILES: *c1ccc(-c2cccnc2)s1] | H | NC(O)Me | >64 | 16 | 16 |
| 66 | 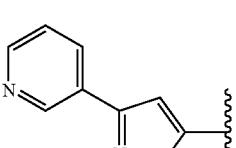 | H | NC(O)Me | >64 | 16 | 16 |
| 69 | 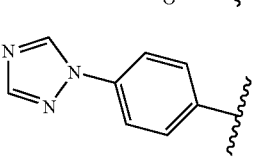 | H | NC(O)Me | >64 | 16 | 16 |
| 91 | 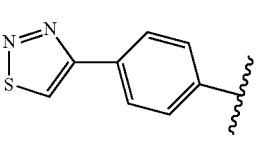 [SMILES: *c1ccc(-c2csnn2)cc1] | H | NC(O)Me | >64 | 16 | 8 |
| 72 | 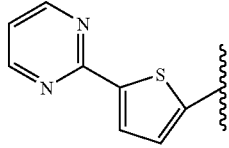 [SMILES: *c1ccc(-c2ncccn2)s1] | H | NC(O)Me | >64 | 8 | 8 |
| 140 | 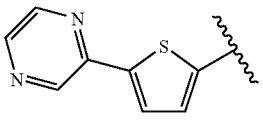 | F | NC(O)Me | 16 | 8 | 8 |
| 141 | | F | NC(O)Me | 32 | 8 | 8 |

177                                                                                                    178
TABLE 11-continued
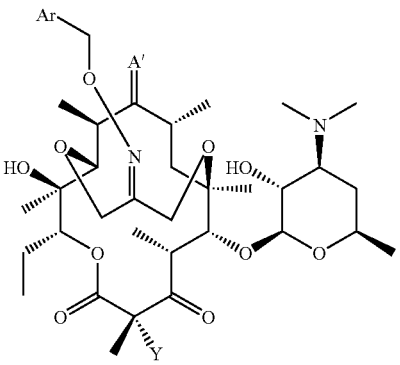
MIC (μg/mL) Data
| Example No. in U.S. Pat. No. 6,878,691 | Ar | Y | A' | MRSA 33591 | H. influenzae 33929 | 49247 |
|---|---|---|---|---|---|---|
| 173 | 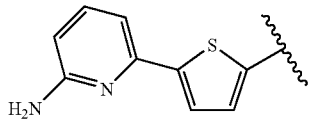 | F | NC(O)Me | 4 | 4 | 4 |
| 205 | 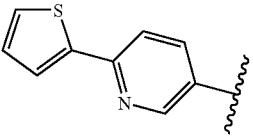 [SMILES: *c1ccc(-c2cccs2)nc1] | H | NC(O)Me | >64 | 4 | 8 |
| 193 | 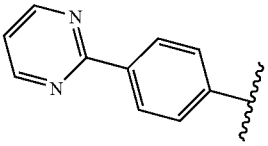 [SMILES: *c1ccc(-c2ncccn2)cc1] | H | NC(O)Me | 64 | 8 | 8 |
| 195 | 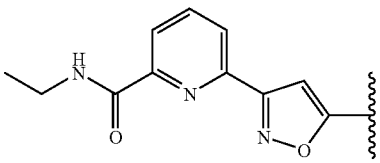 [SMILES: *c1cc(-c2cccc(C(=O)NCC)n2)no1] | H | NC(O)Me | >64 | 32 | 32 |
| 212 | 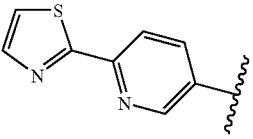 [SMILES: *c1ccc(-c2nccs2)nc1] | H | NC(O)Me | 64 | 4 | 8 |
| 214 | 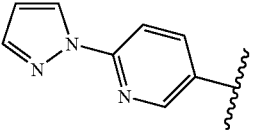 [SMILES: *c1ccc(-n2cccn2)nc1] | F | NC(O)Me | 64 | 4 | 8 |
| 219 | 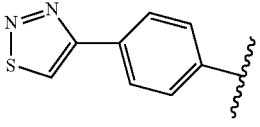 | F | NC(O)Me | 32 | 4 | 4 |

TABLE 11-continued
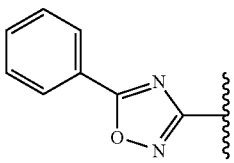 [SMILES: *c1noc(-c2ccccc2)n1]
MIC (μg/mL) Data
| Example No. in U.S. Pat. No. 6,878,691 | Ar | Y | A' | MRSA 33591 | H. influenzae 33929 | H. influenzae 49247 |
|---|---|---|---|---|---|---|
| 106 | 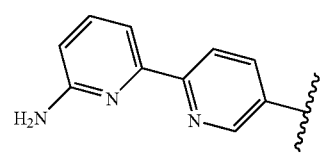 [SMILES: *c1ccc(-c2cccc(N)n2)nc1] | H | NC(O)Me | >64 | 8 | 8 |
| 227 | 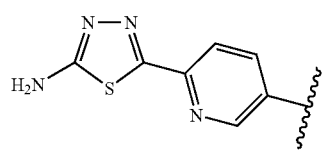 [SMILES: *c1ccc(-c2nnc(N)s2)nc1] | H | NC(O)Me | 32 | 4 | 4 |
| 234 | 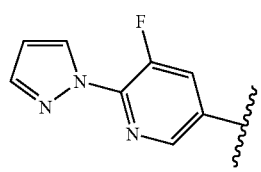 [SMILES: *c1cnc(-n2cccn2)c(F)c1] | H | NC(O)Me | >64 | 4 | 4 |
| 259 |  | H | NC(O)Me | >64 | 8 | 8 |
MRSA 7662 data are not available for compounds uf U.S. Pat. No. 6,878,691.

Compound 1 (example 1) not only has extremely potent MIC against MRSA but also very effective in various animal models of infections and highly accumulated at the site of infections in infected skin tissue of mice.

| In vivo Efficacies in Systemic Mouse Protection Model of Compound 1 | | | | |
|---|---|---|---|---|
| Compound | Organism | Route | MIC (µg/mL) | $ED_{50}$ (mg/kg) |
| 1 | S. aureus Smith | po | 0.13 | 13.3 |
| 1 | S. aureus Smith | iv | 0.13 | 4.8 |
| 1 | S. aureus 7662 | iv | 1 | 3.6 |

| In vivo Efficacies in Mouse Skin and Soft Tissue Infection of Compound 1 | | | | |
|---|---|---|---|---|
| Compound | Organism | Route | MIC (µg/mL) | ED50 (mg/kg) |
| 1 | MRSA 7662 | po | 1 | 29 |
| 1 | MRSA 7662 | iv | 1 | 12 |

| High Tissue Accumulation of Compound 1 at the Site of Infection | | | | |
|---|---|---|---|---|
| 50 mg/kg | po | Plasma | Uninfected Skin | Infected Skin Abscess |
| Cmax | mg/ml | 5.12 | 3.80 | 9.03 |
| Tmax | hr | 0.5 | 3.0 | 3.0 |
| AUC 0-24 h | mg-h/ml | 24.4 | 54.6 | 257 |
| AUC 0-∞ | mg-h/ml | 24.5 | 66.6 | 617 |
| T½ | hr | 5.2 | 17.9 | 52.4 |
| Tissue/Plasma | AUC 0-∞ ratio | | 2.72 | 25.2 |

Compound 4 (example 4), not only showed potent antibacterial activities against S. aureus, S. pneumonia and ampicillin-resistant H. influenzae but also was very effective in vivo in animal infection models. In addition, compound 4 showed great improvement in animal pharmacokinetics properties particularly in dogs with low clearance, excellent oral absorption (bioavailability) and AUC (area under the curve).

| Animal Models of Infection of Compound 4 in Mice and Rats $ED_{50}$ (mg/kg) for MPT and 2Log Red for RLI | | | | | |
|---|---|---|---|---|---|
| | | Compound 4 | | Telithromycin (Tel) | |
| Model | | MIC | $ED_{50}$ | MIC | $ED_{50}$ |
| S. aureus | Smith MPT | 0.25 | 9 | 0.13 | 11 |
| S. pneumoniae | 7701 MPT | <=0.06 | 9 | 0.25 | 10 |
| H. influenzae | 1435 RLI | 4 | 33 | 2 | 49 |
| H. influenzae | S1280 RLI | 8 | 46 | 2 | 56 |
| H. influenzae | 3643 RLI | 16 | 64 | 4 | 78 |

MPT = mouse protection test model;
RLI = rat lung infection model

| Oral Pharmacokinetics of Compound 4 in Different Species | | | | | | | | |
|---|---|---|---|---|---|---|---|---|
| Species | Dose (mg/kg) | Vd (L/kg) | $CL_F$ (L/hr · kg) | $T_{1/2}$ (hr) | $C_{max}$ (µg/mL) | $T_{max}$ (hr) | $AUC_{0-24}$ (µg · hr/mL) | F (%) |
| Mice | 15 | 6.8 | 1.6 | 2.4 | 2.43 | 0.5 | 9.8 | 100 |
| Rat | 10 | 1.97 | 0.64 | 2.1 | 2.54 | 1.7 | 13.89 | 87 |
| Dog | 5 | 1.0 | 0.10 | 7.3 | 2.47 | 1.3 | 32.6 | 71 |
| Dog | 10 | 1.54 | 0.10 | 15.8 | 5.04 | 6.0 | 84.4 | 100 |

| Oral Pharmacokinetics of Compound 4 in Rat Plasma and Lung Tissue | | | | | | | | |
|---|---|---|---|---|---|---|---|---|
| Dose mg/kg | Dose Route | Organ | $C_{max}$ (µg/ml) | $T_{max}$ (hr) | $T_{1/2}$ (hr) | $AUC_{0-24}$ (µg · hr/mL) | Cmax Lung/plasma | AUC Lung/Plasma |
| 10 | PO | Plasma | 2.54 ± 0.08 | 1.67 ± 1.15 | 2.06 ± 0.45 | 13.89 ± 2.81 | | |
| 10 | PO | Lung | 19.00 ± 0.08 | 2.33 ± 1.15 | 2.51 ± 0.10 | 110.34 ± 12.94 | 7.5 ± 1.0 | 8.0 ± 0.9 |

Thus, compound (1) and compound (4) are highly potent macrolides with potential to be a new antibacterial agent for the treatment against broad spectrum of resistant against MRSA infections such as skin and soft tissue infection and/or respiratory tract pathogens with good in vivo efficacies, excellent pharmacokinetics and high lung tissue distribution.

Although the invention has been described with respect to various preferred embodiments, it is not intended to be limited thereto, but rather those skilled in the art will recognize that variations and modifications may be made therein which are within the spirit of the invention and the scope of the appended claims.

What is claimed:
1. A compound represented by the formula (I) or (II):

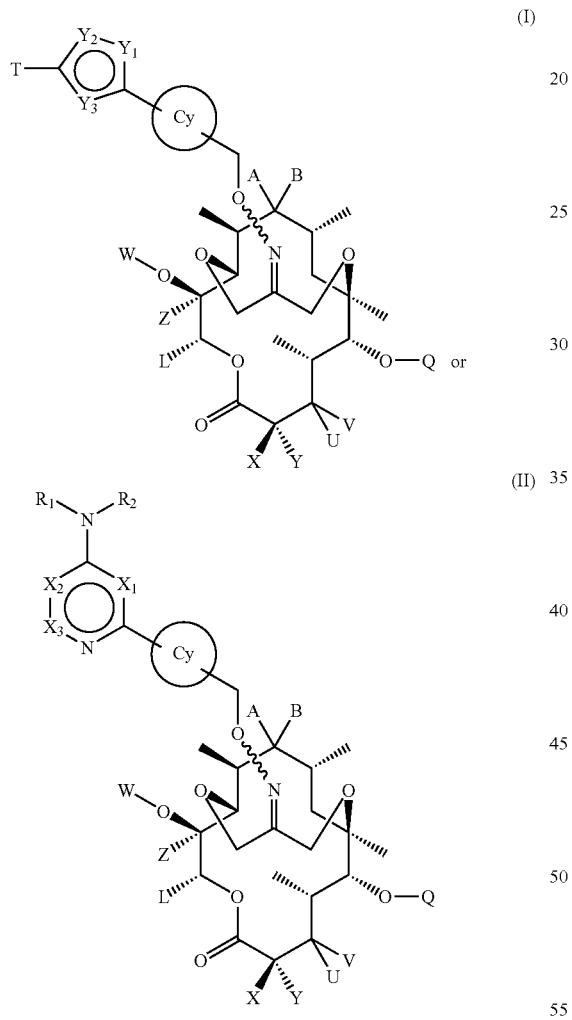

or a pharmaceutically acceptable salt or ester thereof, wherein:

T is hydrogen, $OR_3$, halogen or $NR_1R_2$, wherein $R_1$ and $R_2$ are each independently selected from:
 (a) hydrogen;
 (b) —$R_3$, wherein $R_3$ is substituted or unsubstituted —$C_1$-$C_6$ alkyl, —$C_2$-$C_6$ alkenyl, or —$C_2$-$C_6$ alkynyl each containing 0, 1, 2, or 3 heteroatoms selected from O, S or N;
 (c) —C(O)$R_4$; wherein $R_4$ is independently selected from the group consisting of:
  (i) hydrogen;
  (ii) aryl; substituted aryl; heteroaryl; substituted heteroaryl;
  (iii) —$R_3$; and
  (iv) —$R_5$, wherein $R_5$ is substituted and unsubstituted —$C_3$-$C_{12}$ cycloalkyl each containing 0, 1, 2, or 3 heteroatoms selected from O, S or N;
 (d) —C(O)NH$R_4$;
 (e) —C(O)O$R_4$; and
 (f) —S(O)$_2R_4$;
 alternatively, $R_1$ and $R_2$ are taken together with the nitrogen they are attached with to form a fused or non-fused, substituted or unsubstituted heterocyclic ring;

$Y_1$ is S or O;
$Y_2$ and $Y_3$ are each independently selected from N and $CR_{10}$; wherein $R_{10}$ is independently selected from hydrogen, hydroxy, amino, halogen, substituted and unsubstituted alkoxy, substituted or unsubstituted alkylamino, substituted or unsubstituted dialkylamino, $CF_3$, CN, $NO_2$, $N_3$, sulfonyl, acyl, aliphatic, and substituted aliphatic;
provided that when $Y_1$ is S and $Y_2$ is CH or N, T is not hydrogen;
$X_1$, $X_2$ and $X_3$ are each independently selected N or $CR_{10}$;
Cy is substituted or unsubstituted monocyclic heterocyclic, or substituted or unsubstituted monocyclic heteroaryl;
A and B are each independently selected from:
 (a) hydrogen;
 (b) —$R_3$;
 (c) —$OR_4$;
 (d) —OC(O)$R_4$;
 (e) —OC(O)NH$R_4$;
 (f) —OC(O)O$R_4$;
 (g) —$NR_8R_9$; wherein $R_8$ and $R_9$ are each independently selected from $R_3$; alternatively, $R_8$ and $R_9$ taken together with the nitrogen atom to which they are connected form a 3- to 10-membered ring which may optionally contain one or more heterofunctions selected from the group consisting of: —O—, —NH—, —N($C_1$-$C_6$-alkyl)-, —N($R_{10}$)—, —S(O)$_n$—, wherein n=0, 1 or 2, and $R_{10}$ is selected from aryl; substituted aryl; heteroaryl; and substituted heteroaryl;
 (h) —NHC(O)$R_4$;
 (i) —NHS(O)$_2R_4$;
 (j) —NHC(O)O$R_4$; and
 (k) —NHC(O)NH$R_4$;
alternatively, A and B, taken together with the carbon atom to which they are attached, form a group selected from:
 (a) C=O;
 (b) C=N-J-$R_{11}$, wherein J is absent, O, C(O), $SO_2$, NH, NHC(O), NHC(O)NH or $NHSO_2$; and wherein $R_{11}$ is independently selected from halogen and $R_4$;
 (c) C=CH-J-$R_{11}$; and
 (d) substituted or unsubstituted, and saturated or unsaturated 5- to 10-membered heterocyclic;
L is independently selected from $R_3$;
W is selected from:
 (a) hydrogen;
 (b) hydroxy prodrug group;
 (c) —$R_3$;
 (d) —C(O)$R_4$;
 (e) —C(O)O—$R_4$; and
 (f) —C(O)N($R_8R_9$);
Q is:
 (a) —$R_4$;
 (b) —C(O)$R_4$;

(c) —C(O)NHR$_4$;
(d) —C(O)OR$_4$;
(e) —(SO)$_2$R$_4$;
(f) monosaccharide;
(g) disaccharide; or
(h) trisaccharide;

Z is:
(a) hydrogen;
(b) —N$_3$;
(c) —CN;
(d) —NO$_2$;
(e) —C(O)NH$_2$;
(f) —C(O)OH;
(g) —CHO;
(h) —R$_3$;
(i) —C(O)OR$_3$;
(j) —C(O)R$_3$; or
(k) —C(O)NR$_8$R$_9$;

U is hydrogen and V is selected from the group consisting of:
(a) hydrogen;
(b) —OR$_4$;
(c) —OC(O)R$_4$;
(d) —OC(O)NHR$_4$;
(e) —OS(O)$_2$R$_4$;
(f) —O-monosaccharide; and
(g) —O-disaccharide;

alternatively, U and V, taken together with the carbon atom to which they are attached, form C=O; and each of X and Y is independently:
(a) hydrogen;
(b) hydroxy;
(c) NR$_8$R$_9$;
(d) halogen; or
(e) —R$_3$.

2. A compound represented by the formula (Ia):

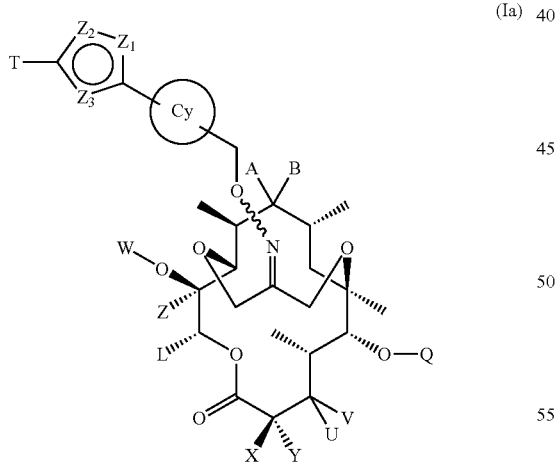

(Ia)

or a pharmaceutically acceptable salt or ester thereof, wherein:

T is hydrogen, OR$_3$, halogen or NR$_1$R$_2$, wherein R$_1$ and R$_2$ are each independently selected from:
(a) hydrogen;
(b) —R$_3$, wherein R$_3$ is substituted or unsubstituted C$_1$-C$_6$ alkyl, C$_2$-C$_6$ alkenyl, or C$_2$-C$_6$ alkynyl each containing 0, 1, 2, or 3 heteroatoms selected from O, S or N;

(c) —C(O)R$_4$; wherein R$_4$ is independently selected from the group consisting of:
(i) hydrogen;
(ii) aryl; substituted aryl; heteroaryl; substituted heteroaryl;
(iii) —R$_3$; and
(iv) —R$_5$, wherein R$_5$ is substituted and unsubstituted C$_3$-C$_{12}$ cycloalkyl each containing 0, 1, 2, or 3 heteroatoms selected from O, S or N;
(d) —C(O)NHR$_4$;
(e) —C(O)OR$_4$;
(f) An amino acid residue; and
(g) —(SO)$_2$R$_4$;

alternatively, R$_1$ and R$_2$ are taken together with the nitrogen atom to which they are attached to form a fused or non-fused, substituted or unsubstituted heterocyclic ring; Z$_1$ is N or CR$_{10}$, Z$_2$ is O, S or CR$_{10}$ and Z$_3$ is N, O, S or CR$_{10}$; wherein R$_{10}$ is independently selected from hydrogen, hydroxy, amino, halogen, substituted or unsubstituted alkoxy, substituted or unsubstituted alkylamino, substituted or unsubstituted dialkylamino, CF$_3$, CN, NO$_2$, N$_3$, sulfonyl, acyl, aliphatic, and substituted aliphatic;

provided that at least two of Z$_1$, Z$_2$ and Z$_3$ are not CR$_{10}$;

Cy is substituted or unsubstituted monocyclic heterocyclic, or substituted or unsubstituted monocyclic heteroaryl;

A and B are each independently selected from:
(a) hydrogen;
(b) —R$_3$;
(c) —OR$_4$;
(d) —OC(O)R$_4$;
(e) —OC(O)NHR$_4$;
(f) —OC(O)OR$_4$;
(g) —NR$_8$R$_9$; wherein R$_8$ and R$_9$ are each independently selected from R$_3$; alternatively, R$_8$ and R$_9$ taken together with the nitrogen atom to which they are connected form a 3- to 10-membered ring which may optionally contain one or more heterofunctions selected from the group consisting of: —O—, —NH—, —N(C$_1$-C$_6$-alkyl)-, —N(R$_{10}$)—, —S(O)$_n$—, wherein n=0, 1 or 2, and R$_{10}$ is selected from aryl; substituted aryl; heteroaryl; and substituted heteroaryl;
(h) —NHC(O)R$_4$;
(i) —NHS(O)$_2$R$_4$;
(j) —NHC(O)OR$_4$; and
(k) —NHC(O)NHR$_4$;

Alternatively, A and B, taken together with the carbon atom to which they are attached, form a group selected from:
(a) C=O;
(b) C=N-J-R$_{11}$, wherein J is absent, O, C(O), SO$_2$, NH, NHC(O), NHC(O)NH or NHSO$_2$; and wherein R$_{11}$ is independently selected from halogen and R$_4$;
(c) C=CH-J-R$_{11}$; and
(d) substituted or unsubstituted, and saturated or unsaturated 5- to 10-membered heterocyclic;

L is independently selected from R$_3$;
W is selected from:
(a) hydrogen;
(b) hydroxy prodrug group;
(c) —R$_3$;
(d) —C(O)R$_4$;
(e) —C(O)O—R$_4$; and
(f) —C(O)N(R$_8$R$_9$);

Q is:
(a) —R$_4$;
(b) —C(O)R$_4$;
(c) —C(O)NHR$_4$;
(d) —C(O)OR$_4$;
(e) —(SO)$_2$R$_4$;
(f) monosaccharide;
(g) disaccharide; or
(h) trisaccharide;

Z is:
(a) hydrogen;
(b) —N$_3$;
(c) —CN;
(d) —NO$_2$;
(e) —C(O)NH$_2$;
(f) —C(O)OH;
(g) —CHO;
(h) —R$_3$;
(i) —C(O)OR$_3$;
(j) —C(O)R$_3$; or
(k) —C(O)NR$_8$R$_9$;

U is hydrogen and V is selected from the group consisting of:
(a) hydrogen;
(b) —OR$_4$;
(c) —OC(O)R$_4$;
(d) —OC(O)NHR$_4$;
(e) —OS(O)$_2$R$_4$;
(f) —O-monosaccharide; and
(g) —O-disaccharide;

alternatively, U and V taken together with the carbon atom to which they are attached form C=O;

X and Y are each independently:
(a) hydrogen;
(b) hydroxy;
(c) NR$_8$R$_9$;
(d) halogen; or
(e) —R$_3$.

3. A compound of Formula IX,

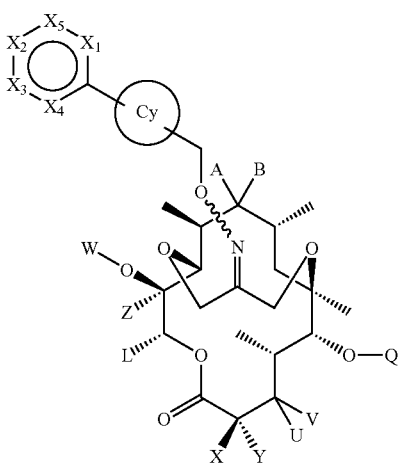

(IX)

or a pharmaceutically acceptable salt or ester thereof, wherein:

$X_1$, $X_2$, $X_3$, $X_4$, and $X_5$ are each independently selected from N and CR$_{10}$, wherein R$_{10}$ is independently selected from hydrogen, hydroxy, amino, halogen, substituted or unsubstituted alkoxy, substituted or unsubstituted alkylamino, substituted or unsubstituted dialkylamino, CF$_3$, CN, NO$_2$, N$_3$, sulfonyl, acyl, aliphatic, and substituted aliphatic;

provided that at least one of $X_1$ to $X_5$ is N and at least one of $X_1$-$X_5$ is C—R$_{10}$, wherein R$_{10}$ is hydrogen or NHR$_1$, wherein R$_1$ is:
(a) hydrogen;
(b) —R$_3$, wherein R$_3$ is substituted or unsubstituted —C$_1$-C$_6$ alkyl, —C$_2$-C$_6$ alkenyl, or —C$_2$-C$_6$ alkynyl each containing 0, 1, 2, or 3 heteroatoms selected from O, S or N;
(c) —C(O)R$_4$; wherein R$_4$ is independently selected from the group consisting of:
(i) hydrogen;
(ii) aryl; substituted aryl; heteroaryl; substituted heteroaryl;
(iii) —R$_3$; and
(iv) —R$_5$, wherein R$_5$ is substituted and unsubstituted —C$_3$-C$_{12}$ cycloalkyl each containing 0, 1, 2, or 3 heteroatoms selected from O, S or N;
(d) —C(O)NHR$_4$;
(e) —C(O)OR$_4$;
(f) —S(O)$_2$R$_4$; or
(g) an amino acid residue;

Cy is selected from the group consisting of substituted or unsubstituted thiadiazole, oxadiazole, thiazole, oxazole, amino pyridine, 2-pyridine wherein the six-membered ring is connected at 5-position, pyrimidine and pyrazine;

A and B are each independently selected from:
(a) hydrogen;
(b) —R$_3$;
(c) —OR$_4$;
(d) —OC(O)R$_4$;
(e) —OC(O)NHR$_4$;
(f) —OC(O)OR$_4$;
(g) —NR$_8$R$_9$; wherein R$_8$ and R$_9$ are each independently selected from R$_3$; alternatively, R$_8$ and R$_9$ taken together with the nitrogen atom to which they are connected form a 3- to 10-membered ring which may optionally contain one or more heterofunctions selected from the group consisting of: —O—, —NH—, —N(C$_1$-C$_6$-alkyl)-, —N(R$_{10}$)—, —S(O)$_n$—, wherein n=0, 1 or 2, and R$_{10}$ is selected from aryl; substituted aryl; heteroaryl; and substituted heteroaryl;
(h) —NHC(O)R$_4$;
(i) —NHS(O)$_2$R$_4$;
(j) —NHC(O)OR$_4$; and
(k) —NHC(O)NHR$_4$;

alternatively, A and B, taken together with the carbon atom to which they are attached, form a group selected from:
(a) C=O;
(b) C=N-J-R$_{11}$, wherein J is absent, O, C(O), SO$_2$, NH, NHC(O), NHC(O)NH or NHSO$_2$; and wherein R$_{11}$ is independently selected from halogen and R$_4$;
(c) C=CH-J-R$_{11}$; and (d) substituted or unsubstituted, and saturated or unsaturated 5- to 10-membered heterocyclic;

L is independently selected from $R_3$;

W is selected from:
(a) hydrogen;
(b) hydroxy prodrug group;
(c) —$R_3$;
(d) —$C(O)R_4$;
(e) —$C(O)O$—$R_4$; and
(f) —$C(O)N(R_8R_9)$;

Q is:
(a) —$R_4$;
(b) —$C(O)R_4$;
(c) —$C(O)NHR_4$;
(d) —$C(O)OR_4$;
(e) —$(SO)_2R_4$;
(f) monosaccharide;
(g) disaccharide; or
(h) trisaccharide;

Z is:
(a) hydrogen;
(b) —$N_3$;
(c) —CN;
(d) —$NO_2$;
(e) —$C(O)NH_2$;
(f) —C(O)OH;
(g) —CHO;
(h) —$R_3$;
(i) —$C(O)OR_3$;
(j) —$C(O)R_3$; or
(k) —$C(O)NR_8R_9$;

U is hydrogen and V is selected from the group consisting of:
(a) hydrogen;
(b) —$OR_4$;
(c) —$OC(O)R_4$;
(d) —$OC(O)NHR_4$;
(e) —$OS(O)_2R_4$;
(f) —O-monosaccharide; and
(g) —O-disaccharide;

alternatively, U and V, taken together with the carbon atom they are attached, form C=O;

each of X and Y is independently:
(a) hydrogen;
(b) hydroxy;
(c) $NR_8R_9$;
(d) halogen; or
(e) —$R_3$.

4. The compound of claim 3 wherein Cy is selected from the group consisting of oxazole and thiazole.

5. The compound of claim 4 wherein
(a) $X_4$ is N, $X_3$ is C—$NHR_1$ and $X_1$, $X_2$ and $X_5$ are CH; or
(b) $X_4$ is C—$NHR_1$, $X_3$ is N and $X_1$, $X_2$ and $X_5$ are CH; or
(c) $X_4$ and $X_2$ are N, $X_3$ and $X_5$ are C—$NHR_1$ and $X_1$ is CH; or
(d) $X_4$ and $X_5$ are N, $X_3$ is C—$NHR_1$ and $X_1$ and $X_2$ are C—H; or
(e) $X_4$ and $X_1$ are N, $X_3$ is C—$NHR_1$ and $X_2$ and $X_5$ are CH; or
(f) $X_4$ is C—$NHR_1$, $X_3$ and $X_1$ are N and $X_2$ and $X_5$ are CH;

where $R_1$ is hydrogen or an amino acid residue.

6. A compound according to claim 1 represented by Formula III,

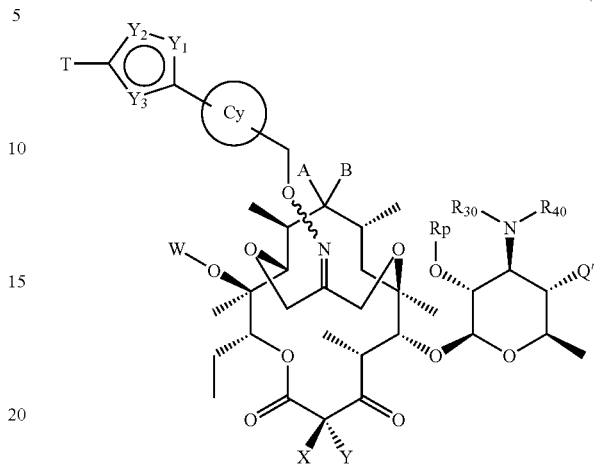

(III)

or a pharmaceutically acceptable salt or ester thereof, wherein $R_p$ is hydrogen, hydroxy protecting group or hydroxy prodrug group;

Q' is:
(a) hydrogen;
(b) $OR_p$; or
(c) —$OR_5$, wherein $R_5$ is selected from the group consisting of:
(i) —$R_3$; and
(ii) substituted and unsubstituted —$C_3$-$C_{12}$ cycloalkyl containing 0, 1, 2, or 3 heteroatoms selected from O, S or N;

$R_{30}$ and $R_{40}$ are each independently selected from the group consisting of hydrogen, acyl, a substituted or unsubstituted, saturated or unsaturated aliphatic group, a substituted or unsubstituted, saturated or unsaturated alicyclic group, a substituted or unsubstituted aromatic group, a substituted or unsubstituted heteroaromatic group, saturated or unsaturated heterocyclic group; or can be taken together with the nitrogen atom to which they are attached to form a substituted or unsubstituted heterocyclic or heteroaromatic ring; and A, B, T, Cy, $Y_1$-$Y_3$, W, X, and Y are as previously defined in claim 1.

7. A compound according to claim 1, represented by formula (IV):

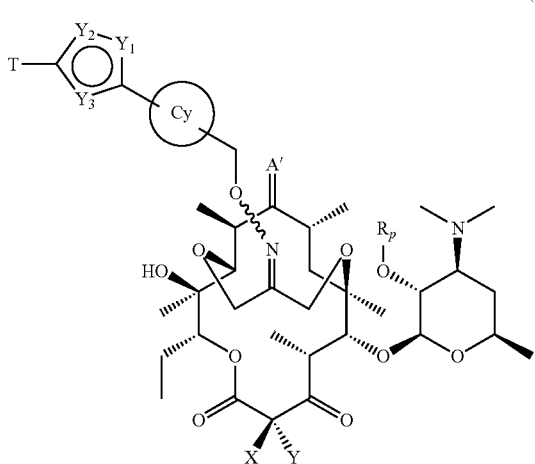

(IV)

or a pharmaceutically acceptable salt or ester thereof, wherein A' is O or NC(O)R$_{11}$; R$_p$ is hydrogen, hydroxy protected protecting group or hydroxy prodrug group; and T, Cy, Y$_1$-Y$_3$, R$_{11}$, X, and Y are as previously defined in claim 1.

8. A compound according to claim 1, represented by formula (V):

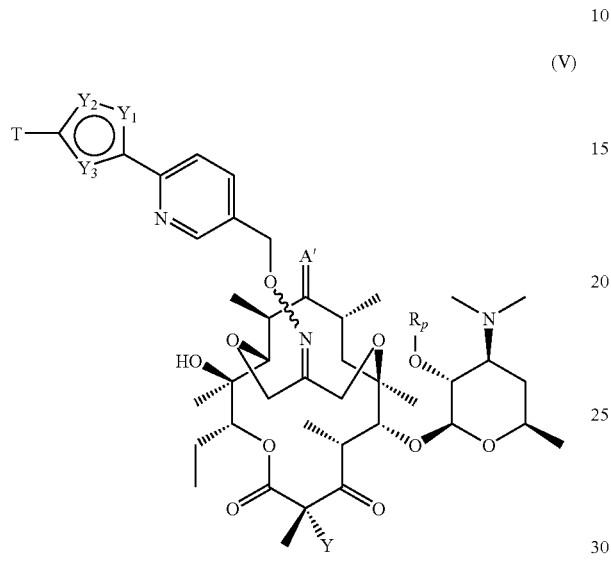

(V)

or a pharmaceutically acceptable salt or ester thereof, wherein A' is O or NC(O)R$_{11}$; R$_p$ is hydrogen, hydroxy protecting group or hydroxy prodrug group; and T, Y$_1$-Y$_3$, R$_{11}$ and Y are as previously defined in claim 1.

9. A compound according to claim 1, represented by formula (VI):

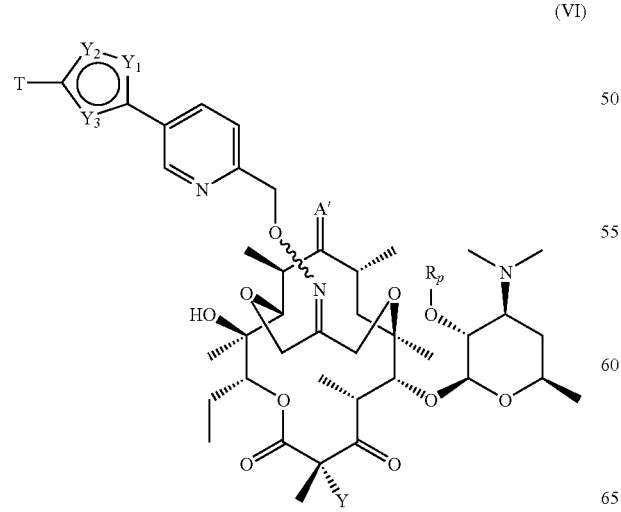

(VI)

or a pharmaceutically acceptable salt or ester thereof, wherein A' is O or NC(O)R$_{11}$; R$_p$ is hydrogen, hydroxy protecting group or hydroxy prodrug group; and T, Y$_1$-Y$_3$, R$_{11}$ and Y are as previously defined in claim 1.

10. A compound according to claim 1, represented by formula (VII):

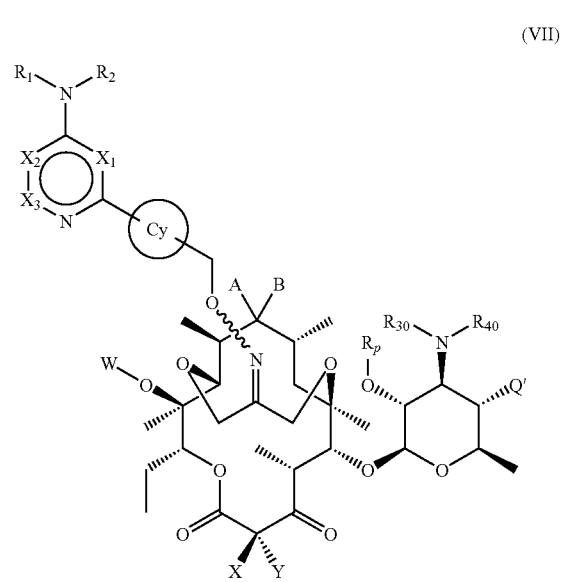

(VII)

or a pharmaceutically acceptable salt or ester thereof, wherein Q' is:

(a) hydrogen;

(b) OR$_p$, where R is hydrogen, a hydroxy protecting group or a hydroxy prodrug group; or (c) —OR$_5$, wherein R$_5$ is selected from the group consisting of:

(i) —R$_3$; and (ii) substituted and unsubstituted C$_3$-C$_{12}$ cycloalkyl containing 0, 1, 2, or 3 heteroatoms selected from O, S or N;

R$_{30}$ and R$_{40}$ are each independently selected from the group consisting of hydrogen, acyl, a substituted or unsubstituted, saturated or unsaturated aliphatic group, a substituted or unsubstituted, saturated or unsaturated alicyclic group, a substituted or unsubstituted aromatic group, a substituted or unsubstituted heteroaromatic group, saturated or unsaturated heterocyclic group; or can be taken together with the nitrogen atom to which they are attached to form a substituted or unsubstituted heterocyclic or heteroaromatic ring; and R$_1$, R$_2$, R$_3$, Cy, X$_1$-X$_3$, W, X, Y, A and B are as previously defined in claim 1.

11. A compound according to claim 1, represented by formula (VIII):

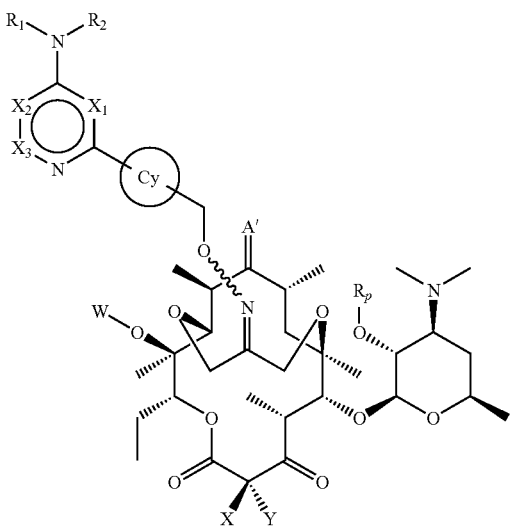

(VIII)

or a pharmaceutically acceptable salt or ester thereof, wherein A' is O or NC(O)$R_{11}$; $R_p$ is hydrogen, hydroxy protected protecting group or hydroxy prodrug group; and $R_1, R_2, X_1$-$X_3, R_{11}$, Cy, W, X and Y are as previously defined in claim 1.

12. A compound according to claim 1 represented by formula (XVI):

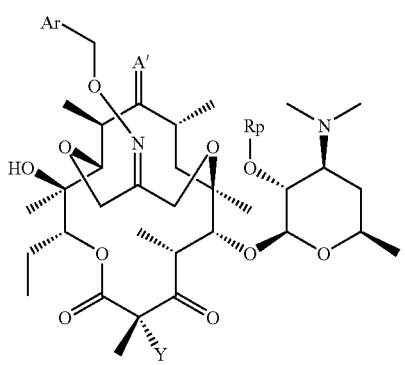

(XVI)

or a pharmaceutically acceptable salt or ester thereof wherein Rp is H, and Ar, Y and A' are selected from the group consisting of:

| | Ar | Y | A' |
|---|---|---|---|
| (a) | | H | NC(O)Me |
| (b) | | H | O |
| (c) | | H | O |
| (d) | | F | NC(O)Et |
| (e) | | H | O |
| (f) | | H | O |
| (g) | | F | NC(O)Et. |

13. A method for treating a bacterial infection in a subject in need of such treatment, comprising administering to said subject a therapeutically effective amount of a compound according to any one of claims 1 to 3.

14. A pharmaceutical composition comprising a therapeutically effective amount of a compound of any one of claims 1 to 3 in combination with a pharmaceutically acceptable carrier.

15. A method for treating a bacterial infection in a subject, comprising administering to said subject a therapeutically effective amount of a pharmaceutical composition according to claim 14.

16. A method for treating cystic fibrosis in a subject, comprising administering to said subject a therapeutically effective amount of a pharmaceutical composition according to claim 14.

17. A method for treating an inflammatory disorder in a subject, comprising administering to said subject a therapeutically effective amount of a pharmaceutical composition according to claim 14.

18. A compound represented by the formula (X):

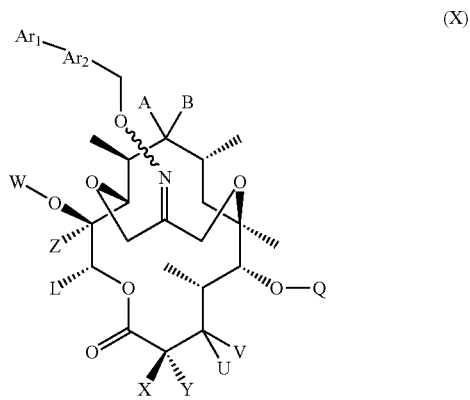

or a pharmaceutically acceptable salt or ester thereof, wherein:

Ar$_1$ is selected from substituted or unsubstituted amino thiazole, amino pyrazole, isoxazole, amino isoxazole, oxadiazole, amino oxadiazole, amino oxazole, 5-amino-1,2,4-thiadiazole, amino triazole, or amino tetrazole; and Ar$_2$ is selected from substituted or unsubstituted thiadiazole, oxadiazole, imidazole, thiazole, pyrazole, oxazole, benzene, pyridine, amino pyridine, pyrimidine or pyrazine; or Ar$_1$ is selected from substituted or unsubstituted amino pyridine, amino pyrimidine or amino pyrazine; and Ar$_2$ is selected from substituted or unsubstituted thiadiazole, oxadiazole, imidazole, thiazole, pyrazole, oxazole, amino pyridine, 2-pyridine or triazole wherein Ar$_1$ is connected at 5-position, pyrimidine or pyrazine;

A and B are each independently selected from:
 (a) hydrogen;
 (b) —R$_3$ wherein R$_3$ is substituted or unsubstituted —C$_1$-C$_6$ alkyl, C—C$_6$ alkenyl, or —C$_2$-C$_6$ alkynyl each containing 0, 1, 2, or 3 heteroatoms selected from O, S or N;
 (c) —OR$_4$ wherein R$_4$ is independently selected from the group consisting of:
  (i) hydrogen;
  (ii) aryl; substituted aryl; heteroaryl; substituted heteroaryl;
  (iii) —R$_3$; and
  (iv) —R$_5$, wherein R$_5$ is substituted and unsubstituted C$_3$-C$_{12}$ cycloalkyl each containing 0, 1, 2, or 3 heteroatoms selected from O, S or N;
 (d) —OC(O)R$_4$;
 (e) —OC(O)NHR$_4$;
 (f) —OC(O)OR$_4$;
 (g) —NR$_8$R$_9$; wherein R$_8$ and R$_9$ are each independently selected from R$_3$; alternatively, R$_8$ and R$_9$ taken together with the nitrogen atom to which they are connected form a 3- to 10-membered ring which may optionally contain one or more heterofunctions selected from the group consisting of: —O—, —NH—, —N(R$_4$)—, —S(O)$_n$—, wherein n=0, 1 or 2;
 (h) —NHC(O)R$_4$;
 (i) —NHSO$_2$R$_4$;
 (j) —NHC(O)OR$_4$; and
 (k) —NHC(O)NHR$_4$;

Alternatively, A and B taken together with the carbon atom to which they are attached are selected from:
 (a) C=O;
 (b) C=N-J-R$_{11}$, wherein J is absent, O, C(O), SO$_2$, NH, NHC(O), NHC(O)NH or NHSO$_2$; and wherein R$_{11}$ is independently selected from halogen, NO$_2$ and R$_4$;
 (c) C=CH-J-R$_{11}$;
 (d) substituted or unsubstituted, and saturated or unsaturated 5- to 10-membered heterocyclic;

L is independently selected from R$_3$;

W is selected from:
 (a) hydrogen;
 (b) hydroxy prodrug group;
 (c) —R$_3$;
 (d) —C(O)R$_4$;
 (e) —C(O)O—R$_4$; and
 (f) —C(O)N(R$_8$R$_9$);

Q is:
 (a) —R$_4$;
 (b) —C(O)R$_4$;
 (c) —C(O)NHR$_4$;
 (d) —C(O)OR$_4$;
 (e) —S(O)$_2$R$_4$;
 (f) monosaccharide;
 (g) disaccharide; or
 (h) trisaccharide;

Z is:
 (a) hydrogen;
 (b) —N$_3$;
 (c) —CN;
 (d) —NO$_2$;
 (e) —C(O)NH$_2$;
 (f) —C(O)OH;
 (g) —CHO;
 (h) —R$_3$;
 (i) —C(O)OR$_3$;
 (j) —C(O)R$_3$; or
 (k) —C(O)NR$_8$R$_9$;

U is hydrogen, V is selected from the group consisting of:
 (a) hydrogen;
 (b) —OR$_4$;
 (c) —OC(O)R$_4$;
 (d) —OC(O)NHR$_4$;
 (e) —OS(O)$_2$R$_4$;
 (f) —O-monosaccharide; and
 (g) —O-disaccharide;

Or alternatively, U and V taken together with the carbon atom they are attached is C=O;

each of X and Y is independently selected from:
 (a) hydrogen;
 (b) hydroxy;
 (c) NR$_8$R$_9$;
 (d) halogen; or
 (e) —R$_3$;

provided that the compound is not

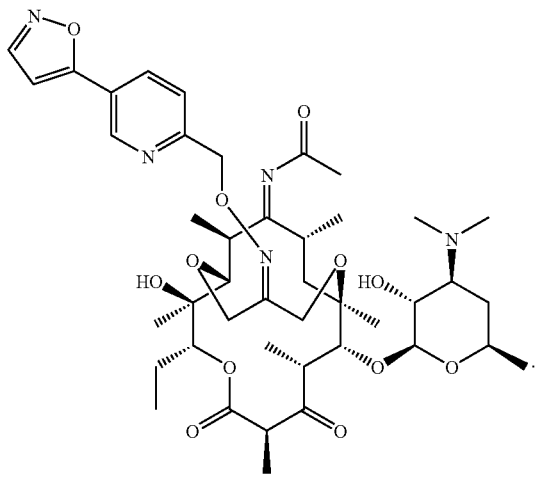 [SMILES: CC[C@H]1OC(=O)[C@H](C)C(=O)[C@H](C)[C@@H](O[C@@H]2O[C@H](C)C[C@H](N(C)C)[C@H]2O)[C@@]2(C)C[C@@H](C)/C(=N\C(C)=O)[C@H](C)[C@@H](OC/C(=N\OCc3ccc(-c4ccno4)cn3)CO2)[C@]1(C)O]

19. A compound according to claim 18, represented by formula (XI):

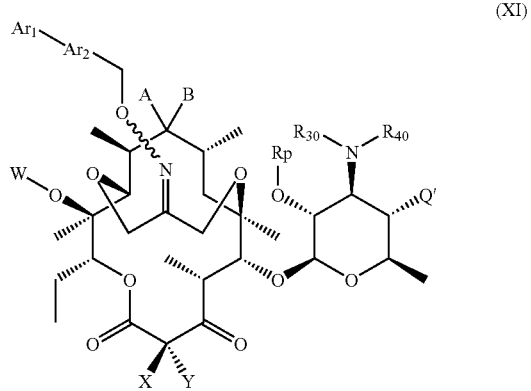

or a pharmaceutically acceptable salt or ester thereof,
wherein $R_p$ is hydrogen, hydroxy protecting group or hydroxy prodrug group;
Q' is:
  (a) hydrogen;
  (b) $OR_p$; or
  (c) —$OR_5$, wherein $R_5$ is selected from the group consisting of:
    (i) —$R_3$; and
    (ii) substituted and unsubstituted $C_3$-$C_{12}$ cycloalkyl containing 0, 1, 2, or 3 heteroatoms selected from O, S or N;
$R_{30}$ and $R_{40}$ are independently selected from the group consisting of hydrogen, acyl, a substituted or unsubstituted, saturated or unsaturated aliphatic group, a substituted or unsubstituted, saturated or unsaturated alicyclic group, a substituted or unsubstituted aromatic group, a substituted or unsubstituted heteroaromatic group, saturated or unsaturated heterocyclic group; or can be taken together with the nitrogen atom to which they are attached to form a substituted or unsubstituted heterocyclic or heteroaromatic ring; and $Ar_1$, $Ar_2$, W, X, Y, A and B are as previously defined in claim 18.

20. A compound according to claim 19 wherein $Ar_1$ is aminopyrazole.

21. A compound according to claim 19 represented by formula (XII):

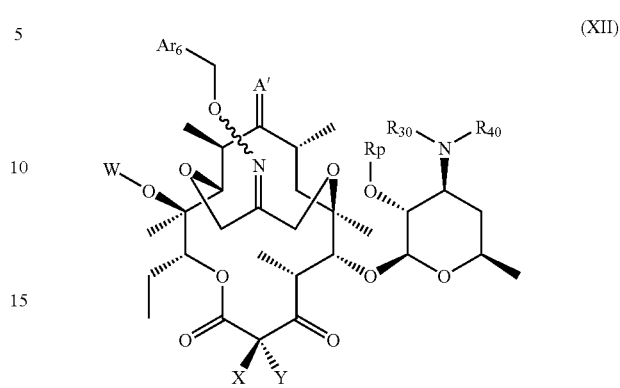

or a pharmaceutically acceptable salt, amide or ester thereof, wherein $R_p$, $R_{30}$, $R_{40}$, W, X and Y are as previously defined in claim 19;
A', together with the carbon atom to which it is attached, is selected from:
  (a) C=O;
  (b) C=N-G-$R_{11}$, wherein G is absent, O, C(O), $SO_2$, NH, NHC(O), NHC(O)NH or $NHSO_2$; and wherein $R_{11}$ is independently selected from halogen and $R_4$;
  (c) C=CH-G-$R_{11}$;
  (d) substituted or unsubstituted, and saturated or unsaturated 5- to 10-membered heterocyclic;
$Ar_6$ is selected from the groups set forth below:

| $Ar_6$ |
| --- |

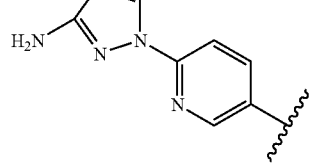

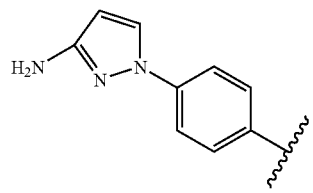

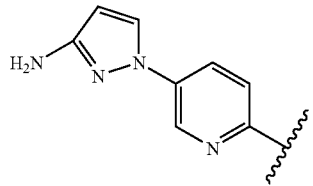

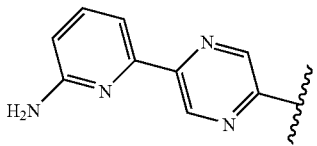 [SMILES: *c1cnc(-c2cccc(N)n2)cn1]

| 199 -continued | 200 -continued |
|---|---|
| Ar₆ | Ar₆ |
| 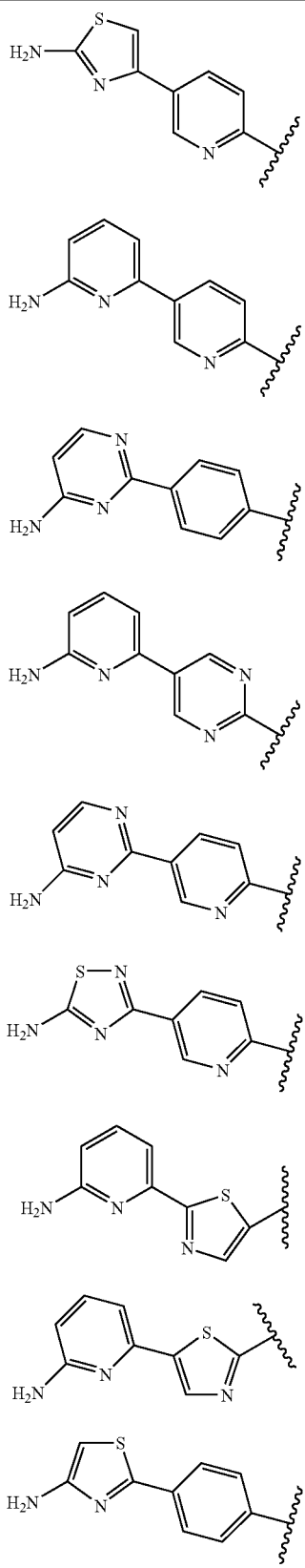 | 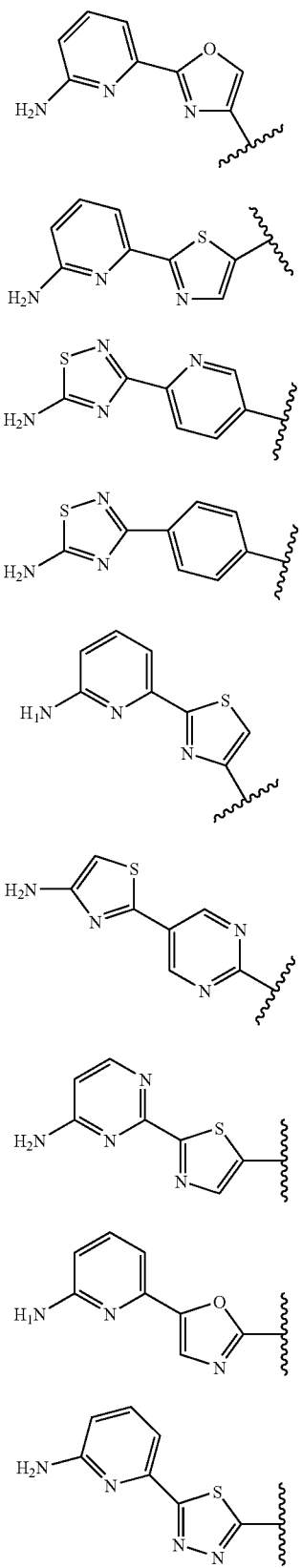 |

| 201 -continued | 202 -continued |
|---|---|
| Ar_6 | Ar_6 |
| 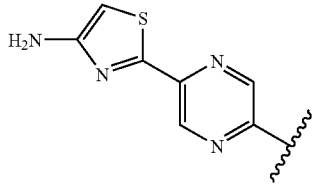 [SMILES: *c1cnc(-c2nc(N)cs2)cn1] | 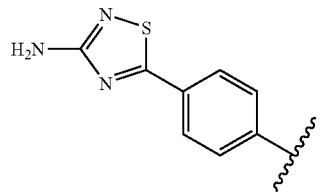 |
| 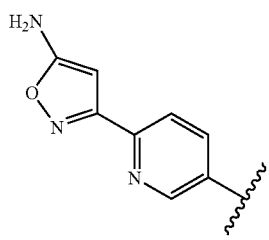 [SMILES: *c1ccc(-c2cc(N)on2)nc1] | 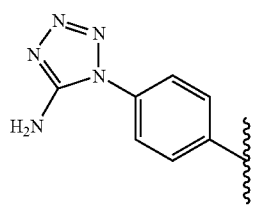 |
| 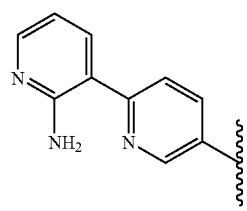 [SMILES: *c1ccc(-c2cccnc2N)nc1] | 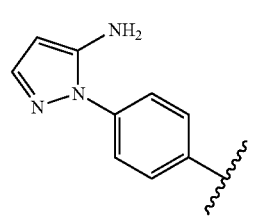 |
| 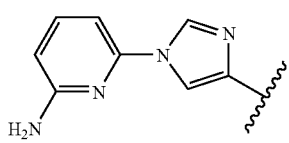 | 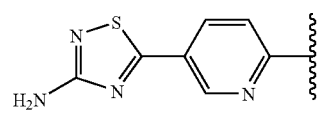 |
| 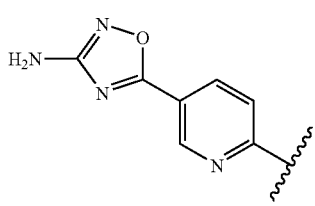 [SMILES: *c1ccc(-c2nc(N)no2)cn1] | 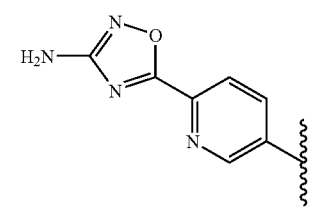 |
| 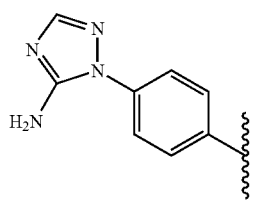 [SMILES: *c1ccc(-n2ncnc2N)cc1] | 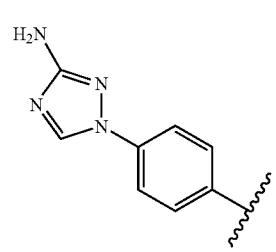 |
| 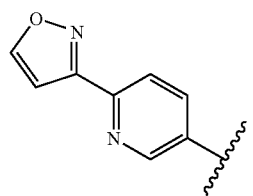 [SMILES: *c1ccc(-c2ccon2)nc1] | 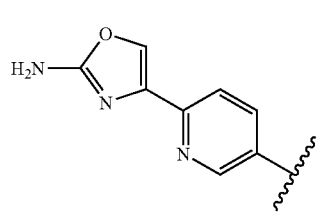 [SMILES: *c1ccc(-c2coc(N)n2)nc1] |
| | 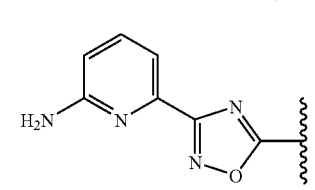 [SMILES: *c1nc(-c2cccc(N)n2)no1] |

| Ar6 |
|---|
| 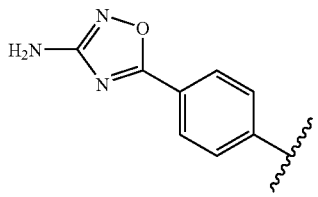 |
| 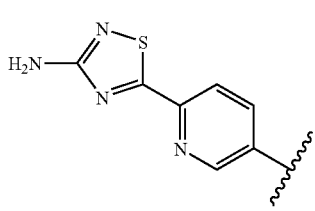 |
| 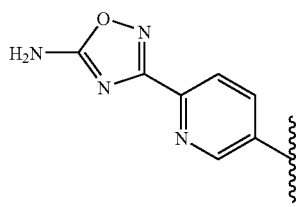 [SMILES: *c1ccc(-c2noc(N)n2)nc1] |
| 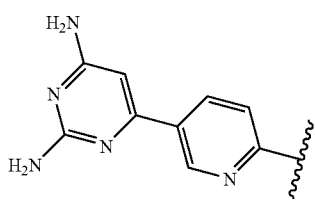 [SMILES: *c1ccc(-c2cc(N)nc(N)n2)cn1] |
| 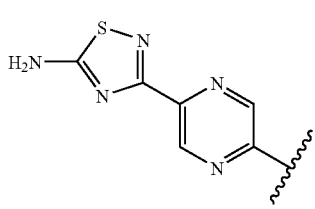 [SMILES: *c1cnc(-c2nsc(N)n2)cn1] |
| 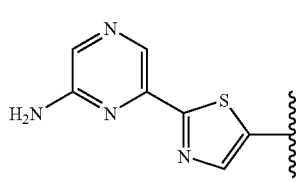 [SMILES: *c1cnc(-c2cncc(N)n2)s1] |
| 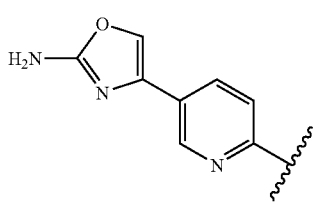 |

| Ar6 |
|---|
| 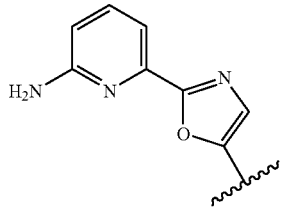 [SMILES: *c1cnc(-c2cccc(N)n2)o1] |
| 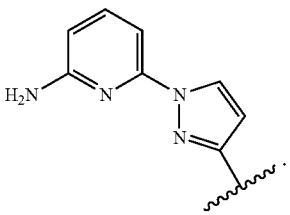 [SMILES: *c1ccn(-c2cccc(N)n2)n1] |

22. A compound according to claim 19 represented by formula (XII):

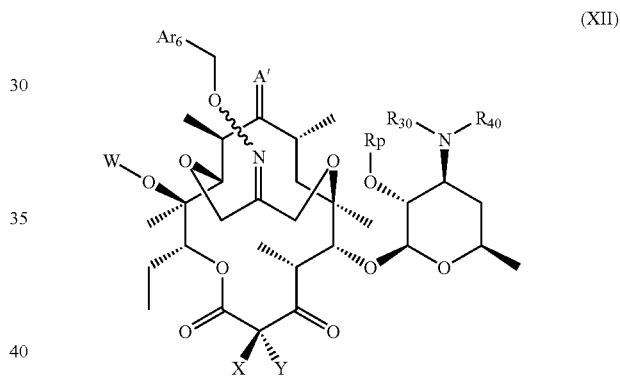

or a pharmaceutically acceptable salt, amide or ester thereof, wherein $R_p$, $R_{30}$, $R_{40}$, W, X and Y are as previously defined in claim 19;

A' is selected from:
- (a) C=O;
- (b) C=N-J-$R_{11}$, wherein J is absent, O, C(O), SO$_2$, NH, NHC(O), NHC(O)NH or NHSO$_2$; and wherein $R_{11}$ is independently selected from halogen and $R_4$;
- (c) C=CH-J-$R_{11}$;
- (d) substituted or unsubstituted, and saturated or unsaturated 5- to 10-membered heterocyclic; and $Ar_6$ is selected from the groups set forth below:

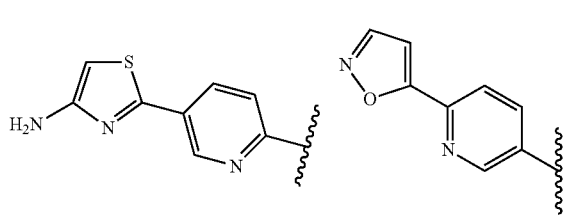

-continued

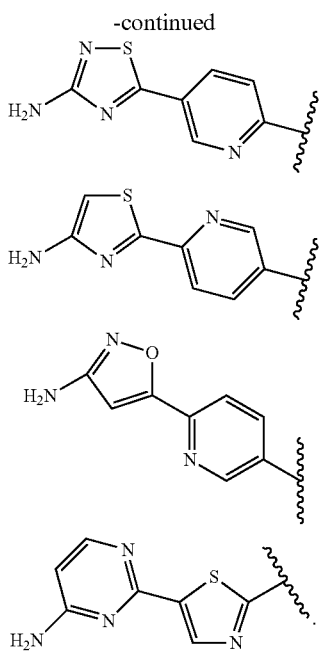

23. A compound according to claim 18, represented by formula (XIII):

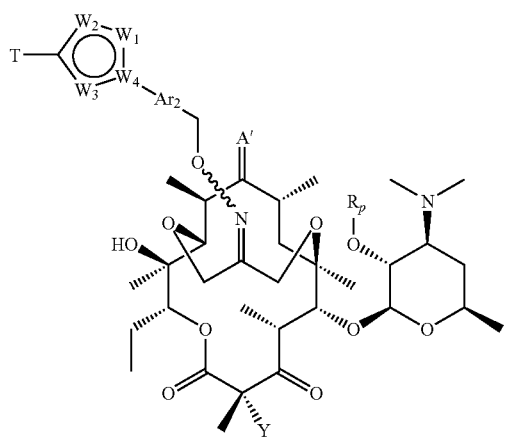

(XIII)

or a pharmaceutically acceptable salt or ester thereof, wherein A' is O or NC(O)$R_{11}$; $R_p$ is hydrogen, hydroxy protecting group or hydroxy prodrug group; and T is $NR_1R_2$, where $R_1$ and $R_2$ are each independently selected from:

(a) hydrogen;

(b) —$R_3$, where $R_3$ is substituted or unsubstituted $C_1$-$C_6$ alkyl, $C_2$-$C_6$ alkenyl, or $C_2$-$C_6$ alkynyl each containing 0, 1, 2, or 3 heteroatoms selected from O, S or N;

(c) —C(O)$R_4$; where $R_4$ is independently selected from the group consisting of:
  (i) hydrogen;
  (ii) aryl; substituted aryl; heteroaryl; substituted heteroaryl;
  (iii) —$R_3$; and
  (iv) —$R_5$, where $R_5$ is substituted and unsubstituted $C_3$-$C_{12}$ cycloalkyl each containing 0, 1, 2, or 3 heteroatoms selected from O, S or N;

(d) —C(O)NH$R_4$;

(e) —C(O)O$R_4$;

(f) an amino acid residue;

(g) ($R_3$O)($R_4$O)P(O)—; and (h) —S(O)$_2R_4$;

alternatively, $R_1$ and $R_2$ can be taken together with the nitrogen they are attached with to form a fused or non-fused, substituted or unsubstituted heterocyclic ring;

$W_1$, $W_2$ and $W_3$ are each independently selected from S, N, O or $CR_{10}$ wherein $R_{10}$ is independently selected from hydrogen, hydroxy, amino, halogen, substituted or unsubstituted alkoxy, substituted or unsubstituted alkylamino, substituted or unsubstituted dialkylamino, $CF_3$, CN, $NO_2$, $N_3$, sulfonyl, acyl, aliphatic, and substituted aliphatic, $W_4$ is N or C;

provided that $W_1$, $W_2$, $W_3$ and $W_4$ are selected such that the five-membered ring to which they belong is thiazole, pyrazole, isoxazole, oxadiazole, oxazole, 1,2,4-thiadiazole, triazole, or tetrazole; and $Ar_2$, $R_{11}$ and Y are as previously defined in claim 18.

24. A compound according to claim 23, represented by formula (XIV):

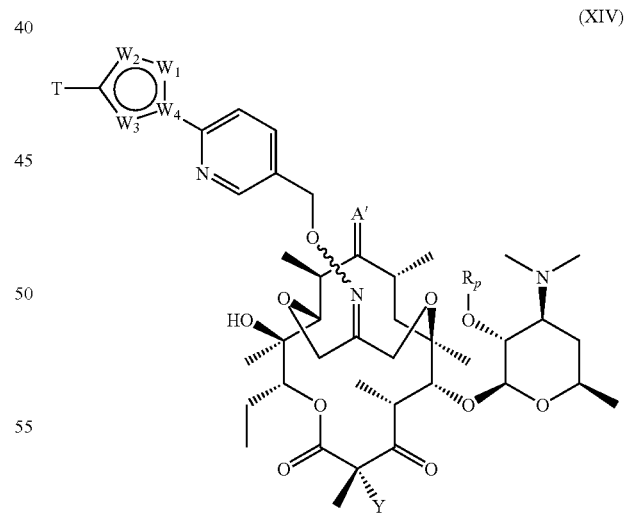

(XIV)

or a pharmaceutically acceptable salt or ester thereof, wherein A' is O or NC(O)$R_{11}$; $R_p$ is hydrogen, hydroxy protected protecting group or hydroxy prodrug group; and T, $W_1$-$W_4$, $R_{11}$ and Y are as previously defined in claim 23.

25. A compound according to claim 23, represented by formula (XV):

(XV)

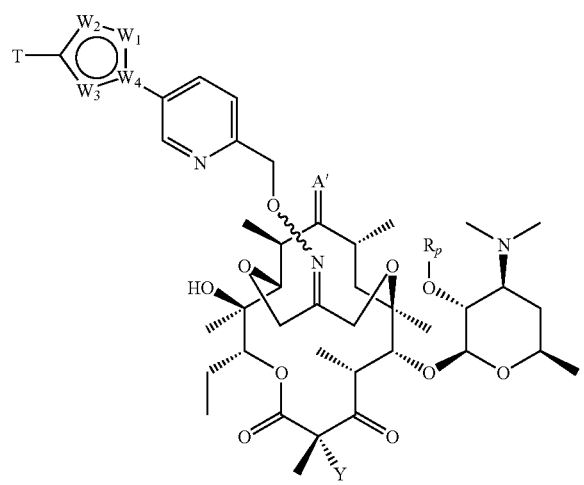

or a pharmaceutically acceptable salt or ester thereof, wherein A' is O or NC(O)R$_{11}$; R$_p$ is hydrogen, hydroxy protecting group or hydroxy prodrug group; and T, W$_1$-W$_4$, R$_{11}$ and Y are as previously defined in claim 23.

26. A compound represented by formula (XVI):

(XVI)

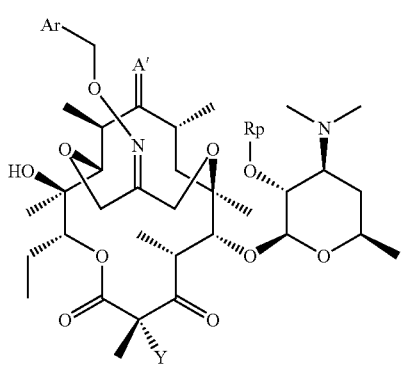

or a pharmaceutically acceptable salt, amide or ester thereof where Rp is H and Ar, Y and A' are selected from the group consisting of:

| | Ar | Y | A' |
|---|---|---|---|
| (a) | 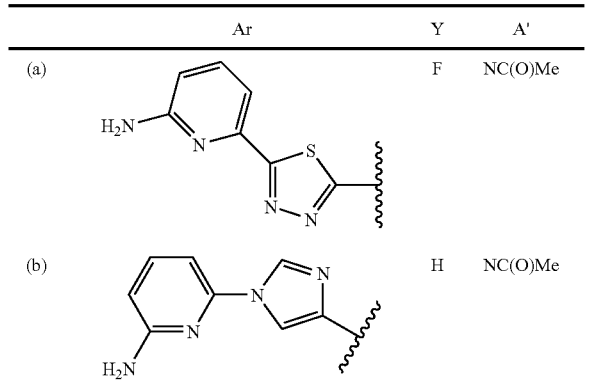 | F | NC(O)Me |
| (b) | 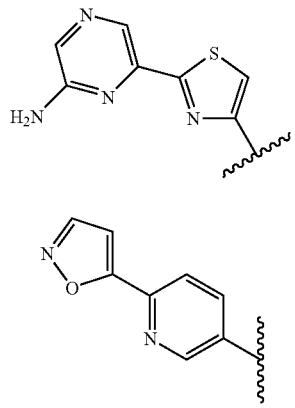 | H | NC(O)Me |
| (c) | 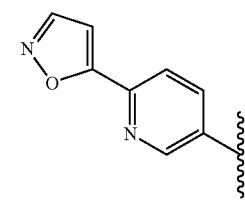 [SMILES: *c1ccc(-c2ccno2)nc1] | H | O |
| (d) | 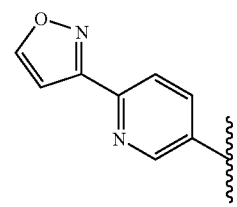 [SMILES: *c1ccc(-c2ccon2)nc1] | H | O |
| (e) | 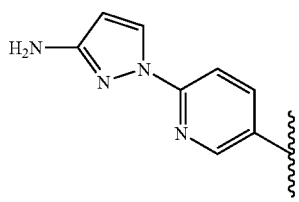 [SMILES: *c1ccc(-n2ccc(N)n2)nc1] | H | O |
| (f) | 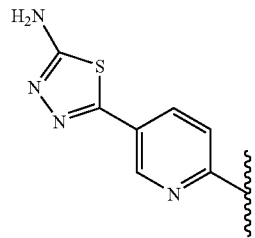 [SMILES: *c1ccc(-c2nnc(N)s2)cn1] | H | O |
| (g) | 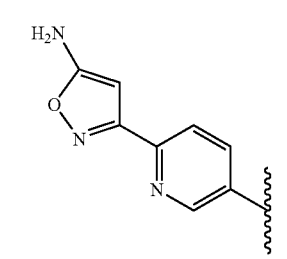 [SMILES: *c1ccc(-c2cc(N)on2)nc1] | H | O |
| (h) | 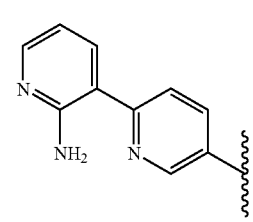 [SMILES: *c1ccc(-c2cccnc2N)nc1] | H | NC(O)Me |
| (i) | | H | NC(O)Me |

| | Ar | Y | A' |
|---|---|---|---|
| (j) | 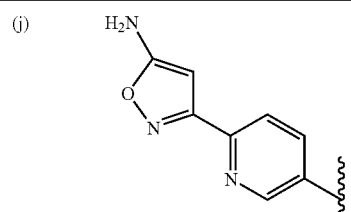 | H | O |
| (k) | 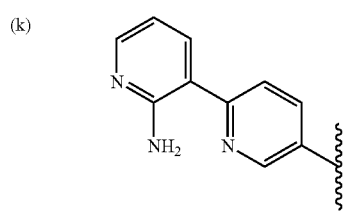 | H | O |
| (l) | 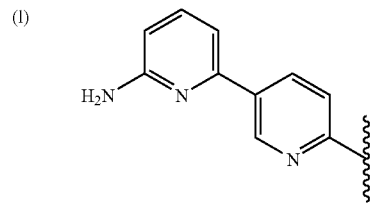 | F | NH |
| (m) | 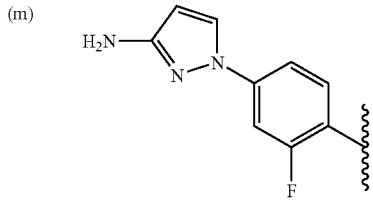 | F | O |
| (n) | 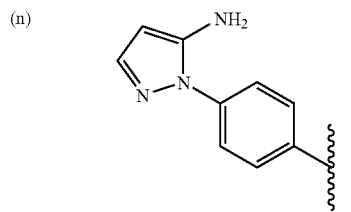 | F | NC(O)Me |
| (o) | 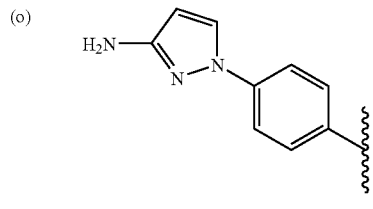 | F | O |
| (p) | 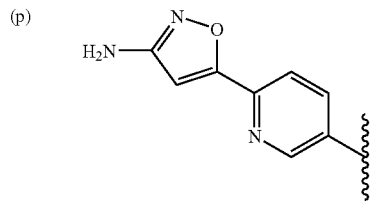 | F | O |
| | Ar | Y | A' |
|---|---|---|---|
| (q) | 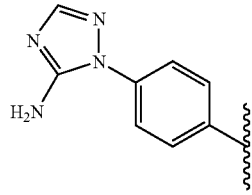 [SMILES: *c1ccc(-n2ncnc2N)cc1] | F | NC(O)Me |
| (r) | 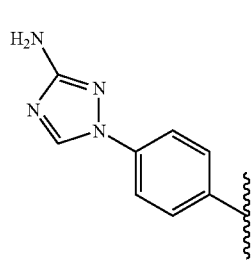 [SMILES: *c1ccc(-n2cnc(N)n2)cc1] | F | NC(O)Me |
| (s) | 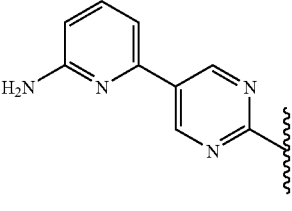 [SMILES: *c1ncc(-c2cccc(N)n2)cn1] | F | NC(O)Me |
| (t) | 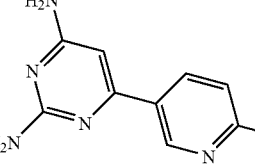 | F | NC(O)Me |
| (u) | 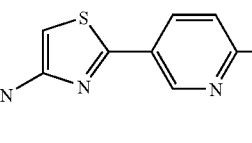 | H | O |
| (v) | 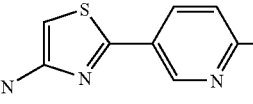 | F | O |
| (w) | 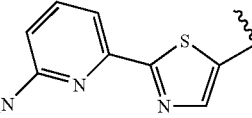 | H | O |
| (x) | 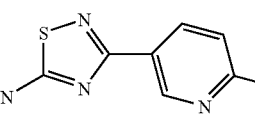 | H | O |
| (y) | 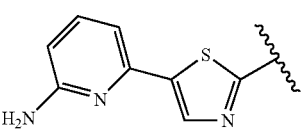 | H | O |

| | Ar | Y | A' |
|---|---|---|---|
| (z) | 6-aminopyridin-2-yl-thiazol-5-yl | H | NC(O)Me |
| (aa) | 3-amino-1,2,4-oxadiazol-5-yl-phenyl | F | O |
| (bb) | 6-aminopyridin-2-yl-oxazol-4-yl | H | O |
| (cc) | 6-aminopyridin-2-yl-oxazol-4-yl | H | NC(O)Me |
| (dd) | 6-aminopyridin-2-yl-thiazol-4-yl | F | O |
| (ee) | 3-amino-1,2,4-oxadiazol-5-yl-phenyl | H | O |
| (ff) | 3-amino-1,2,4-oxadiazol-5-yl-pyridin-2-yl | F | O |
| (gg) | 3-amino-1,2,4-thiadiazol-5-yl-phenyl | H | O |

| | Ar | Y | A' |
|---|---|---|---|
| (hh) | 3-amino-1,2,4-oxadiazol-5-yl-pyridin-2-yl | H | O |
| (ii) | 5-amino-tetrazol-1-yl-phenyl | H | O |
| (jj) | 5-amino-tetrazol-1-yl-phenyl | H | NC(O)Me |
| (kk) | 5-amino-1,2,4-thiadiazol-3-yl-phenyl | H | NC(O)Me |
| (ll) | 2-aminothiazol-4-yl-pyridin-2-yl | H | O |
| (mm) | 3-aminopyrazol-1-yl-pyridin-2-yl | F | O |
| (nn) | 6-aminopyridin-3-yl-pyrimidin-2-yl | H | O |
| (oo) | 3-amino-1,2,4-oxadiazol-5-yl-pyridin-2-yl | H | O |

| | Ar | Y | A' |
|---|---|---|---|
| (pp) | 6-amino-pyridin-2-yl-1,2,4-oxadiazol-5-yl | F | O |
| (qq) | 6-amino-pyridin-2-yl-1,2,4-oxadiazol-5-yl (isomer) | H | O |
| (rr) | 2-amino-oxazol-4-yl-pyridin-5-yl | H | O |
| (ss) | 3-amino-1,2,4-thiadiazol-5-yl-phenyl | F | O |
| (tt) | 6-amino-pyridin-2-yl-pyrazol-3-yl | F | NC(O)Et |
| (uu) | 6-amino-pyridin-2-yl-pyrazol-3-yl | H | O |
| (vv) | 2-amino-oxazol-4-yl-pyridin-5-yl | H | O |
| (ww) | 5-amino-1,2,4-oxadiazol-3-yl-pyridin-5-yl | H | O |
| (xx) | 6-amino-pyridin-3-yl-thiazol-2-yl | H | O |
| (yy) | 3-amino-1,2,4-thiadiazol-5-yl-pyrazin-5-yl | F | O |
| (zz) | 6-amino-pyridin-2-yl-oxazol-5-yl | F | NC(O)Et |
| (aaa) | 6-amino-pyridin-2-yl-oxazol-5-yl | H | O |
| (bbb) | 5-amino-1,2,4-thiadiazol-3-yl-pyrazin-5-yl | F | NC(O)Et |
| (ccc) | 5-amino-1,2,4-thiadiazol-3-yl-pyrazin-5-yl | H | O |
| (ddd) | 6-amino-pyridin-2-yl-oxazol-5-yl | H | NC(O)Me |

| | Ar | Y | A' |
|---|---|---|---|
| (eee) | (pyridine-thiazole with H₂N) | H | O. |

27. A compound according to claim 18 represented by formula (XVI):

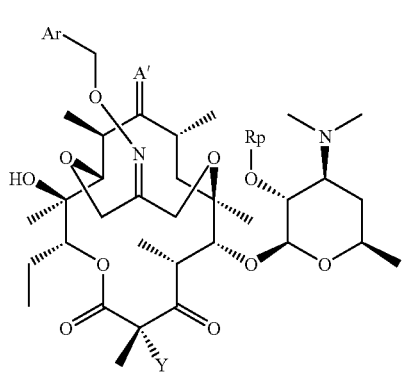

(XVI)

or a pharmaceutically acceptable salt, amide or ester thereof wherein Rp is H, and Ar, Y and A' are selected from the group consisting of:

| | Ar | Y | A' |
|---|---|---|---|
| (a) | (aminothiadiazole-pyridine) | F | NC(O)Et |
| (b) | (aminopyrazole-pyridine) | F | NC(O)Me |
| (c) | (aminopyridine-thiazole) | F | NC(O)-isopropyl |
| (d) | (aminopyridine-pyridine) | F | NC(O)Me |
| (e) | (aminopyridine-pyridine) | F | NC(O)Et |
| (f) | (aminopyridine-pyridine) | F | NC(O)-propyl |
| (g) | (aminopyridine-pyridine) | F | NC(O)-cyclopropyl |
| (h) | (aminopyrazole-pyridine) | F | NC(O)Et |
| (i) | (aminopyridine-pyridine) | F | NC(O)-isopropyl |
| (j) | (aminopyrazole-phenyl) | F | NC(O)Me |
| (k) | (aminopyrazole-pyridine) | F | NC(O)Me |

| | Ar | Y | A' |
|---|---|---|---|
| (l) | 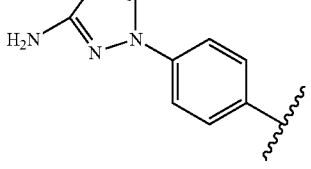 | H | NC(O)Et |
| (m) | 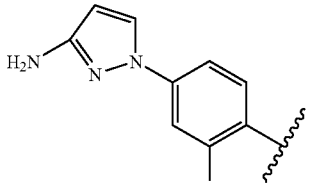 | H | NC(O)Me |
| (n) | 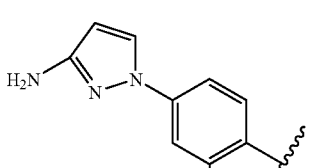 | F | NC(O)Me |
| (o) | 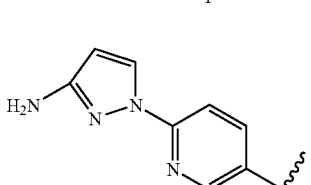 | F | NC(O)-isopropyl |
| (p) | 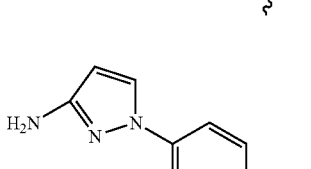 | F | NC(O)-isopropyl |
| (q) | 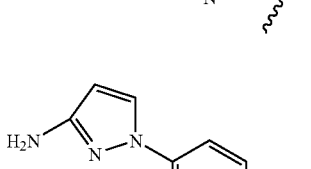 | H | NC(O)Me |
| (r) | 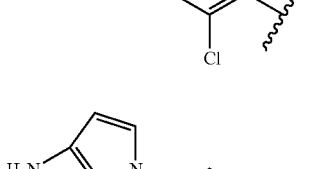 | F | NC(O)Me |
| | Ar | Y | A' |
|---|---|---|---|
| (s) | 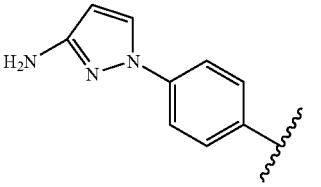 [SMILES: *c1ccc(-n2ccc(N)n2)cc1] | H | NC(O)-isopropyl |
| (t) | 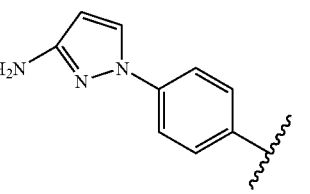 | F | NC(O)-isopropyl |
| (u) | 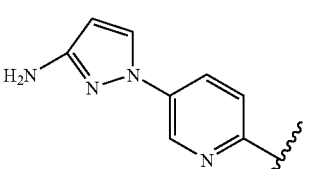 | F | NC(O)Et |
| (v) | 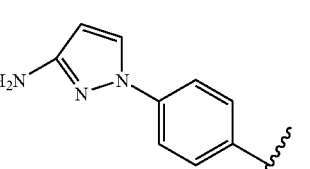 | F | NC(O)-cyclopropyl |
| (w) | 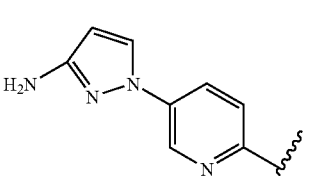 | F | NC(O)-cyclopropyl |
| (x) | 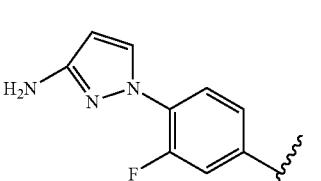 | F | NC(O)Me |
| (y) | 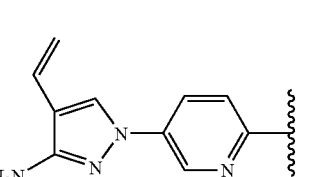 | F | NC(O)Me |
| (z) | 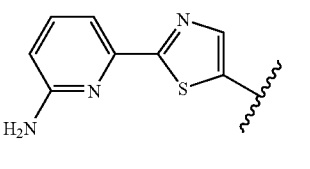 | F | NC(O)Me |

-continued

| | Ar | Y | A' |
|---|---|---|---|
| (aa) | 3-amino-1-(3-fluoro-4-yl-phenyl)pyrazole | H | NC(O)-isopropyl |
| (bb) | 3-amino-1-(3-methoxy-4-yl-phenyl)pyrazole | F | NC(O)Me |
| (cc) | 6-amino-2-(pyrimidin-2-yl)pyridine | F | NC(O)-isopropyl |
| (dd) | 4-amino-2-(pyridin-5-yl)thiazole | F | NC(O)Me |
| (ee) | 4-amino-2-(pyridin-5-yl)pyrimidine | F | NC(O)Me |
| (ff) | 6-amino-2-(pyrazin-5-yl)pyridine | F | NC(O)Me |
| (gg) | 2-amino-4-(pyridin-5-yl)thiazole | F | NC(O)Me |
| (hh) | 4-amino-2-(phenyl)pyrimidine | F | NC(O)Me |
| (ii) | 6-amino-2-(thiazol-5-yl)pyridine | F | NC(O)Me |

-continued

| | Ar | Y | A' |
|---|---|---|---|
| (jj) | 5-amino-3-(pyridin-5-yl)-1,2,4-thiadiazole | F | NC(O)Me |
| (kk) | 4-amino-2-(pyridin-5-yl)thiazole | H | NC(O)Me |
| (ll) | 4-amino-2-(pyridin-5-yl)thiazole | F | NC(O)-isopropyl |
| (mm) | 6-amino-2-(thiazol-2-yl)pyridine | F | NC(O)Et |
| (nn) | 6-amino-2-(thiazol-2-yl)pyridine | F | NC(O)-isopropyl |
| (oo) | 6-amino-2-(thiazol-2-yl)pyridine | F | NC(O)-cyclopropyl |
| (pp) | 4-amino-2-(pyridin-5-yl)pyrimidine | F | NC(O)Et |
| (qq) | 4-amino-2-(pyridin-5-yl)pyrimidine | F | NC(O)-isopropyl |
| (rr) | 6-amino-2-(oxazol-4-yl)pyridine | F | NC(O)Et |
| (ss) | 3-amino-1-(3-chloro-4-yl-phenyl)pyrazole | F | NC(O)Et |

| | Ar | Y | A' |
|---|---|---|---|
| (tt) | 3-amino-pyrazol-1-yl / 2-chlorophenyl | F | NC(O)-isopropyl |
| (uu) | 6-amino-pyridin-2-yl / thiazol-2-yl | F | NC(O)Et |
| (vv) | 6-amino-pyridin-2-yl / oxazol-2-yl | F | NC(O)-isopropyl |
| (ww) | 4-amino-thiazol-2-yl / pyridin-5-yl | H | NC(O)Et |
| (xx) | 4-amino-thiazol-2-yl / phenyl | F | NC(O)Et |
| (yy) | 4-amino-thiazol-2-yl / phenyl | H | NC(O)Et |
| (zz) | 2-amino-thiazol-4-yl / phenyl | F | NC(O)Et |
| (aaa) | 3-amino-pyrazol-1-yl / pyridin-2-yl | F | NC(O)OMe |
| (bbb) | 2-amino-thiazol-4-yl / pyridin-5-yl | F | NC(O)Et |
| (ccc) | 6-amino-pyridin-2-yl / oxazol-2-yl | F | NC(O)Me |
| (ddd) | 5-amino-1,2,4-thiadiazol-3-yl / phenyl | F | NC(O)Et |
| (eee) | 6-amino-pyridin-2-yl / thiazol-2-yl | F | NC(O)Me |
| (fff) | 5-amino-1,2,4-thiadiazol-3-yl / pyridin-2-yl | F | NC(O)Et |
| (ggg) | 5-amino-1,2,4-thiadiazol-3-yl / pyridin-5-yl | F | NC(O)-isopropyl |
| (hhh) | 4-amino-pyrimidin-2-yl / thiazol-2-yl | F | NC(O)Et |
| (iii) | 4-amino-thiazol-2-yl / pyrimidin-5-yl | F | NC(O)Et |
| (jjj) | 4-amino-thiazol-2-yl / pyrazin-5-yl | F | NC(O)Et |
| (kkk) | 6-amino-pyridin-2-yl / oxazol-2-yl | F | NC(O)Et |
| (lll) | 6-amino-pyridin-2-yl / thiazol-2-yl | F | NC(O)Et |

-continued

| | Ar | Y | A' |
|---|---|---|---|
| (mmm) | 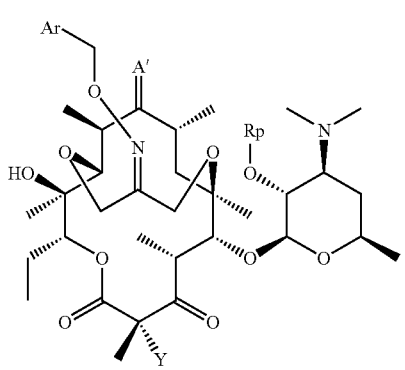 | F | NC(O)Et-d$_5$ |
| (nnn) | | F | NC(O)Et. |

28. A compound according to claim 18 represented by formula (XVI):

(XVI)

or a pharmaceutically acceptable salt, amide or ester thereof where Rp is H, and Ar, Y and A' are selected from the group consisting of:

| | Ar | Y | A' |
|---|---|---|---|
| A | 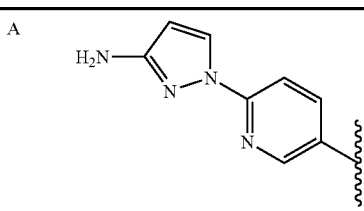 | H | O |
| B | 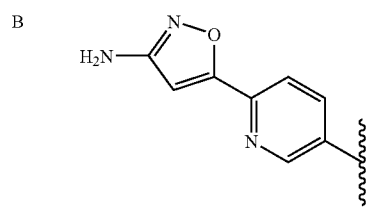 | F | O |
| C | | H | O |
| D | | H | O |
| E | | F | NC(O)Me |
| F | | H | O |
| G | | H | O |
| H | | H | O |
| I | | F | NC(O)Et. |

29. A method for treating a bacterial infection in a subject in need of such treatment, comprising administering to said subject a therapeutically effective amount of a compound according to claim 18 or claim 26.

30. A pharmaceutical composition comprising a therapeutically effective amount of a compound of claim 18 or claim 26, in combination with a pharmaceutically acceptable carrier.

31. A method for treating a bacterial infection in a subject, comprising administering to said subject a therapeutically effective amount of a pharmaceutical composition according to claim 30.

32. A method for treating cystic fibrosis in a subject, comprising administering to said subject a therapeutically effective amount of a pharmaceutical composition according to claim 30.

33. A method for treating an inflammatory disorder in a subject, comprising administering to said subject a therapeutically effective amount of a pharmaceutical composition according to claim 30.

34. The compound of claim 22, or a pharmaceutically acceptable salt or ester thereof, wherein $R_6$ is

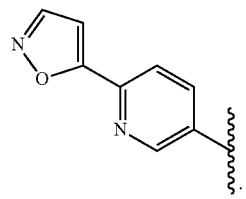 [SMILES: *c1ccc(-c2ccno2)nc1]

* * * * *

UNITED STATES PATENT AND TRADEMARK OFFICE
CERTIFICATE OF CORRECTION

PATENT NO. : 8,354,383 B2
APPLICATION NO. : 12/399801
DATED : January 15, 2013
INVENTOR(S) : In Jong Kim et al.

It is certified that error appears in the above-identified patent and that said Letters Patent is hereby corrected as shown below:

In the Claims:

Column 184

In claim 1, at line 21, after "Y1", insert -- or Y3 --.

Column 191

In claim 7, at line 3, before "protecting" delete "protected".

Column 192

In claim 10, line 41, after "where" replace "R" with -- Rp --.

Column 193

In claim 11, at line 27, before "protecting" delete "protected".

Column 195

In claim 18, line 40, after "alkyl" please replace "C-C6 alkenyl" with -- C2-C6 alkenyl --.

Column 206

In claim 24, at line 63, before "protecting" delete "protected".

Signed and Sealed this
Twenty-third Day of April, 2013

Teresa Stanek Rea
*Acting Director of the United States Patent and Trademark Office*

CERTIFICATE OF CORRECTION (continued)  
U.S. Pat. No. 8,354,383 B2

Column 216

In claim 27, please replace the (h) structure " 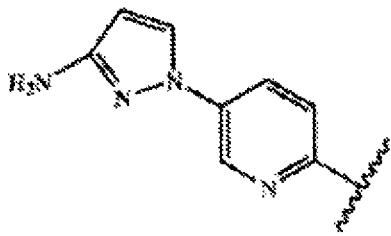 " with

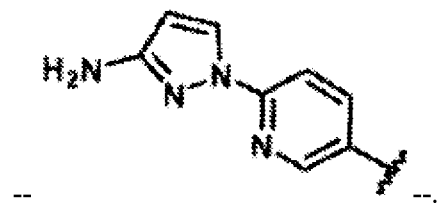

-- --.